(12) United States Patent
Sicvol et al.

(10) Patent No.: US 10,299,839 B2
(45) Date of Patent: May 28, 2019

(54) PERCUTANEOUS ACCESS DEVICES AND BONE ANCHOR ASSEMBLIES

(71) Applicant: MEDOS INTERNATIONAL SARL, Le Locle (CH)

(72) Inventors: Christopher Sicvol, Durham, NC (US); Erasmo Lopez, Wyndmoor, PA (US); Ramon Ruberte, Durham, NC (US)

(73) Assignee: Medos International Sárl, Le Locle (CH)

( * ) Notice: Subject to any disclaimer, the term of this patent is extended or adjusted under 35 U.S.C. 154(b) by 155 days.

(21) Appl. No.: 15/230,392

(22) Filed: Aug. 6, 2016

(65) Prior Publication Data

US 2016/0338737 A1     Nov. 24, 2016

Related U.S. Application Data

(63) Continuation of application No. 13/938,222, filed on Jul. 9, 2013, now Pat. No. 9,439,699, which is a
(Continued)

(51) Int. Cl.
*A61B 17/70*     (2006.01)
*A61B 17/86*     (2006.01)
(Continued)

(52) U.S. Cl.
CPC .......... *A61B 17/708* (2013.01); *A61B 17/70* (2013.01); *A61B 17/7032* (2013.01);
(Continued)

(58) Field of Classification Search
CPC .......... A61B 17/7032; A61B 17/7034; A61B 17/7035; A61B 17/7037; A61B 17/7082
See application file for complete search history.

(56) References Cited

U.S. PATENT DOCUMENTS

| 854,956 A | 5/1907 | Martin |
| 1,472,464 A | 10/1923 | Ellison |

(Continued)

FOREIGN PATENT DOCUMENTS

| AU | 2012203959 A1 | 8/2012 |
| CA | 2 577 436 A1 | 6/2006 |

(Continued)

OTHER PUBLICATIONS

European Search Report, EP14189707.4, dated Feb. 25, 2015. (13 pages).

(Continued)

*Primary Examiner* — Nicholas W Woodall
(74) *Attorney, Agent, or Firm* — Nutter McClennen & Fish LLP

(57) ABSTRACT

A percutaneous access device includes an inner tube and an outer tube disposed about at least a portion of the inner tube. The outer tube may be sized to span from a skin incision in a patient to a site proximate the spine of the patient. The distal end of the outer tube may be adapted to releasably engage a bone anchor. The inner tube may be adjustable relative to the outer tube between a first position and a second position in which the distal end of the inner tube contacts the bone anchor. A bone anchor assembly includes a bone anchor having a distal bone engaging portion and a receiving member having a recess for receiving a spinal fixation element. The proximal end of the receiving member may have an arcuate groove formed on an exterior surface thereof to facilitate connection of an instrument to the receiving member.

36 Claims, 26 Drawing Sheets

Related U.S. Application Data continuation of application No. 12/945,676, filed on Nov. 12, 2010, now Pat. No. 8,518,082, which is a continuation of application No. 11/692,531, filed on Mar. 28, 2007, now Pat. No. 7,854,751, which is a continuation of application No. 11/672,539, filed on Feb. 8, 2007, now abandoned, which is a continuation of application No. 10/738,286, filed on Dec. 16, 2003, now Pat. No. 7,179,261.

(51) Int. Cl.
  *A61B 90/00* (2016.01)
  *A61B 17/56* (2006.01)

(52) U.S. Cl.
  CPC ...... *A61B 17/7035* (2013.01); *A61B 17/7037* (2013.01); *A61B 17/7076* (2013.01); *A61B 17/7091* (2013.01); *A61B 17/8605* (2013.01); *A61B 17/7034* (2013.01); *A61B 2017/564* (2013.01); *A61B 2090/037* (2016.02)

(56) References Cited

U.S. PATENT DOCUMENTS

| | | |
|---|---|---|
| 2,005,955 A | 6/1935 | Renouf |
| 2,092,866 A | 9/1937 | Wisniewski |
| 2,243,717 A | 5/1941 | Moreira |
| 2,248,054 A | 7/1941 | Becker |
| 2,268,576 A | 1/1942 | Drewett |
| 2,338,159 A | 1/1944 | Appleton |
| 2,346,346 A | 4/1944 | Anderson |
| 2,362,999 A | 11/1944 | Hewitt |
| 2,514,589 A | 7/1950 | Penman |
| 2,524,095 A | 10/1950 | Williams et al. |
| 2,531,892 A | 11/1950 | Reese |
| 2,532,972 A | 12/1950 | Vertin |
| 2,579,438 A | 12/1951 | Longfellow |
| 2,669,896 A | 2/1954 | Clough |
| 2,684,168 A | 7/1954 | McGinnis et al. |
| 2,813,450 A | 11/1957 | Dzus |
| 3,013,244 A | 12/1961 | Rudy |
| 3,224,799 A | 12/1965 | Blose et al. |
| 3,236,275 A | 2/1966 | Smith |
| 3,604,487 A | 9/1971 | Gilbert |
| 3,640,416 A | 2/1972 | Temple |
| 3,892,232 A | 7/1975 | Neufeld |
| 3,997,138 A | 12/1976 | Crock et al. |
| 4,033,139 A | 7/1977 | Frederick |
| 4,041,636 A | 8/1977 | Folker |
| 4,041,939 A | 8/1977 | Hall |
| 4,190,091 A | 2/1980 | Colognori |
| 4,269,178 A | 5/1981 | Keene |
| 4,274,401 A | 6/1981 | Miskew |
| 4,324,036 A | 4/1982 | Reilly |
| 4,335,715 A | 6/1982 | Kirkley |
| 4,347,845 A | 9/1982 | Mayfield |
| 4,369,011 A | 1/1983 | Ploss |
| 4,373,754 A | 2/1983 | Bollfrass et al. |
| 4,382,438 A | 5/1983 | Jacobs |
| 4,409,968 A | 10/1983 | Drummond |
| 4,448,191 A | 5/1984 | Rodnyansky et al. |
| 4,484,570 A | 11/1984 | Sutter et al. |
| 4,492,749 A | 1/1985 | Scheler |
| 4,545,374 A | 10/1985 | Jacobson |
| 4,573,448 A | 3/1986 | Kambin |
| 4,600,224 A | 7/1986 | Blose |
| 4,611,580 A | 9/1986 | Wu |
| 4,653,486 A | 3/1987 | Coker |
| 4,703,954 A | 11/1987 | Ortloff et al. |
| 4,707,001 A | 11/1987 | Johnson |
| 4,722,331 A | 2/1988 | Fox |
| 4,743,260 A | 5/1988 | Burton |
| 4,748,260 A | 5/1988 | Marlett |
| 4,759,672 A | 7/1988 | Nilsen et al. |
| 4,763,644 A | 8/1988 | Webb |
| 4,790,297 A | 12/1988 | Luque |
| 4,799,372 A | 1/1989 | Marcon et al. |
| 4,805,602 A | 2/1989 | Puno et al. |
| 4,815,453 A | 3/1989 | Cotrel |
| 4,836,196 A | 6/1989 | Park et al. |
| 4,838,264 A | 6/1989 | Bremer et al. |
| 4,848,368 A | 7/1989 | Kronner |
| 4,851,453 A | 7/1989 | White et al. |
| 4,864,614 A | 9/1989 | Crowther |
| 4,877,020 A | 10/1989 | Vich et al. |
| 4,883,048 A | 11/1989 | Purnell et al. |
| 4,887,596 A | 12/1989 | Sherman |
| 4,896,661 A | 1/1990 | Bogert et al. |
| 4,913,134 A | 4/1990 | Luque |
| 4,946,458 A | 8/1990 | Harms et al. |
| 4,950,269 A | 8/1990 | Gaines, Jr. |
| 4,955,885 A | 9/1990 | Meyers |
| 4,957,495 A | 9/1990 | Kluger |
| 4,961,740 A | 10/1990 | Ray et al. |
| 5,005,562 A | 4/1991 | Cotrel |
| 5,015,247 A | 5/1991 | Michelson |
| 5,019,080 A | 5/1991 | Hemer |
| 5,020,519 A | 6/1991 | Hayes et al. |
| 5,022,791 A | 6/1991 | Isler |
| 5,034,011 A | 7/1991 | Howland |
| 5,042,982 A | 8/1991 | Harms et al. |
| 5,052,643 A | 10/1991 | Law |
| 5,067,955 A | 11/1991 | Cotrel |
| 5,084,048 A | 1/1992 | Jacob |
| 5,092,635 A | 3/1992 | DeLange et al. |
| 5,092,866 A | 3/1992 | Breard et al. |
| 5,092,867 A | 3/1992 | Harms et al. |
| 5,092,893 A | 3/1992 | Smith |
| 5,102,412 A | 4/1992 | Rogozinski |
| 5,129,388 A | 7/1992 | Vignaud et al. |
| 5,147,363 A | 9/1992 | Harle |
| 5,154,719 A | 10/1992 | Cotrel |
| 5,163,940 A | 11/1992 | Bourque |
| 5,167,664 A | 12/1992 | Hodorek |
| 5,171,279 A | 12/1992 | Mathews |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,196,013 A | 3/1993 | Harms et al. |
| 5,207,678 A | 5/1993 | Harms et al. |
| 5,217,497 A | 6/1993 | Mehdian |
| 5,242,443 A | 9/1993 | Kambin |
| 5,242,446 A | 9/1993 | Steffee et al. |
| 5,257,993 A | 11/1993 | Asher et al. |
| 5,261,907 A | 11/1993 | Vignaud et al. |
| 5,261,912 A | 11/1993 | Frigg |
| 5,261,913 A | 11/1993 | Marnay |
| 5,275,601 A | 1/1994 | Gogolewski et al. |
| 5,281,223 A | 1/1994 | Ray |
| 5,282,862 A | 2/1994 | Baker et al. |
| 5,282,863 A | 2/1994 | Burton |
| D346,217 S | 4/1994 | Sparker et al. |
| 5,306,275 A | 4/1994 | Bryan |
| 5,312,404 A | 5/1994 | Asher et al. |
| 5,321,901 A | 6/1994 | Kelly |
| 5,330,472 A | 7/1994 | Metz-Stavenhagen |
| 5,334,203 A | 8/1994 | Wagner |
| 5,334,205 A | 8/1994 | Cain |
| 5,346,493 A | 9/1994 | Stahurski et al. |
| 5,352,231 A | 10/1994 | Brumfield et al. |
| 5,354,292 A | 10/1994 | Braeuer et al. |
| 5,358,289 A | 10/1994 | Banker et al. |
| 5,360,431 A | 11/1994 | Puno et al. |
| 5,375,823 A | 12/1994 | Navas et al. |
| 5,383,454 A | 1/1995 | Bucholz |
| 5,385,583 A | 1/1995 | Cotrel |
| 5,395,371 A | 3/1995 | Miller et al. |
| 5,397,363 A | 3/1995 | Gelbard |
| 5,409,489 A | 4/1995 | Sioufi |
| 5,415,661 A | 5/1995 | Holmes |
| 5,423,816 A | 6/1995 | Lin |
| 5,427,418 A | 6/1995 | Watts |

(56) References Cited

U.S. PATENT DOCUMENTS

| | | |
|---|---|---|
| 5,429,639 A | 7/1995 | Judet |
| 5,437,667 A | 8/1995 | Papierski et al. |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,484,437 A | 1/1996 | Michelson |
| 5,484,440 A | 1/1996 | Allard |
| 5,487,742 A | 1/1996 | Cotrel |
| 5,489,307 A | 2/1996 | Kuslich et al. |
| 5,490,750 A | 2/1996 | Gundy |
| 5,496,321 A | 3/1996 | Puno et al. |
| 5,499,892 A | 3/1996 | Reed |
| 5,505,731 A | 4/1996 | Tornier |
| 5,507,745 A | 4/1996 | Logroscino et al. |
| 5,520,689 A | 5/1996 | Schlapfer et al. |
| 5,534,001 A | 7/1996 | Schlapfer et al. |
| 5,536,268 A | 7/1996 | Griss |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,248 A | 10/1996 | Mathews |
| 5,569,251 A | 10/1996 | Baker et al. |
| 5,584,834 A | 12/1996 | Errico et al. |
| 5,584,887 A | 12/1996 | Kambin |
| 5,586,984 A | 12/1996 | Errico et al. |
| 5,591,166 A | 1/1997 | Bernhardt et al. |
| 5,591,167 A | 1/1997 | Laurain et al. |
| 5,601,553 A | 2/1997 | Trebing et al. |
| 5,601,562 A | 2/1997 | Wolf et al. |
| 5,605,457 A | 2/1997 | Bailey et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,613,971 A | 3/1997 | Lower et al. |
| 5,613,987 A | 3/1997 | Kuroki et al. |
| 5,624,442 A | 4/1997 | Mellinger et al. |
| 5,628,740 A | 5/1997 | Mullane |
| 5,630,817 A | 5/1997 | Rokegem et al. |
| 5,641,256 A | 6/1997 | Gundy |
| 5,643,260 A | 7/1997 | Doherty |
| 5,643,261 A | 7/1997 | Schafer et al. |
| 5,643,273 A | 7/1997 | Clark |
| 5,647,873 A | 7/1997 | Errico et al. |
| 5,651,789 A | 7/1997 | Cotrel |
| 5,662,652 A | 9/1997 | Schafer et al. |
| 5,662,653 A | 9/1997 | Songer et al. |
| 5,667,508 A | 9/1997 | Errico et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,680,963 A | 10/1997 | Brusko et al. |
| 5,681,319 A | 10/1997 | Biedermann et al. |
| 5,681,320 A | 10/1997 | McGuire |
| 5,683,390 A | 11/1997 | Metz-Stavenhagen et al. |
| 5,683,391 A | 11/1997 | Boyd |
| 5,683,392 A | 11/1997 | Richelsoph et al. |
| 5,690,630 A | 11/1997 | Errico et al. |
| 5,697,929 A | 12/1997 | Mellinger |
| 5,704,937 A | 1/1998 | Martin |
| 5,711,709 A | 1/1998 | McCoy |
| 5,713,898 A | 2/1998 | Stucker et al. |
| 5,716,356 A | 2/1998 | Biedermann et al. |
| 5,720,751 A | 2/1998 | Jackson |
| 5,723,013 A | 3/1998 | Jeanson et al. |
| 5,725,527 A | 3/1998 | Biedermann et al. |
| 5,725,528 A | 3/1998 | Errico |
| 5,725,532 A | 3/1998 | Shoemaker |
| 5,728,098 A | 3/1998 | Sherman et al. |
| 5,733,286 A | 3/1998 | Errico et al. |
| 5,735,857 A | 4/1998 | Lane |
| 5,738,685 A | 4/1998 | Halm et al. |
| 5,741,254 A | 4/1998 | Henry et al. |
| 5,741,266 A | 4/1998 | Moran et al. |
| 5,752,957 A | 5/1998 | Ralph et al. |
| 5,752,962 A | 5/1998 | D'Urso |
| 5,772,594 A | 6/1998 | Barrick |
| 5,782,830 A | 7/1998 | Farris |
| 5,782,833 A | 7/1998 | Haider |
| 5,788,097 A | 8/1998 | McInnes |
| 5,792,044 A | 8/1998 | Foley et al. |
| 5,797,911 A | 8/1998 | Sherman et al. |
| 5,800,435 A | 9/1998 | Errico et al. |
| 5,800,547 A | 9/1998 | Schafer et al. |
| 5,810,816 A | 9/1998 | Roussouly et al. |
| 5,810,818 A | 9/1998 | Errico et al. |
| 5,817,094 A | 10/1998 | Errico et al. |
| 5,851,183 A | 12/1998 | Bucholz |
| 5,855,151 A | 1/1999 | Habermehl |
| 5,858,020 A | 1/1999 | Johnson et al. |
| 5,863,293 A | 1/1999 | Richelsoph |
| 5,865,487 A | 2/1999 | Gore et al. |
| 5,871,445 A | 2/1999 | Bucholz |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,888,221 A | 3/1999 | Gelbard |
| 5,891,034 A | 4/1999 | Bucholz |
| 5,891,145 A | 4/1999 | Morrison et al. |
| 5,891,150 A | 4/1999 | Chan |
| 5,891,158 A | 4/1999 | Manwaring et al. |
| 5,899,901 A | 5/1999 | Middleton |
| 5,899,904 A | 5/1999 | Errico et al. |
| 5,899,905 A | 5/1999 | Errico et al. |
| 5,902,231 A | 5/1999 | Foley et al. |
| RE36,221 E | 6/1999 | Breard et al. |
| 5,910,141 A | 6/1999 | Morrison et al. |
| 5,925,047 A | 7/1999 | Errico et al. |
| 5,938,663 A | 8/1999 | Petreto |
| 5,944,465 A | 8/1999 | Janitzki |
| 5,947,969 A | 9/1999 | Errico et al. |
| 5,951,553 A | 9/1999 | Betz et al. |
| 5,954,725 A | 9/1999 | Sherman et al. |
| 5,961,266 A | 10/1999 | Tseng |
| 5,961,517 A | 10/1999 | Biedermann et al. |
| 5,964,760 A | 10/1999 | Richelsoph |
| 5,976,146 A | 11/1999 | Ogawa et al. |
| 5,984,922 A | 11/1999 | McKay |
| 5,984,923 A | 11/1999 | Breard |
| 5,989,254 A | 11/1999 | Katz |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,033,406 A | 3/2000 | Mathews |
| 6,036,692 A | 3/2000 | Burel et al. |
| 6,053,917 A | 4/2000 | Sherman et al. |
| 6,056,753 A | 5/2000 | Jackson |
| 6,059,786 A | 5/2000 | Jackson |
| 6,063,088 A | 5/2000 | Winslow |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,083,225 A | 7/2000 | Winslow et al. |
| 6,083,227 A | 7/2000 | Saurat et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat et al. |

(56) References Cited

U.S. PATENT DOCUMENTS

| | | |
|---|---|---|
| 6,102,912 A | 8/2000 | Cazin et al. |
| 6,102,913 A | 8/2000 | Jackson |
| 6,110,172 A | 8/2000 | Jackson |
| 6,113,601 A | 9/2000 | Tatar |
| 6,113,602 A | 9/2000 | Sand |
| 6,117,137 A | 9/2000 | Halm et al. |
| 6,120,760 A | 9/2000 | Hotten et al. |
| 6,123,707 A | 9/2000 | Wagner |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,139,549 A | 10/2000 | Keller |
| 6,139,551 A | 10/2000 | Michelson et al. |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,189,422 B1 | 2/2001 | Stihl |
| 6,193,720 B1 | 2/2001 | Yuan et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,226,548 B1 | 5/2001 | Foley et al. |
| 6,235,028 B1 | 5/2001 | Brumfield et al. |
| 6,235,034 B1 | 5/2001 | Bray |
| 6,241,730 B1 | 6/2001 | Alby |
| 6,248,105 B1 | 6/2001 | Schlapfer et al. |
| 6,248,107 B1 | 6/2001 | Foley et al. |
| 6,251,112 B1 | 6/2001 | Jackson |
| 6,254,146 B1 | 7/2001 | Church |
| 6,254,602 B1 | 7/2001 | Justis |
| 6,258,090 B1 | 7/2001 | Jackson |
| 6,261,287 B1 | 7/2001 | Metz-Stavenhagen |
| 6,267,764 B1 | 7/2001 | Elberg |
| 6,267,765 B1 | 7/2001 | Taylor et al. |
| 6,273,888 B1 | 8/2001 | Justis |
| 6,277,122 B1 | 8/2001 | McGahan |
| 6,279,356 B1 | 8/2001 | Takahashi et al. |
| 6,280,422 B1 | 8/2001 | Sanchez-Browning |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,290,700 B1 | 9/2001 | Schmotzer |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,299,616 B1 | 10/2001 | Beger |
| 6,302,633 B1 | 10/2001 | Poe |
| 6,302,888 B1 | 10/2001 | Mellinger et al. |
| 6,309,391 B1 | 10/2001 | Crandall et al. |
| 6,315,564 B1 | 11/2001 | Levisman |
| 6,315,779 B1 | 11/2001 | Morrison et al. |
| 6,331,179 B1 | 12/2001 | Freid et al. |
| 6,355,040 B1 | 3/2002 | Richelsoph et al. |
| 6,358,254 B1 | 3/2002 | Anderson |
| 6,361,535 B2 | 3/2002 | Jackson |
| RE37,665 E | 4/2002 | Ralph et al. |
| 6,368,321 B1 | 4/2002 | Jackson |
| 6,371,957 B1 | 4/2002 | Amrein et al. |
| 6,371,989 B1 | 4/2002 | Chauvin et al. |
| 6,379,356 B1 | 4/2002 | Jackson |
| 6,387,097 B1 | 5/2002 | Alby |
| 6,402,752 B2 | 6/2002 | Schaffler-Wachter et al. |
| 6,402,757 B1 | 6/2002 | Moore, III et al. |
| 6,416,515 B1 | 7/2002 | Wagner |
| 6,428,541 B1 | 8/2002 | Boyd et al. |
| 6,440,132 B1 | 8/2002 | Jackson |
| 6,440,133 B1 | 8/2002 | Beale et al. |
| 6,440,137 B1 | 8/2002 | Horvath et al. |
| 6,443,953 B1 | 9/2002 | Perra et al. |
| 6,443,956 B1 | 9/2002 | Ray |
| 6,451,021 B1 | 9/2002 | Ralph et al. |
| 6,454,768 B1 | 9/2002 | Jackson |
| 6,454,772 B1 | 9/2002 | Jackson |
| 6,458,131 B1 | 10/2002 | Ray |
| 6,458,132 B2 | 10/2002 | Choi |
| 6,468,276 B1 | 10/2002 | McKay |
| 6,471,703 B1 | 10/2002 | Ashman |
| 6,471,705 B1 | 10/2002 | Biedermann et al. |
| 6,475,218 B2 | 11/2002 | Gournay et al. |
| 6,478,797 B1 | 11/2002 | Paul |
| 6,478,798 B1 | 11/2002 | Howland |
| 6,478,800 B1 | 11/2002 | Fraser et al. |
| 6,478,801 B1 | 11/2002 | Ralph et al. |
| 6,485,220 B2 | 11/2002 | Hecht |
| 6,485,491 B1 | 11/2002 | Farris et al. |
| 6,485,492 B1 | 11/2002 | Halm et al. |
| 6,485,494 B1 | 11/2002 | Haider |
| 6,485,518 B1 | 11/2002 | Cornwall et al. |
| 6,487,798 B2 | 12/2002 | Sueshige |
| 6,488,681 B2 | 12/2002 | Martin et al. |
| 6,488,682 B2 | 12/2002 | Kikuchi et al. |
| 6,488,683 B2 | 12/2002 | Lieberman |
| 6,508,818 B2 | 1/2003 | Steiner et al. |
| 6,511,484 B2 | 1/2003 | Torode et al. |
| 6,520,962 B1 | 2/2003 | Taylor et al. |
| 6,520,963 B1 | 2/2003 | McKinley |
| 6,520,990 B1 | 2/2003 | Ray |
| 6,524,315 B1 | 2/2003 | Selvitelli et al. |
| 6,527,804 B1 | 3/2003 | Gauchet et al. |
| 6,530,028 B1 | 3/2003 | Yokoyama |
| 6,530,929 B1 | 3/2003 | Justis et al. |
| 6,533,786 B1 | 3/2003 | Needham et al. |
| 6,537,276 B2 | 3/2003 | Metz-Stavenhagen |
| 6,539,826 B2 | 4/2003 | Oesterle et al. |
| 6,540,748 B2 | 4/2003 | Lombardo |
| 6,540,749 B2 | 4/2003 | Schafer et al. |
| 6,547,790 B2 | 4/2003 | Harkey, III et al. |
| 6,551,320 B2 | 4/2003 | Lieberman |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,038 B1 | 5/2003 | Morrison |
| 6,562,040 B1 | 5/2003 | Wagner |
| 6,565,565 B1 | 5/2003 | Yuan et al. |
| 6,565,567 B1 | 5/2003 | Haider |
| 6,572,618 B1 | 6/2003 | Morrison |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,599,294 B2 | 7/2003 | Fuss et al. |
| 6,648,887 B2 | 7/2003 | Ashman |
| 6,602,255 B1 | 8/2003 | Campbell et al. |
| 6,610,063 B2 | 8/2003 | Kumar et al. |
| 6,613,050 B2 | 9/2003 | Wagner et al. |
| 6,616,667 B1 | 9/2003 | Steiger et al. |
| 6,616,669 B2 | 9/2003 | Ogilvie et al. |
| 6,623,484 B2 | 9/2003 | Betz et al. |
| 6,623,485 B2 | 9/2003 | Doubler et al. |
| 6,626,347 B2 | 9/2003 | Ng |
| 6,626,907 B2 | 9/2003 | Campbell et al. |
| 6,626,908 B2 | 9/2003 | Cooper et al. |
| 6,635,060 B2 | 10/2003 | Hanson et al. |
| 6,641,586 B2 | 11/2003 | Varieur |
| 6,648,885 B1 | 11/2003 | Friesem |
| 6,648,888 B1 | 11/2003 | Shluzas |
| 6,652,526 B1 | 11/2003 | Arafiles |
| 6,652,527 B2 | 11/2003 | Zucherman et al. |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,660,006 B2 | 12/2003 | Markworth et al. |
| 6,663,632 B1 | 12/2003 | Frigg |
| 6,663,635 B2 | 12/2003 | Frigg et al. |
| 6,673,073 B1 | 1/2004 | Schafer |

(56) References Cited

U.S. PATENT DOCUMENTS

| | | |
|---|---|---|
| 6,676,661 B1 | 1/2004 | Martin Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,248 B2 | 3/2004 | Jackson |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,726,687 B2 | 4/2004 | Jackson |
| 6,726,689 B2 | 4/2004 | Jackson |
| 6,730,089 B2 | 5/2004 | Jackson |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,740,089 B2 | 5/2004 | Haider |
| 6,743,231 B1 | 6/2004 | Gray et al. |
| 6,746,449 B2 | 6/2004 | Jones et al. |
| 6,746,454 B2 | 6/2004 | Winterbottom et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,719 B2 | 7/2004 | Justis et al. |
| 6,761,723 B2 | 7/2004 | Buttermann et al. |
| 6,767,351 B2 | 7/2004 | Orbay et al. |
| 6,770,075 B2 | 8/2004 | Howland |
| 6,778,861 B1 | 8/2004 | Liebrecht et al. |
| 6,780,186 B2 | 8/2004 | Errico et al. |
| 6,783,527 B2 | 8/2004 | Drewry et al. |
| 6,790,208 B2 | 9/2004 | Oribe et al. |
| 6,790,209 B2 | 9/2004 | Beale et al. |
| 6,793,656 B1 | 9/2004 | Mathews |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,835,205 B2 | 12/2004 | Atkinson et al. |
| 6,837,889 B2 | 1/2005 | Shluzas |
| 6,840,940 B2 | 1/2005 | Ralph et al. |
| 6,843,791 B2 | 1/2005 | Serhan |
| 6,857,343 B1 | 2/2005 | Easterbrooks et al. |
| 6,858,031 B2 | 2/2005 | Morrison et al. |
| 6,869,432 B2 | 3/2005 | Schlapfer et al. |
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,905,500 B2 | 6/2005 | Jeon et al. |
| 6,911,030 B1 | 6/2005 | Vanacker et al. |
| 6,932,817 B2 | 8/2005 | Baynham et al. |
| 6,932,820 B2 | 8/2005 | Osman |
| 6,932,822 B2 | 8/2005 | Oribe et al. |
| 6,945,972 B2 | 9/2005 | Frigg et al. |
| 6,953,462 B2 | 10/2005 | Lieberman |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,004,947 B2 | 2/2006 | Shluzas et al. |
| RE39,035 E | 3/2006 | Finn et al. |
| 7,008,422 B2 | 3/2006 | Foley et al. |
| 7,008,424 B2 | 3/2006 | Teitelbaum |
| 7,011,660 B2 | 3/2006 | Sherman et al. |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,052,497 B2 | 5/2006 | Sherman et al. |
| 7,056,321 B2 | 6/2006 | Pagliuca et al. |
| 7,066,062 B2 | 6/2006 | Flesher |
| 7,066,937 B2 | 6/2006 | Shluzas |
| 7,081,116 B1 | 7/2006 | Carly |
| 7,081,117 B2 | 7/2006 | Bono et al. |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,090,679 B2 | 8/2006 | Saint-Martin et al. |
| 7,090,680 B2 | 8/2006 | Bonati et al. |
| 7,094,242 B2 | 8/2006 | Ralph et al. |
| 7,118,576 B2 | 10/2006 | Gitis et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,156,850 B2 | 1/2007 | Kim |
| 7,160,300 B2 | 1/2007 | Jackson |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,179,261 B2 | 2/2007 | Sicvol et al. |
| 7,186,255 B2 | 3/2007 | Baynham et al. |
| 7,188,626 B2 | 3/2007 | Foley et al. |
| 7,207,991 B2 | 4/2007 | Michelson |
| 7,207,992 B2 | 4/2007 | Ritland |
| 7,211,085 B2 | 5/2007 | Michelson |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,235,075 B1 | 6/2007 | Metz-Stavenhagen |
| 7,250,052 B2 | 7/2007 | Landry et al. |
| 7,264,621 B2 | 9/2007 | Coates et al. |
| 7,270,665 B2 | 9/2007 | Morrison et al. |
| 7,282,064 B2 | 10/2007 | Chin |
| 7,290,347 B2 | 11/2007 | Augostino et al. |
| 7,291,151 B2 | 11/2007 | Alvarez |
| 7,291,153 B2 | 11/2007 | Glascott |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,361,196 B2 | 4/2008 | Fallin et al. |
| 7,377,921 B2 | 5/2008 | Studer et al. |
| 7,377,922 B2 | 5/2008 | Barker |
| 7,445,627 B2 | 11/2008 | Hawkes et al. |
| 7,462,182 B2 | 12/2008 | Lim |
| 7,465,306 B2 | 12/2008 | Pond, Jr. et al. |
| 7,470,279 B2 | 12/2008 | Jackson |
| 7,476,228 B2 | 1/2009 | Abdou |
| 7,476,238 B2 | 1/2009 | Panjabi |
| 7,479,156 B2 | 1/2009 | Lourdel et al. |
| 7,481,813 B1 | 1/2009 | Purcell |

(56) References Cited

U.S. PATENT DOCUMENTS

| | | |
|---|---|---|
| 7,491,207 B2 | 2/2009 | Keyer et al. |
| 7,491,208 B2 | 2/2009 | Pond, Jr. et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,638 B2 | 5/2009 | Anderson et al. |
| 7,527,640 B2 | 5/2009 | Ziolo et al. |
| 7,530,992 B2 | 5/2009 | Biedermann et al. |
| 7,547,318 B2 | 6/2009 | Birkmeyer et al. |
| 7,556,639 B2 | 7/2009 | Rothman et al. |
| 7,559,942 B2 | 7/2009 | Paul et al. |
| 7,559,943 B2 | 7/2009 | Mujwid |
| 7,563,264 B2 | 7/2009 | Landry et al. |
| 7,563,274 B2 | 7/2009 | Justis et al. |
| 7,563,275 B2 | 7/2009 | Falahee et al. |
| 7,563,283 B2 | 7/2009 | Kwak |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,589 B2 | 9/2009 | Falahee |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,601,171 B2 | 10/2009 | Ainsworth et al. |
| 7,604,653 B2 | 10/2009 | Kitchen |
| 7,604,654 B2 | 10/2009 | Fallin et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,618,442 B2 | 11/2009 | Spitler et al. |
| 7,618,443 B2 | 11/2009 | Abdou |
| 7,621,912 B2 | 11/2009 | Harms et al. |
| 7,621,918 B2 | 11/2009 | Jackson |
| 7,621,940 B2 | 11/2009 | Harms et al. |
| 7,621,941 B2 | 11/2009 | Schlapfer et al. |
| 7,625,393 B2 | 12/2009 | Fallin et al. |
| 7,625,394 B2 | 12/2009 | Molz, IV et al. |
| 7,632,292 B2 | 12/2009 | Sengupta et al. |
| 7,641,673 B2 | 1/2010 | Le Couedic et al. |
| 7,641,674 B2 | 1/2010 | Young |
| 7,645,294 B2 | 1/2010 | Kalfas et al. |
| 7,648,522 B2 | 1/2010 | David |
| 7,651,502 B2 | 1/2010 | Jackson |
| 7,651,515 B2 | 1/2010 | Mack et al. |
| 7,655,026 B2 | 2/2010 | Justis et al. |
| 7,658,739 B2 | 2/2010 | Shluzas |
| 7,658,752 B2 | 2/2010 | Labrom et al. |
| 7,666,188 B2 | 2/2010 | Anderson et al. |
| 7,674,277 B2 | 3/2010 | Burd et al. |
| 7,678,112 B2 | 3/2010 | Rezach |
| 7,678,136 B2 | 3/2010 | Doubler et al. |
| 7,678,137 B2 | 3/2010 | Butler et al. |
| 7,678,139 B2 | 3/2010 | Garamszegi et al. |
| 7,682,375 B2 | 3/2010 | Ritland |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,475 B2 | 4/2010 | Justis et al. |
| 7,695,496 B2 | 4/2010 | Labrom et al. |
| 7,695,497 B2 | 4/2010 | Cordaro et al. |
| 7,695,498 B2 | 4/2010 | Ritland |
| 7,695,514 B2 | 4/2010 | Kwak |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,708,763 B2 | 5/2010 | Selover et al. |
| 7,713,288 B2 | 5/2010 | Timm et al. |
| 7,717,939 B2 | 5/2010 | Ludwig et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,260 B2 | 6/2010 | Albert et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,233 B2 | 7/2010 | Farr et al. |
| 7,749,258 B2 | 7/2010 | Biedermann et al. |
| 7,758,618 B2 | 7/2010 | Walder et al. |
| 7,763,052 B2 | 7/2010 | Jahng |
| 7,763,057 B2 | 7/2010 | Abdelgany et al. |
| 7,766,915 B2 | 8/2010 | Jackson |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,067 B2 | 8/2010 | Jackson |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,815,665 B2 | 10/2010 | Jahng et al. |
| 7,819,902 B2 | 10/2010 | Abdelgany et al. |
| 7,824,430 B2 | 11/2010 | Allard et al. |
| 7,833,250 B2 | 11/2010 | Jackson |
| 7,833,252 B2 | 11/2010 | Justis et al. |
| 7,846,190 B2 | 12/2010 | Ball |
| 7,850,715 B2 | 12/2010 | Banouskou et al. |
| 7,854,751 B2 | 12/2010 | Sicvol et al. |
| 7,862,587 B2 | 1/2011 | Jackson |
| 7,862,588 B2 | 1/2011 | Abdou |
| 7,887,539 B2 | 2/2011 | Dunbar, Jr. et al. |
| 7,896,902 B2 | 3/2011 | Jeon et al. |
| 7,901,436 B2 | 3/2011 | Baccelli |
| 7,901,437 B2 | 3/2011 | Jackson |
| 7,909,830 B2 | 3/2011 | Frigg et al. |
| 7,947,064 B2 | 5/2011 | Bergeron et al. |
| 7,951,170 B2 | 5/2011 | Jackson |
| 7,955,358 B2 | 6/2011 | Albert |
| 7,967,848 B2 | 6/2011 | Abdelgany |
| 7,985,242 B2 | 7/2011 | Forton et al. |
| 7,988,694 B2 | 8/2011 | Barrus et al. |
| 8,034,083 B2 | 10/2011 | Abdelgany et al. |
| 8,055,487 B2 | 11/2011 | James |
| 8,062,340 B2 | 11/2011 | Berrevoets et al. |
| 8,066,739 B2 | 11/2011 | Jackson |
| 8,075,599 B2 | 12/2011 | Johnson et al. |
| 8,083,776 B2 | 12/2011 | Alvarez |
| 8,100,915 B2 | 1/2012 | Jackson |
| 8,105,361 B2 | 1/2012 | Anderson et al. |
| 8,152,837 B2 | 4/2012 | Altarac et al. |
| 8,162,948 B2 | 4/2012 | Jackson |
| 8,172,876 B2 | 5/2012 | Janowski et al. |
| 8,197,517 B1 | 6/2012 | Lab et al. |
| 8,206,394 B2 | 6/2012 | Stad et al. |
| 8,211,110 B1 | 7/2012 | Corin et al. |
| 8,226,690 B2 | 7/2012 | Altarac et al. |
| 8,267,969 B2 | 9/2012 | Altarac et al. |
| 8,277,491 B2 | 10/2012 | Selover et al. |
| 8,292,926 B2 | 10/2012 | Jackson |
| 8,292,934 B2 | 10/2012 | Justis et al. |
| 8,292,958 B1 | 10/2012 | Bruffey et al. |
| 8,343,165 B2 | 1/2013 | Berrevoets |
| 8,377,067 B2 | 2/2013 | Jackson |

(56) References Cited

U.S. PATENT DOCUMENTS

| | | |
|---|---|---|
| 8,377,100 B2 | 2/2013 | Jackson |
| 8,377,101 B2 | 2/2013 | Barrus et al. |
| 8,388,659 B1 | 3/2013 | Lab et al. |
| 8,398,683 B2 | 3/2013 | Berrevoets et al. |
| 8,409,256 B2 | 4/2013 | Arnold et al. |
| 8,414,588 B2 | 4/2013 | Stad et al. |
| 8,439,924 B1 | 5/2013 | McBride et al. |
| 8,475,498 B2 | 7/2013 | Jackson |
| 8,518,082 B2 | 8/2013 | Sicvol et al. |
| 8,535,352 B2 | 9/2013 | Altarac et al. |
| 8,585,743 B2 | 11/2013 | Ampuero et al. |
| 8,617,210 B2 | 12/2013 | Sicvol et al. |
| 9,050,148 B2 | 6/2015 | Jackson |
| 9,055,978 B2 | 6/2015 | Jackson |
| 9,056,016 B2 | 6/2015 | Reiley et al. |
| 9,101,415 B2 | 8/2015 | Jackson |
| 9,173,682 B2 | 11/2015 | Jackson |
| 9,216,039 B2 | 12/2015 | Jackson |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 9,439,699 B2 | 9/2016 | Sicvol et al. |
| 2001/0001119 A1 | 5/2001 | Lombardo |
| 2001/0007941 A1 | 7/2001 | Steiner et al. |
| 2001/0010000 A1 | 7/2001 | Gertzbein et al. |
| 2001/0012937 A1 | 8/2001 | Schaffler-Wachter et al. |
| 2001/0023350 A1 | 9/2001 | Choi |
| 2001/0025180 A1 | 9/2001 | Jackson |
| 2001/0025553 A1 | 10/2001 | Oesterle et al. |
| 2001/0027318 A1 | 10/2001 | Oribe et al. |
| 2001/0029375 A1 | 10/2001 | Betz et al. |
| 2001/0034521 A1 | 10/2001 | Bailey et al. |
| 2001/0037111 A1 | 11/2001 | Dixon et al. |
| 2001/0041894 A1 | 11/2001 | Campbell et al. |
| 2001/0047173 A1 | 11/2001 | Schlapfer et al. |
| 2001/0047174 A1 | 11/2001 | Donno et al. |
| 2001/0047175 A1 | 11/2001 | Doubler et al. |
| 2002/0004683 A1 | 1/2002 | Michelson |
| 2002/0007183 A1 | 1/2002 | Lee et al. |
| 2002/0007184 A1 | 1/2002 | Ogilvie et al. |
| 2002/0010467 A1 | 1/2002 | Cooper et al. |
| 2002/0013585 A1 | 1/2002 | Gournay et al. |
| 2002/0013586 A1 | 1/2002 | Justis et al. |
| 2002/0016594 A1 | 2/2002 | Schlapfer et al. |
| 2002/0022764 A1 | 2/2002 | Smith et al. |
| 2002/0022842 A1 | 2/2002 | Horvath et al. |
| 2002/0026192 A1 | 2/2002 | Schmiel et al. |
| 2002/0026193 A1 | 2/2002 | Barker et al. |
| 2002/0029040 A1 | 3/2002 | Morrison et al. |
| 2002/0032443 A1 | 3/2002 | Sherman et al. |
| 2002/0035365 A1 | 3/2002 | Kumar et al. |
| 2002/0035366 A1 | 3/2002 | Walder et al. |
| 2002/0035367 A1 | 3/2002 | Ritland |
| 2002/0040243 A1 | 4/2002 | Attali et al. |
| 2002/0045898 A1 | 4/2002 | Freid et al. |
| 2002/0045899 A1 | 4/2002 | Errico et al. |
| 2002/0045904 A1 | 4/2002 | Fuss et al. |
| 2002/0049444 A1 | 4/2002 | Knox |
| 2002/0049446 A1 | 4/2002 | Harkey et al. |
| 2002/0055739 A1 | 5/2002 | Lieberman |
| 2002/0055740 A1 | 5/2002 | Lieberman |
| 2002/0055741 A1 | 5/2002 | Schlapfer et al. |
| 2002/0058942 A1 | 5/2002 | Biedermann et al. |
| 2002/0058950 A1 | 5/2002 | Winterbottom et al. |
| 2002/0068938 A1 | 6/2002 | Jackson |
| 2002/0068940 A1 | 6/2002 | Gaines |
| 2002/0068941 A1 | 6/2002 | Hanson et al. |
| 2002/0068975 A1 | 6/2002 | Teitelbaum et al. |
| 2002/0072751 A1 | 6/2002 | Jackson |
| 2002/0077701 A1 | 6/2002 | Kuslich |
| 2002/0082602 A1 | 6/2002 | Biedermann et al. |
| 2002/0082603 A1 | 6/2002 | Dixon et al. |
| 2002/0087159 A1 | 7/2002 | Thomas |
| 2002/0087161 A1 | 7/2002 | Randall et al. |
| 2002/0091386 A1 | 7/2002 | Martin et al. |
| 2002/0091390 A1 | 7/2002 | Michelson |
| 2002/0095153 A1 | 7/2002 | Jones et al. |
| 2002/0103487 A1 | 8/2002 | Errico et al. |
| 2002/0111626 A1 | 8/2002 | Ralph et al. |
| 2002/0111628 A1 | 8/2002 | Ralph et al. |
| 2002/0116000 A1 | 8/2002 | Zucherman et al. |
| 2002/0116001 A1 | 8/2002 | Schafer et al. |
| 2002/0120270 A1 | 8/2002 | Trieu et al. |
| 2002/0120272 A1 | 8/2002 | Yuan et al. |
| 2002/0123752 A1 | 9/2002 | Schultheiss et al. |
| 2002/0133154 A1 | 9/2002 | Saint Martin |
| 2002/0133158 A1 | 9/2002 | Saint Martin |
| 2002/0133159 A1 | 9/2002 | Jackson |
| 2002/0138076 A1 | 9/2002 | Biedermann et al. |
| 2002/0138077 A1 | 9/2002 | Ferree |
| 2002/0143330 A1 | 10/2002 | Shluzas |
| 2002/0143332 A1 | 10/2002 | Lin et al. |
| 2002/0143338 A1 | 10/2002 | Orbay et al. |
| 2002/0143341 A1 | 10/2002 | Biedermann et al. |
| 2002/0161368 A1 | 10/2002 | Foley et al. |
| 2002/0161370 A1 | 10/2002 | Frigg et al. |
| 2002/0169448 A1 | 11/2002 | Vanacker |
| 2002/0169450 A1 | 11/2002 | Lange |
| 2002/0173789 A1 | 11/2002 | Howland |
| 2002/0173791 A1 | 11/2002 | Howland |
| 2002/0183747 A1 | 12/2002 | Jao et al. |
| 2002/0183748 A1 | 12/2002 | Martin et al. |
| 2002/0183749 A1 | 12/2002 | Burgess et al. |
| 2002/0188295 A1 | 12/2002 | Martz et al. |
| 2002/0193795 A1 | 12/2002 | Gertzbein et al. |
| 2002/0198526 A1 | 12/2002 | Shaolian et al. |
| 2003/0004511 A1 | 1/2003 | Ferree |
| 2003/0004512 A1 | 1/2003 | Farris et al. |
| 2003/0004519 A1 | 1/2003 | Torode et al. |
| 2003/0009168 A1 | 1/2003 | Beale et al. |
| 2003/0023240 A1 | 1/2003 | Amrein et al. |
| 2003/0023243 A1 | 1/2003 | Biedermann et al. |
| 2003/0026529 A1 | 2/2003 | Durkin et al. |
| 2003/0028190 A1 | 2/2003 | Patel et al. |
| 2003/0032957 A1 | 2/2003 | McKinley |
| 2003/0045875 A1 | 3/2003 | Bertranou et al. |
| 2003/0045879 A1 | 3/2003 | Minfelde et al. |
| 2003/0050640 A1 | 3/2003 | Lee et al. |
| 2003/0055426 A1 | 3/2003 | Carbone et al. |
| 2003/0055427 A1 | 3/2003 | Graf |
| 2003/0060823 A1 | 3/2003 | Bryan |
| 2003/0060824 A1 | 3/2003 | Viart et al. |
| 2003/0060826 A1 | 3/2003 | Foley et al. |
| 2003/0073996 A1 | 4/2003 | Doubler et al. |
| 2003/0073998 A1 | 4/2003 | Pagliuca et al. |
| 2003/0078580 A1 | 4/2003 | Shitoto |
| 2003/0083657 A1 | 5/2003 | Drewry et al. |
| 2003/0083667 A1 | 5/2003 | Ralph et al. |
| 2003/0093077 A1 | 5/2003 | Schlapfer et al. |
| 2003/0093078 A1 | 5/2003 | Ritland |
| 2003/0100896 A1 | 5/2003 | Biedermann et al. |
| 2003/0100897 A1 | 5/2003 | Metz-Stavenhagen |
| 2003/0100904 A1 | 5/2003 | Biedermann |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0120275 A1 | 6/2003 | Lenke et al. |
| 2003/0125741 A1 | 7/2003 | Biedermann et al. |
| 2003/0125749 A1 | 7/2003 | Yuan et al. |
| 2003/0130659 A1 | 7/2003 | Haider |
| 2003/0130661 A1 | 7/2003 | Osman |
| 2003/0135210 A1 | 7/2003 | Dixon et al. |
| 2003/0135217 A1 | 7/2003 | Buttermann et al. |
| 2003/0149432 A1 | 8/2003 | Frigg et al. |
| 2003/0150897 A1 | 8/2003 | Ng |
| 2003/0153911 A1 | 8/2003 | Shluzas |
| 2003/0153912 A1 | 8/2003 | Graf |
| 2003/0153920 A1 | 8/2003 | Ralph et al. |
| 2003/0163133 A1 | 8/2003 | Altarac et al. |
| 2003/0167058 A1 | 9/2003 | Shluzas |
| 2003/0171749 A1 | 9/2003 | Le Couedic et al. |
| 2003/0176862 A1 | 9/2003 | Taylor et al. |

(56) References Cited

U.S. PATENT DOCUMENTS

| | | |
|---|---|---|
| 2003/0176863 A1 | 9/2003 | Ueyama et al. |
| 2003/0181913 A1 | 9/2003 | Lieberman |
| 2003/0187433 A1 | 10/2003 | Lin |
| 2003/0191469 A1 | 10/2003 | Ralph et al. |
| 2003/0191470 A1 | 10/2003 | Ritland |
| 2003/0199872 A1* | 10/2003 | Markworth ........ A61B 17/7086 606/86 A |
| 2003/0199873 A1 | 10/2003 | Richelsoph |
| 2003/0199874 A1 | 10/2003 | Michelson |
| 2003/0208203 A1 | 11/2003 | Lim et al. |
| 2003/0208204 A1 | 11/2003 | Bailey et al. |
| 2003/0208275 A1 | 11/2003 | Michelson |
| 2003/0212398 A1 | 11/2003 | Jackson |
| 2003/0216735 A1 | 11/2003 | Altarac et al. |
| 2003/0216748 A1 | 11/2003 | Gitis et al. |
| 2003/0216768 A1 | 11/2003 | Gitis et al. |
| 2003/0220642 A1 | 11/2003 | Freudiger |
| 2003/0220643 A1 | 11/2003 | Ferree |
| 2003/0225408 A1 | 12/2003 | Nichols et al. |
| 2003/0229345 A1 | 12/2003 | Stahurski |
| 2003/0229347 A1 | 12/2003 | Sherman et al. |
| 2003/0236529 A1 | 12/2003 | Shluzas et al. |
| 2004/0002708 A1 | 1/2004 | Ritland |
| 2004/0006342 A1 | 1/2004 | Altarac et al. |
| 2004/0034351 A1 | 2/2004 | Sherman et al. |
| 2004/0039383 A1 | 2/2004 | Jackson |
| 2004/0039384 A1 | 2/2004 | Boehm et al. |
| 2004/0039385 A1 | 2/2004 | Mazda et al. |
| 2004/0044335 A1 | 3/2004 | de la Torre et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0073218 A1 | 4/2004 | Dahners |
| 2004/0078051 A1 | 4/2004 | Davison et al. |
| 2004/0078082 A1 | 4/2004 | Lange |
| 2004/0087949 A1 | 5/2004 | Bono et al. |
| 2004/0087950 A1 | 5/2004 | Teitelbaum |
| 2004/0087952 A1 | 5/2004 | Borgstrom et al. |
| 2004/0092934 A1 | 5/2004 | Howland |
| 2004/0092938 A1 | 5/2004 | Carli |
| 2004/0097933 A1 | 5/2004 | Lourdel et al. |
| 2004/0106925 A1 | 6/2004 | Culbert |
| 2004/0111091 A1 | 6/2004 | Ogilvie et al. |
| 2004/0116929 A1 | 6/2004 | Barker et al. |
| 2004/0122442 A1 | 6/2004 | Lewis |
| 2004/0133207 A1 | 7/2004 | Abdou |
| 2004/0138662 A1 | 7/2004 | Landry et al. |
| 2004/0143265 A1* | 7/2004 | Landry .............. A61B 17/1604 606/86 A |
| 2004/0147928 A1 | 7/2004 | Landry et al. |
| 2004/0147929 A1 | 7/2004 | Biedermann et al. |
| 2004/0147937 A1 | 7/2004 | Dunbar et al. |
| 2004/0153068 A1 | 8/2004 | Janowski et al. |
| 2004/0158245 A1 | 8/2004 | Chin |
| 2004/0158247 A1 | 8/2004 | Sitiso et al. |
| 2004/0158258 A1 | 8/2004 | Bonati et al. |
| 2004/0162560 A1 | 8/2004 | Raynor et al. |
| 2004/0167525 A1 | 8/2004 | Jackson |
| 2004/0172022 A1 | 9/2004 | Landry et al. |
| 2004/0172025 A1 | 9/2004 | Drewry et al. |
| 2004/0172031 A1 | 9/2004 | Rubecamp et al. |
| 2004/0176766 A1 | 9/2004 | Shluzas |
| 2004/0176776 A1 | 9/2004 | Zubok et al. |
| 2004/0181224 A1 | 9/2004 | Biedermann et al. |
| 2004/0186473 A1 | 9/2004 | Cournoyer et al. |
| 2004/0186474 A1 | 9/2004 | Matthis et al. |
| 2004/0186475 A1 | 9/2004 | Falahee |
| 2004/0193160 A1 | 9/2004 | Richelsoph |
| 2004/0204711 A1 | 10/2004 | Jackson |
| 2004/0210216 A1 | 10/2004 | Farris et al. |
| 2004/0215190 A1 | 10/2004 | Nguyen et al. |
| 2004/0215191 A1 | 10/2004 | Kitchen |
| 2004/0220567 A1 | 11/2004 | Eisermann et al. |
| 2004/0220671 A1 | 11/2004 | Ralph et al. |
| 2004/0225289 A1 | 11/2004 | Biedermann et al. |
| 2004/0230100 A1 | 11/2004 | Shluzas |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0243139 A1 | 12/2004 | Lewis et al. |
| 2004/0249378 A1 | 12/2004 | Saint Martin et al. |
| 2004/0249380 A1 | 12/2004 | Glascott |
| 2004/0254574 A1 | 12/2004 | Morrison et al. |
| 2004/0260283 A1 | 12/2004 | Wu et al. |
| 2004/0267260 A1 | 12/2004 | Mack et al. |
| 2004/0267264 A1 | 12/2004 | Konieczynski et al. |
| 2005/0010219 A1 | 1/2005 | Dalton |
| 2005/0010221 A1 | 1/2005 | Dalton |
| 2005/0027296 A1 | 2/2005 | Thramann et al. |
| 2005/0033298 A1 | 2/2005 | Hawkes et al. |
| 2005/0033436 A1 | 2/2005 | Schlapfer et al. |
| 2005/0033439 A1 | 2/2005 | Gordon et al. |
| 2005/0038430 A1 | 2/2005 | McKinley |
| 2005/0038432 A1 | 2/2005 | Shaolian et al. |
| 2005/0038433 A1 | 2/2005 | Young |
| 2005/0049589 A1 | 3/2005 | Jackson |
| 2005/0049708 A1 | 3/2005 | Atkinson et al. |
| 2005/0055026 A1 | 3/2005 | Biedermann et al. |
| 2005/0065514 A1 | 3/2005 | Studer |
| 2005/0065515 A1 | 3/2005 | Jahng |
| 2005/0065516 A1 | 3/2005 | Jahng |
| 2005/0065517 A1 | 3/2005 | Chin |
| 2005/0070899 A1 | 3/2005 | Doubler et al. |
| 2005/0070901 A1 | 3/2005 | David |
| 2005/0080415 A1 | 4/2005 | Keyer et al. |
| 2005/0085812 A1 | 4/2005 | Sherman et al. |
| 2005/0085813 A1 | 4/2005 | Spitler et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096653 A1 | 5/2005 | Doubler et al. |
| 2005/0096654 A1 | 5/2005 | Lin |
| 2005/0107788 A1 | 5/2005 | Beaurain et al. |
| 2005/0113832 A1 | 5/2005 | Molz et al. |
| 2005/0113927 A1 | 5/2005 | Malek |
| 2005/0119658 A1 | 6/2005 | Ralph et al. |
| 2005/0124991 A1 | 6/2005 | Jahng |
| 2005/0131404 A1 | 6/2005 | Mazda et al. |
| 2005/0131405 A1 | 6/2005 | Molz et al. |
| 2005/0131406 A1 | 6/2005 | Reiley et al. |
| 2005/0131407 A1 | 6/2005 | Sicvol et al. |
| 2005/0131408 A1 | 6/2005 | Sicvol et al. |
| 2005/0131413 A1 | 6/2005 | O'Driscoll et al. |
| 2005/0131419 A1 | 6/2005 | McCord et al. |
| 2005/0137593 A1 | 6/2005 | Gray et al. |
| 2005/0137594 A1 | 6/2005 | Doubler et al. |
| 2005/0137597 A1 | 6/2005 | Butler et al. |
| 2005/0141986 A1 | 6/2005 | Flesher |
| 2005/0143737 A1 | 6/2005 | Pafford et al. |
| 2005/0143823 A1 | 6/2005 | Boyd et al. |
| 2005/0149020 A1 | 7/2005 | Jahng |
| 2005/0149023 A1 | 7/2005 | Ritland |
| 2005/0149036 A1 | 7/2005 | Varieur et al. |
| 2005/0149053 A1 | 7/2005 | Varieur et al. |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165400 A1 | 7/2005 | Fernandez |
| 2005/0171540 A1 | 8/2005 | Lim et al. |
| 2005/0171542 A1 | 8/2005 | Biedermann et al. |
| 2005/0171543 A1 | 8/2005 | Timm et al. |
| 2005/0171549 A1 | 8/2005 | Boehm et al. |
| 2005/0177154 A1 | 8/2005 | Moumene et al. |
| 2005/0177157 A1 | 8/2005 | Jahng |
| 2005/0177166 A1 | 8/2005 | Timm et al. |
| 2005/0182401 A1 | 8/2005 | Timm et al. |
| 2005/0182410 A1 | 8/2005 | Jackson |
| 2005/0187548 A1 | 8/2005 | Butler et al. |
| 2005/0187555 A1 | 8/2005 | Biedermann et al. |
| 2005/0192570 A1 | 9/2005 | Jackson |
| 2005/0192571 A1 | 9/2005 | Abdelgany |
| 2005/0192573 A1 | 9/2005 | Abdelgany et al. |

(56) References Cited

U.S. PATENT DOCUMENTS

| | | |
|---|---|---|
| 2005/0192579 A1 | 9/2005 | Jackson |
| 2005/0192580 A1 | 9/2005 | Dalton |
| 2005/0192589 A1 | 9/2005 | Raymond et al. |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Biedermann et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0215999 A1 | 9/2005 | Birkmeyer et al. |
| 2005/0216000 A1 | 9/2005 | Colleran et al. |
| 2005/0216001 A1 | 9/2005 | David |
| 2005/0216003 A1 | 9/2005 | Biedermann et al. |
| 2005/0228326 A1 | 10/2005 | Kalfas et al. |
| 2005/0228385 A1 | 10/2005 | Iott et al. |
| 2005/0228400 A1 | 10/2005 | Chao et al. |
| 2005/0228501 A1 | 10/2005 | Miller et al. |
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0234459 A1 | 10/2005 | Falahee et al. |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251139 A1 | 11/2005 | Roh |
| 2005/0251140 A1 | 11/2005 | Shaolian et al. |
| 2005/0251141 A1 | 11/2005 | Frigg et al. |
| 2005/0260058 A1 | 11/2005 | Cassagne |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267472 A1 | 12/2005 | Biedermann et al. |
| 2005/0267474 A1 | 12/2005 | Dalton |
| 2005/0267477 A1 | 12/2005 | Jackson |
| 2005/0267577 A1 | 12/2005 | Trieu |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0277931 A1 | 12/2005 | Sweeney et al. |
| 2005/0277934 A1 | 12/2005 | Vardiman |
| 2005/0278023 A1 | 12/2005 | Zwirkoski |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brookmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009775 A1 | 1/2006 | Dec et al. |
| 2006/0009780 A1 | 1/2006 | Foley et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0030850 A1 | 2/2006 | Keegan et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036254 A1 | 2/2006 | Lim |
| 2006/0036255 A1 | 2/2006 | Pond et al. |
| 2006/0036256 A1 | 2/2006 | Carl et al. |
| 2006/0036259 A1 | 2/2006 | Carl et al. |
| 2006/0036260 A1 | 2/2006 | Runco et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg et al. |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak et al. |
| 2006/0079898 A1 | 4/2006 | Ainsworth et al. |
| 2006/0079899 A1 | 4/2006 | Ritland |
| 2006/0079909 A1 | 4/2006 | Runco et al. |
| 2006/0084977 A1 | 4/2006 | Lieberman |
| 2006/0084980 A1 | 4/2006 | Melkent et al. |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom et al. |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0085070 A1 | 4/2006 | Kim |
| 2006/0089643 A1 | 4/2006 | Mujwid |
| 2006/0089644 A1 | 4/2006 | Felix |
| 2006/0089645 A1 | 4/2006 | Eckman |
| 2006/0089681 A1 | 4/2006 | Tumlinson et al. |
| 2006/0095035 A1 | 5/2006 | Jones et al. |
| 2006/0095037 A1 | 5/2006 | Jones et al. |
| 2006/0106380 A1 | 5/2006 | Colleran et al. |
| 2006/0106381 A1 | 5/2006 | Ferree et al. |
| 2006/0106383 A1 | 5/2006 | Biedermann et al. |
| 2006/0106394 A1 | 5/2006 | Colleran |
| 2006/0111714 A1 | 5/2006 | Foley |
| 2006/0111715 A1 | 5/2006 | Jackson |
| 2006/0116677 A1 | 6/2006 | Burd et al. |
| 2006/0122597 A1 | 6/2006 | Jones et al. |
| 2006/0122599 A1 | 6/2006 | Drewry et al. |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer et al. |
| 2006/0149229 A1 | 7/2006 | Kwak et al. |
| 2006/0149232 A1 | 7/2006 | Sasing |
| 2006/0149238 A1 | 7/2006 | Sherman et al. |
| 2006/0149241 A1 | 7/2006 | Richelsoph et al. |
| 2006/0149244 A1 | 7/2006 | Amrein et al. |
| 2006/0149251 A1 | 7/2006 | Ziolo et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |

(56) References Cited

U.S. PATENT DOCUMENTS

| | | |
|---|---|---|
| 2006/0166535 A1 | 7/2006 | Brumfield et al. |
| 2006/0167454 A1 | 7/2006 | Ludwig et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann et al. |
| 2006/0184180 A1 | 8/2006 | Augostino et al. |
| 2006/0189983 A1 | 8/2006 | Fallin et al. |
| 2006/0189984 A1 | 8/2006 | Fallin et al. |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200023 A1 | 9/2006 | Melkent et al. |
| 2006/0200128 A1 | 9/2006 | Mueller |
| 2006/0200130 A1 | 9/2006 | Hawkins et al. |
| 2006/0200131 A1 | 9/2006 | Chao et al. |
| 2006/0200132 A1 | 9/2006 | Chao et al. |
| 2006/0200135 A1 | 9/2006 | Sherman et al. |
| 2006/0200138 A1 | 9/2006 | Michelson |
| 2006/0200139 A1 | 9/2006 | Michelson |
| 2006/0200149 A1 | 9/2006 | Hoy et al. |
| 2006/0210494 A1 | 9/2006 | Rabiei et al. |
| 2006/0212033 A1 | 9/2006 | Rothman et al. |
| 2006/0212034 A1 | 9/2006 | Triplett et al. |
| 2006/0217713 A1 | 9/2006 | Serhan et al. |
| 2006/0217714 A1 | 9/2006 | Serhan et al. |
| 2006/0217715 A1 | 9/2006 | Serhan et al. |
| 2006/0217716 A1 | 9/2006 | Baker et al. |
| 2006/0229608 A1 | 10/2006 | Foster et al. |
| 2006/0229609 A1 | 10/2006 | Wang |
| 2006/0229612 A1 | 10/2006 | Rothman et al. |
| 2006/0229613 A1 | 10/2006 | Timm et al. |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz et al. |
| 2006/0241599 A1 | 10/2006 | Konieczynski et al. |
| 2006/0241600 A1 | 10/2006 | Ensign et al. |
| 2006/0241601 A1 | 10/2006 | Trautwein et al. |
| 2006/0241769 A1 | 10/2006 | Gordon et al. |
| 2006/0241771 A1 | 10/2006 | Gordon et al. |
| 2006/0247624 A1 | 11/2006 | Banouskou et al. |
| 2006/0247630 A1 | 11/2006 | Iott et al. |
| 2006/0247631 A1 | 11/2006 | Ahn et al. |
| 2006/0247632 A1 | 11/2006 | Winslow et al. |
| 2006/0247633 A1 | 11/2006 | Winslow et al. |
| 2006/0247635 A1 | 11/2006 | Gordon et al. |
| 2006/0247636 A1 | 11/2006 | Yuan et al. |
| 2006/0247637 A1 | 11/2006 | Colleran et al. |
| 2006/0247658 A1 | 11/2006 | Pond et al. |
| 2006/0247779 A1 | 11/2006 | Gordon et al. |
| 2006/0264933 A1 | 11/2006 | Baker et al. |
| 2006/0264934 A1 | 11/2006 | Fallin |
| 2006/0264935 A1 | 11/2006 | White |
| 2006/0264936 A1 | 11/2006 | Partin et al. |
| 2006/0264937 A1 | 11/2006 | White |
| 2006/0264940 A1 | 11/2006 | Hartmann |
| 2006/0264942 A1 | 11/2006 | Lim et al. |
| 2006/0264962 A1 | 11/2006 | Chin et al. |
| 2006/0269940 A1 | 11/2006 | Li et al. |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom et al. |
| 2006/0282076 A1 | 12/2006 | Labrom et al. |
| 2006/0282077 A1 | 12/2006 | Labrom et al. |
| 2006/0282078 A1 | 12/2006 | Labrom et al. |
| 2006/0282079 A1 | 12/2006 | Labrom et al. |
| 2006/0282080 A1 | 12/2006 | Albert et al. |
| 2006/0293657 A1 | 12/2006 | Hartmann |
| 2006/0293659 A1 | 12/2006 | Alvarez |
| 2006/0293663 A1 | 12/2006 | Walkenhorst et al. |
| 2006/0293665 A1 | 12/2006 | Shluzas |
| 2006/0293666 A1 | 12/2006 | Matthis et al. |
| 2006/0293693 A1 | 12/2006 | Farr et al. |
| 2007/0005062 A1 | 1/2007 | Lange et al. |
| 2007/0005063 A1 | 1/2007 | Bruneau et al. |
| 2007/0005137 A1 | 1/2007 | Kwak |
| 2007/0016188 A1 | 1/2007 | Boehm et al. |
| 2007/0016190 A1 | 1/2007 | Martinez et al. |
| 2007/0016193 A1 | 1/2007 | Ritland |
| 2007/0016194 A1 | 1/2007 | Shaolian et al. |
| 2007/0016198 A1 | 1/2007 | Boehm et al. |
| 2007/0016199 A1 | 1/2007 | Boehm et al. |
| 2007/0021750 A1 | 1/2007 | Shluzas et al. |
| 2007/0032123 A1 | 2/2007 | Timm et al. |
| 2007/0043355 A1 | 2/2007 | Bette et al. |
| 2007/0043356 A1 | 2/2007 | Timm et al. |
| 2007/0043357 A1 | 2/2007 | Kirschman |
| 2007/0043358 A1 | 2/2007 | Molz et al. |
| 2007/0043359 A1 | 2/2007 | Altarac et al. |
| 2007/0043364 A1 | 2/2007 | Cawley et al. |
| 2007/0049931 A1 | 3/2007 | Justis et al. |
| 2007/0049933 A1 | 3/2007 | Ahn et al. |
| 2007/0049936 A1 | 3/2007 | Colleran et al. |
| 2007/0055235 A1 | 3/2007 | Janowski et al. |
| 2007/0055236 A1 | 3/2007 | Hudgins et al. |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak et al. |
| 2007/0073290 A1 | 3/2007 | Boehm |
| 2007/0073291 A1 | 3/2007 | Cordaro et al. |
| 2007/0073293 A1 | 3/2007 | Martz et al. |
| 2007/0073294 A1 | 3/2007 | Chin et al. |
| 2007/0073405 A1 | 3/2007 | Verhulst et al. |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0093813 A1 | 4/2007 | Callahan et al. |
| 2007/0093814 A1 | 4/2007 | Callahan et al. |
| 2007/0093815 A1 | 4/2007 | Callahan et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093824 A1 | 4/2007 | Hestad et al. |
| 2007/0093826 A1 | 4/2007 | Hawkes et al. |
| 2007/0093827 A1 | 4/2007 | Warnick |
| 2007/0093828 A1 | 4/2007 | Abdou |
| 2007/0093831 A1 | 4/2007 | Abdelgany et al. |
| 2007/0093833 A1 | 4/2007 | Kuiper et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1 | 5/2007 | Strausbaugh et al. |
| 2007/0118124 A1 | 5/2007 | Biedermann et al. |
| 2007/0123862 A1 | 5/2007 | Warnick |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0129729 A1 | 6/2007 | Petit et al. |
| 2007/0129731 A1 | 6/2007 | Sicvol et al. |
| 2007/0135815 A1 | 6/2007 | Gerbec et al. |
| 2007/0156142 A1 | 7/2007 | Rezach et al. |
| 2007/0156237 A1 | 7/2007 | Kwak |
| 2007/0161986 A1 | 7/2007 | Levy |
| 2007/0161991 A1 | 7/2007 | Altarac et al. |

(56) References Cited

U.S. PATENT DOCUMENTS

| | | |
|---|---|---|
| 2007/0161994 A1 | 7/2007 | Lowery et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0167954 A1 | 7/2007 | Sicvol et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0233097 A1 | 10/2007 | Anderson et al. |
| 2007/0233155 A1 | 10/2007 | Lovell |
| 2007/0244481 A1 | 10/2007 | Timm |
| 2007/0250061 A1 | 10/2007 | Chin et al. |
| 2007/0260243 A1 | 11/2007 | Kagami |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270821 A1 | 11/2007 | Trieu et al. |
| 2007/0270830 A1 | 11/2007 | Morrison |
| 2007/0270831 A1 | 11/2007 | Dewey et al. |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0270869 A1 | 11/2007 | Young et al. |
| 2007/0276379 A1 | 11/2007 | Miller et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant et al. |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077136 A1 | 3/2008 | Triplett et al. |
| 2008/0077138 A1 | 3/2008 | Cohen et al. |
| 2008/0077139 A1 | 3/2008 | Landry et al. |
| 2008/0077143 A1 | 3/2008 | Shluzas |
| 2008/0086131 A1 | 4/2008 | Daly et al. |
| 2008/0086132 A1 | 4/2008 | Biedermann et al. |
| 2008/0091214 A1 | 4/2008 | Richelsoph |
| 2008/0097431 A1 | 4/2008 | Vessa |
| 2008/0097434 A1 | 4/2008 | Moumene et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114403 A1 | 5/2008 | Kuester et al. |
| 2008/0119849 A1 | 5/2008 | Beardsley et al. |
| 2008/0119850 A1 | 5/2008 | Sicvol et al. |
| 2008/0119857 A1 | 5/2008 | Potash et al. |
| 2008/0119858 A1 | 5/2008 | Potash |
| 2008/0125777 A1 | 5/2008 | Veldman et al. |
| 2008/0125787 A1 | 5/2008 | Doubler et al. |
| 2008/0132952 A1 | 6/2008 | Malandain et al. |
| 2008/0132957 A1 | 6/2008 | Matthis et al. |
| 2008/0140075 A1 | 6/2008 | Ensign et al. |
| 2008/0140076 A1 | 6/2008 | Jackson |
| 2008/0140133 A1 | 6/2008 | Allard et al. |
| 2008/0147122 A1 | 6/2008 | Jackson |
| 2008/0154279 A1 | 6/2008 | Schumacher et al. |
| 2008/0154307 A1 | 6/2008 | Colleran et al. |
| 2008/0161854 A1 | 7/2008 | Bae et al. |
| 2008/0161857 A1 | 7/2008 | Hestad et al. |
| 2008/0161859 A1 | 7/2008 | Nilsson |
| 2008/0161863 A1 | 7/2008 | Arnold et al. |
| 2008/0167687 A1 | 7/2008 | Colleran et al. |
| 2008/0172090 A1 | 7/2008 | Molz |
| 2008/0172091 A1 | 7/2008 | Anderson |
| 2008/0172096 A1 | 7/2008 | Hawkins |
| 2008/0177316 A1 | 7/2008 | Bergeron et al. |
| 2008/0177317 A1 | 7/2008 | Jackson |
| 2008/0177319 A1 | 7/2008 | Schwab |
| 2008/0177321 A1 | 7/2008 | Drewry et al. |
| 2008/0177322 A1 | 7/2008 | Davis et al. |
| 2008/0177327 A1 | 7/2008 | Malandain et al. |
| 2008/0177332 A1 | 7/2008 | Reiley et al. |
| 2008/0183212 A1 | 7/2008 | Veldman et al. |
| 2008/0183213 A1 | 7/2008 | Veldman et al. |
| 2008/0183215 A1 | 7/2008 | Altarac et al. |
| 2008/0183216 A1 | 7/2008 | Jackson |
| 2008/0183219 A1 | 7/2008 | Bertram |
| 2008/0183223 A1 | 7/2008 | Jeon et al. |
| 2008/0195100 A1 | 8/2008 | Capote et al. |
| 2008/0195153 A1 | 8/2008 | Thompson |
| 2008/0195155 A1 | 8/2008 | Hoffman et al. |
| 2008/0195159 A1 | 8/2008 | Kloss et al. |
| 2008/0200918 A1 | 8/2008 | Spitler et al. |
| 2008/0200956 A1 | 8/2008 | Beckwith et al. |
| 2008/0215095 A1 | 9/2008 | Biedermann et al. |
| 2008/0221620 A1 | 9/2008 | Krause |

(56) References Cited

U.S. PATENT DOCUMENTS

| | | |
|---|---|---|
| 2008/0221692 A1 | 9/2008 | Zucherman et al. |
| 2008/0228184 A1 | 9/2008 | Hestad |
| 2008/0228227 A1 | 9/2008 | Brown et al. |
| 2008/0228228 A1 | 9/2008 | Hestad et al. |
| 2008/0228229 A1 | 9/2008 | Walder et al. |
| 2008/0234691 A1 | 9/2008 | Schwab |
| 2008/0234734 A1 | 9/2008 | Walder et al. |
| 2008/0234736 A1 | 9/2008 | Trieu et al. |
| 2008/0234737 A1 | 9/2008 | Boschert |
| 2008/0234738 A1 | 9/2008 | Zylber et al. |
| 2008/0234739 A1 | 9/2008 | Hudgins et al. |
| 2008/0234744 A1 | 9/2008 | Zylber et al. |
| 2008/0234746 A1 | 9/2008 | Jahng et al. |
| 2008/0234756 A1 | 9/2008 | Sutcliffe et al. |
| 2008/0234759 A1 | 9/2008 | Marino |
| 2008/0243052 A1 | 10/2008 | Pond et al. |
| 2008/0243185 A1 | 10/2008 | Felix et al. |
| 2008/0243188 A1 | 10/2008 | Walder et al. |
| 2008/0243194 A1 | 10/2008 | Lotz et al. |
| 2008/0249570 A1 | 10/2008 | Carson et al. |
| 2008/0249576 A1 | 10/2008 | Hawkes et al. |
| 2008/0255617 A1 | 10/2008 | Cho et al. |
| 2008/0262546 A1 | 10/2008 | Calvosa et al. |
| 2008/0262548 A1 | 10/2008 | Lange et al. |
| 2008/0262551 A1 | 10/2008 | Rice et al. |
| 2008/0262552 A1 | 10/2008 | Kim |
| 2008/0262554 A1 | 10/2008 | Hayes et al. |
| 2008/0262556 A1 | 10/2008 | Jacofsky et al. |
| 2008/0269742 A1 | 10/2008 | Levy et al. |
| 2008/0269804 A1 | 10/2008 | Holt |
| 2008/0269805 A1 | 10/2008 | Dekutoski et al. |
| 2008/0269809 A1 | 10/2008 | Garamszegi |
| 2008/0275456 A1 | 11/2008 | Vonwiller et al. |
| 2008/0275504 A1 | 11/2008 | Bonin et al. |
| 2008/0287994 A1 | 11/2008 | Perez-Cruet et al. |
| 2008/0288002 A1 | 11/2008 | Crall et al. |
| 2008/0300630 A1 | 12/2008 | Bonnema et al. |
| 2008/0300633 A1 | 12/2008 | Jackson |
| 2008/0306513 A1 | 12/2008 | Winslow et al. |
| 2008/0306525 A1 | 12/2008 | Mitchell et al. |
| 2008/0306528 A1 | 12/2008 | Winslow et al. |
| 2008/0306533 A1 | 12/2008 | Winslow et al. |
| 2008/0306536 A1 | 12/2008 | Frigg et al. |
| 2008/0306539 A1 | 12/2008 | Cain et al. |
| 2008/0306540 A1 | 12/2008 | Mitchell et al. |
| 2008/0306543 A1 | 12/2008 | Cain et al. |
| 2008/0306545 A1 | 12/2008 | Winslow et al. |
| 2008/0312655 A1 | 12/2008 | Kirschman et al. |
| 2008/0312692 A1 | 12/2008 | Brennan et al. |
| 2008/0312694 A1 | 12/2008 | Peterman et al. |
| 2008/0312696 A1 | 12/2008 | Butters et al. |
| 2008/0312701 A1 | 12/2008 | Butters et al. |
| 2008/0312703 A1 | 12/2008 | Hestad et al. |
| 2008/0312704 A1 | 12/2008 | Hestad et al. |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0005817 A1 | 1/2009 | Friedrich et al. |
| 2009/0012567 A1 | 1/2009 | Biedermann et al. |
| 2009/0018583 A1 | 1/2009 | Song et al. |
| 2009/0018591 A1 | 1/2009 | Hawkes et al. |
| 2009/0024165 A1 | 1/2009 | Ferree |
| 2009/0024169 A1 | 1/2009 | Triplett et al. |
| 2009/0030457 A1 | 1/2009 | Janowski et al. |
| 2009/0030464 A1 | 1/2009 | Hestad et al. |
| 2009/0030465 A1 | 1/2009 | Altarac et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0048601 A1 | 2/2009 | Forton et al. |
| 2009/0048631 A1 | 2/2009 | Bhatnagar et al. |
| 2009/0054932 A1 | 2/2009 | Butler et al. |
| 2009/0062860 A1 | 3/2009 | Frasier et al. |
| 2009/0062865 A1 | 3/2009 | Schumacher |
| 2009/0062867 A1 | 3/2009 | Schumacher |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082811 A1 | 3/2009 | Stad et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088782 A1 | 4/2009 | Moumene et al. |
| 2009/0088799 A1 | 4/2009 | Yeh |
| 2009/0088803 A1 | 4/2009 | Justis et al. |
| 2009/0088807 A1 | 4/2009 | Castaneda et al. |
| 2009/0093820 A1 | 4/2009 | Trieu et al. |
| 2009/0093843 A1 | 4/2009 | Lemoine et al. |
| 2009/0093845 A1 | 4/2009 | Hestad et al. |
| 2009/0093846 A1 | 4/2009 | Hestad |
| 2009/0099599 A1 | 4/2009 | Biedermann et al. |
| 2009/0099606 A1 | 4/2009 | Hestad et al. |
| 2009/0099607 A1 | 4/2009 | Fallin et al. |
| 2009/0099608 A1 | 4/2009 | Szczesny |
| 2009/0105760 A1 | 4/2009 | Frey |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0112265 A1 | 4/2009 | Hudgins et al. |
| 2009/0112266 A1 | 4/2009 | Weng et al. |
| 2009/0112267 A1 | 4/2009 | Atkinson et al. |
| 2009/0118767 A1 | 5/2009 | Hestad et al. |
| 2009/0118772 A1 | 5/2009 | Diederich et al. |
| 2009/0125063 A1 | 5/2009 | Panjabi |
| 2009/0131981 A1 | 5/2009 | White |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143828 A1 | 6/2009 | Stad et al. |
| 2009/0143829 A1 | 6/2009 | Shluzas |
| 2009/0149885 A1 | 6/2009 | Durward et al. |
| 2009/0149887 A1 | 6/2009 | Schlaepfer et al. |
| 2009/0149892 A1 | 6/2009 | Stad et al. |
| 2009/0163901 A1 | 6/2009 | Fisher et al. |
| 2009/0163953 A1 | 6/2009 | Biedermann et al. |
| 2009/0163954 A1 | 6/2009 | Kwak |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0171392 A1 | 7/2009 | Garcia-Bengochea et al. |
| 2009/0171395 A1 | 7/2009 | Jeon et al. |
| 2009/0177232 A1 | 7/2009 | Kiester |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198281 A1 | 8/2009 | Rice et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0221877 A1 | 9/2009 | Woods |
| 2009/0228045 A1 | 9/2009 | Hayes et al. |
| 2009/0240286 A1 | 9/2009 | Friedrich et al. |
| 2009/0240287 A1 | 9/2009 | Cunliffe et al. |
| 2009/0240292 A1 | 9/2009 | Butler et al. |
| 2009/0248030 A1 | 10/2009 | Butler et al. |
| 2009/0248075 A1 | 10/2009 | Ogilvie et al. |
| 2009/0248077 A1 | 10/2009 | Johns |
| 2009/0248081 A1 | 10/2009 | LeHuec et al. |
| 2009/0248083 A1 | 10/2009 | Patterson et al. |
| 2009/0248088 A1 | 10/2009 | Biedermann |
| 2009/0254123 A1 | 10/2009 | Pafford et al. |
| 2009/0254125 A1 | 10/2009 | Predick |
| 2009/0259254 A1 | 10/2009 | Pisharodi |
| 2009/0259257 A1 | 10/2009 | Prevost |
| 2009/0259258 A1 | 10/2009 | Perez-Cruet et al. |
| 2009/0264895 A1 | 10/2009 | Gasperut et al. |

(56) References Cited

U.S. PATENT DOCUMENTS

| | | |
|---|---|---|
| 2009/0264896 A1 | 10/2009 | Biedermann et al. |
| 2009/0264930 A1 | 10/2009 | McBride |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0270920 A1 | 10/2009 | Douget et al. |
| 2009/0270921 A1 | 10/2009 | Krause |
| 2009/0270922 A1 | 10/2009 | Biedermann et al. |
| 2009/0275981 A1 | 11/2009 | Abdelgany et al. |
| 2009/0275983 A1 | 11/2009 | Veldman et al. |
| 2009/0275986 A1 | 11/2009 | Prevost et al. |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287250 A1 | 11/2009 | Molz, IV et al. |
| 2009/0287251 A1 | 11/2009 | Bae et al. |
| 2009/0287252 A1 | 11/2009 | Marik et al. |
| 2009/0287253 A1 | 11/2009 | Felix et al. |
| 2009/0299411 A1 | 12/2009 | Laskowitz et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0318968 A1 | 12/2009 | Duggal et al. |
| 2009/0326582 A1 | 12/2009 | Songer et al. |
| 2009/0326583 A1 | 12/2009 | Moumene et al. |
| 2009/0326586 A1 | 12/2009 | Duarte |
| 2009/0326587 A1 | 12/2009 | Matthis et al. |
| 2010/0004692 A1 | 1/2010 | Biedermann et al. |
| 2010/0004695 A1 | 1/2010 | Stad et al. |
| 2010/0010540 A1 | 1/2010 | Park |
| 2010/0010544 A1 | 1/2010 | Fallin et al. |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030283 A1 | 2/2010 | King et al. |
| 2010/0036420 A1 | 2/2010 | Kalfas et al. |
| 2010/0036422 A1 | 2/2010 | Flynn et al. |
| 2010/0036423 A1 | 2/2010 | Hayes et al. |
| 2010/0036424 A1 | 2/2010 | Fielding et al. |
| 2010/0036425 A1 | 2/2010 | Barrus et al. |
| 2010/0036443 A1 | 2/2010 | Hutton et al. |
| 2010/0042149 A1 | 2/2010 | Chao et al. |
| 2010/0042152 A1 | 2/2010 | Semler et al. |
| 2010/0042155 A1 | 2/2010 | Biedermann et al. |
| 2010/0042156 A1 | 2/2010 | Harms et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063544 A1 | 3/2010 | Butler |
| 2010/0063545 A1 | 3/2010 | Richelsoph |
| 2010/0063547 A1 | 3/2010 | Morin et al. |
| 2010/0063550 A1 | 3/2010 | Felix et al. |
| 2010/0063551 A1 | 3/2010 | Richelsoph |
| 2010/0063552 A1 | 3/2010 | Chin et al. |
| 2010/0063553 A1 | 3/2010 | Warnick |
| 2010/0069919 A1 | 3/2010 | Carls et al. |
| 2010/0069963 A1 | 3/2010 | Eckman |
| 2010/0069964 A1 | 3/2010 | Lechmann |
| 2010/0069969 A1 | 3/2010 | Ampuero et al. |
| 2010/0087858 A1 | 4/2010 | Abdou |
| 2010/0087861 A1 | 4/2010 | Lechmann et al. |
| 2010/0087862 A1 | 4/2010 | Biedermann et al. |
| 2010/0087863 A1 | 4/2010 | Biedermann et al. |
| 2010/0087864 A1 | 4/2010 | Klein et al. |
| 2010/0087865 A1 | 4/2010 | Biedermann et al. |
| 2010/0088782 A1 | 4/2010 | Oswald et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1 | 4/2010 | Hammer et al. |
| 2010/0094352 A1 | 4/2010 | Iott et al. |
| 2010/0094353 A1 | 4/2010 | Shim et al. |
| 2010/0100136 A1 | 4/2010 | Won et al. |
| 2010/0100137 A1 | 4/2010 | Justis et al. |
| 2010/0106189 A1 | 4/2010 | Miller |
| 2010/0114108 A1 | 5/2010 | Strauss |
| 2010/0114170 A1 | 5/2010 | Barrus et al. |
| 2010/0114171 A1 | 5/2010 | Boachie-Adjei et al. |
| 2010/0114179 A1 | 5/2010 | Moore et al. |
| 2010/0114180 A1 | 5/2010 | Rock et al. |
| 2010/0114182 A1 | 5/2010 | Wilcox et al. |
| 2010/0121385 A1 | 5/2010 | Blain et al. |
| 2010/0121386 A1 | 5/2010 | Peultier et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137915 A1 | 6/2010 | Anderson et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1 | 6/2010 | Walsh et al. |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0168803 A1 | 7/2010 | Hestad et al. |
| 2010/0174322 A1 | 7/2010 | Abdelgany et al. |
| 2010/0179602 A1 | 7/2010 | Dauster et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0204736 A1 | 8/2010 | Biedermann et al. |
| 2010/0222822 A1 | 9/2010 | Farris et al. |
| 2010/0222828 A1 | 9/2010 | Stad et al. |
| 2010/0228293 A1 | 9/2010 | Courtney et al. |
| 2010/0234891 A1 | 9/2010 | Freeman et al. |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0262196 A1 | 10/2010 | Barrus et al. |
| 2010/0292742 A1 | 11/2010 | Stad et al. |
| 2011/0004256 A1 | 1/2011 | Biedermann et al. |
| 2011/0046683 A1 | 2/2011 | Biedermann et al. |
| 2011/0060344 A1 | 3/2011 | Sicvol et al. |
| 2011/0060374 A1 | 3/2011 | Sicvol et al. |
| 2011/0093015 A1 | 4/2011 | Ramsay et al. |
| 2011/0106174 A1 | 5/2011 | Rezach |
| 2011/0106175 A1 | 5/2011 | Rezach |
| 2011/0166610 A1 | 7/2011 | Altarac et al. |
| 2011/0178560 A1 | 7/2011 | Butler et al. |
| 2011/0184469 A1 | 7/2011 | Ballard et al. |
| 2011/0184471 A1 | 7/2011 | Foley et al. |
| 2011/0184473 A1 | 7/2011 | Garcia-Bengochea et al. |
| 2011/0190822 A1 | 8/2011 | Spitler et al. |
| 2011/0202094 A1 | 8/2011 | Pereira et al. |
| 2011/0202095 A1 | 8/2011 | Semler et al. |
| 2011/0263945 A1 | 10/2011 | Peterson et al. |
| 2011/0313460 A1 | 12/2011 | McLean et al. |
| 2011/0313463 A1 | 12/2011 | McLean |
| 2011/0313471 A1 | 12/2011 | McLean et al. |
| 2012/0071886 A1 | 3/2012 | Jackson |
| 2012/0232598 A1 | 9/2012 | Hestad et al. |
| 2012/0239151 A1 | 9/2012 | Ulrich, Jr. et al. |
| 2013/0296949 A1 | 11/2013 | Sicvol et al. |
| 2013/0304130 A1 | 11/2013 | Jackson |
| 2014/0031872 A1 | 1/2014 | Jackson |
| 2014/0222077 A1 | 8/2014 | Jackson |
| 2014/0222082 A1 | 8/2014 | Jackson |
| 2014/0222090 A1 | 8/2014 | Jackson |
| 2014/0236243 A1 | 8/2014 | Jackson |
| 2015/0080957 A1 | 3/2015 | Jackson |

(56) References Cited

U.S. PATENT DOCUMENTS

| | | | |
|---|---|---|---|
| 2015/0080962 A1 | 3/2015 | Jackson |
| 2015/0080965 A1 | 3/2015 | Jackson |
| 2015/0080974 A1 | 3/2015 | Jackson |
| 2015/0142060 A1 | 5/2015 | Jackson |
| 2015/0150606 A1 | 6/2015 | Jackson |
| 2015/0182258 A1 | 7/2015 | Jackson |
| 2015/0272631 A1 | 10/2015 | Jackson |
| 2016/0015433 A1 | 1/2016 | Jackson |
| 2016/0074077 A1 | 3/2016 | Jackson |
| 2017/0156761 A1 | 6/2017 | Sicvol et al. |
| 2017/0156762 A1 | 6/2017 | Sicvol et al. |
| 2018/0085146 A1 | 3/2018 | Sicvol et al. |

FOREIGN PATENT DOCUMENTS

| | | |
|---|---|---|
| DE | 26 49 042 B1 | 1/1978 |
| DE | 26 49 042 C2 | 9/1978 |
| DE | 29 03 342 A1 | 7/1980 |
| DE | 34 34 807 A1 | 12/1985 |
| DE | 34 34 807 C2 | 7/1987 |
| DE | 36 39 810 A1 | 5/1988 |
| DE | 37 11 013 C1 | 6/1988 |
| DE | 89 15 443 U1 | 6/1990 |
| DE | 90 06 568 U1 | 10/1990 |
| DE | 39 16 198 A1 | 11/1990 |
| DE | 92 02 745 U1 | 4/1992 |
| DE | 39 16 198 C2 | 7/1992 |
| DE | 43 07 576 C1 | 4/1994 |
| DE | 94 03 231 U1 | 4/1994 |
| DE | 42 39 716 C1 | 8/1994 |
| DE | 44 25 392 A1 | 11/1995 |
| DE | 195 07 141 A1 | 9/1996 |
| DE | 195 09 331 A1 | 9/1996 |
| DE | 36 39 810 C2 | 4/1998 |
| DE | 298 06 563 U1 | 6/1998 |
| DE | 298 10 798 U1 | 10/1999 |
| DE | 199 12 364 A1 | 10/2000 |
| DE | 199 51 145 A1 | 5/2001 |
| DE | 100 27 988 A1 | 1/2002 |
| DE | 202 07 850 U1 | 10/2002 |
| DE | 101 36 129 A1 | 2/2003 |
| DE | 101 57 969 C1 | 2/2003 |
| DE | 100 27 988 C2 | 8/2003 |
| DE | 102 36 691 A1 | 2/2004 |
| DE | 199 12 364 B4 | 10/2004 |
| DE | 10 2007 055 745 A1 | 7/2008 |
| EP | 0 242 708 A2 | 10/1987 |
| EP | 0 283 373 A1 | 9/1988 |
| EP | 0 328 883 A2 | 8/1989 |
| EP | 0 330 881 A1 | 9/1989 |
| EP | 0 346 521 A1 | 12/1989 |
| EP | 0 348 272 A1 | 12/1989 |
| EP | 0 392 927 A2 | 10/1990 |
| EP | 0 441 729 A1 | 8/1991 |
| EP | 0 465 158 A2 | 1/1992 |
| EP | 0 528 706 A1 | 2/1993 |
| EP | 0 324 022 B1 | 9/1993 |
| EP | 0 572 790 A1 | 12/1993 |
| EP | 0 379 551 B1 | 2/1994 |
| EP | 0 614 649 A1 | 9/1994 |
| EP | 0 667 127 A1 | 8/1995 |
| EP | 0 669 109 A1 | 8/1995 |
| EP | 0 677 277 A2 | 10/1995 |
| EP | 0 452 451 B1 | 6/1996 |
| EP | 0 771 635 A2 | 5/1997 |
| EP | 0 836 835 A2 | 4/1998 |
| EP | 0 870 474 A1 | 10/1998 |
| EP | 0 885 598 A2 | 12/1998 |
| EP | 1 090 595 A2 | 4/2001 |
| EP | 1 121 902 A2 | 8/2001 |
| EP | 1 133 951 A2 | 9/2001 |
| EP | 1 090 595 A3 | 11/2001 |
| EP | 1 190 678 A2 | 3/2002 |
| EP | 1 210 914 A1 | 6/2002 |
| EP | 1 190 678 A3 | 3/2003 |
| EP | 1 332 722 A1 | 8/2003 |
| EP | 1 133 951 A3 | 11/2003 |
| EP | 1 570 795 A1 | 9/2005 |
| EP | 1 579 816 A1 | 9/2005 |
| EP | 1 634 537 A1 | 3/2006 |
| EP | 1 925 263 A1 | 5/2008 |
| EP | 2 082 709 A1 | 7/2009 |
| FR | 2 624 720 A1 | 6/1989 |
| FR | 2 659 546 A1 | 9/1991 |
| FR | 2717370 A1 | 9/1995 |
| FR | 2718946 A1 | 10/1995 |
| FR | 2729291 A1 | 7/1996 |
| FR | 2796545 A1 | 1/2001 |
| FR | 2799949 A1 | 4/2001 |
| FR | 2814936 A1 | 4/2002 |
| FR | 2846223 A1 | 4/2004 |
| FR | 2856578 A1 | 12/2004 |
| FR | 2857850 A1 | 1/2005 |
| FR | 2865373 A1 | 7/2005 |
| FR | 2865375 A1 | 7/2005 |
| FR | 2865377 A1 | 7/2005 |
| FR | 2865378 A1 | 7/2005 |
| FR | 2925288 A1 | 6/2009 |
| GB | 522747 A | 6/1940 |
| GB | 1 519 139 A | 7/1978 |
| GB | 2 365 345 A | 2/2002 |
| GB | 2 382 304 A | 5/2003 |
| JP | 64-076847 A | 3/1989 |
| JP | 10-277070 A | 10/1998 |
| JP | 3061617 B1 | 7/2000 |
| JP | 2000-325358 A | 11/2000 |
| SU | 313538 A3 | 10/1971 |
| WO | 89/00028 A1 | 1/1989 |
| WO | 89/12431 A1 | 12/1989 |
| WO | 90/00377 A1 | 1/1990 |
| WO | 91/06254 A1 | 5/1991 |
| WO | 91/16020 A1 | 10/1991 |
| WO | 92/03100 A1 | 3/1992 |
| WO | 92/20294 A1 | 11/1992 |
| WO | 93/11715 A1 | 6/1993 |
| WO | 93/21848 A1 | 11/1993 |
| WO | 94/10927 A1 | 5/1994 |
| WO | 94/10944 A1 | 5/1994 |
| WO | 94/14384 A2 | 7/1994 |
| WO | 94/26191 A1 | 11/1994 |
| WO | 94/28824 A2 | 12/1994 |
| WO | 95/01132 A1 | 1/1995 |
| WO | 95/13755 A1 | 5/1995 |
| WO | 95/13756 A1 | 5/1995 |
| WO | 95/14437 A1 | 6/1995 |
| WO | 95/31947 A1 | 11/1995 |
| WO | 95/35067 A2 | 12/1995 |
| WO | 96/06576 A1 | 3/1996 |
| WO | 1996021396 A1 | 7/1996 |
| WO | 96/28105 A1 | 9/1996 |
| WO | 96/28118 A1 | 9/1996 |
| WO | 96/41582 A1 | 12/1996 |
| WO | 97/14368 A1 | 4/1997 |
| WO | 97/27812 A1 | 8/1997 |
| WO | 9730666 A2 | 8/1997 |
| WO | 98/01091 A1 | 1/1998 |
| WO | 98/12977 A1 | 4/1998 |
| WO | 98/15233 A1 | 4/1998 |
| WO | 98/25534 A1 | 6/1998 |
| WO | 98/32386 A1 | 7/1998 |
| WO | 98/34554 A1 | 8/1998 |
| WO | 98/32924 A2 | 9/1998 |
| WO | 99/01509 A1 | 1/1999 |
| WO | 99/05980 A1 | 2/1999 |
| WO | 1999015097 A2 | 4/1999 |
| WO | 99/26549 A1 | 6/1999 |
| WO | 99/38463 A2 | 8/1999 |
| WO | 99/47083 A1 | 9/1999 |
| WO | 00/22997 A1 | 4/2000 |
| WO | 00/27297 A1 | 5/2000 |
| WO | 00/44288 A1 | 8/2000 |
| WO | 00/65268 A1 | 11/2000 |
| WO | 00/66045 A1 | 11/2000 |
| WO | 01/01873 A1 | 1/2001 |

(56) References Cited

FOREIGN PATENT DOCUMENTS

| | | |
|---|---|---|
| WO | 01/10317 A1 | 2/2001 |
| WO | 01/15612 A1 | 3/2001 |
| WO | 01/28435 A1 | 4/2001 |
| WO | 01/28436 A1 | 4/2001 |
| WO | 01/45576 A1 | 6/2001 |
| WO | 01/49191 A1 | 7/2001 |
| WO | 01/67972 A2 | 9/2001 |
| WO | 01/67974 A1 | 9/2001 |
| WO | 02/34150 A2 | 5/2002 |
| WO | 02/054966 A2 | 7/2002 |
| WO | 02/069854 A1 | 9/2002 |
| WO | 02/102259 A2 | 12/2002 |
| WO | 03/007828 A1 | 1/2003 |
| WO | 03/026523 A1 | 4/2003 |
| WO | 03/028566 A1 | 4/2003 |
| WO | 03/047442 A1 | 6/2003 |
| WO | 03/068088 A1 | 8/2003 |
| WO | 2004/022108 A2 | 3/2004 |
| WO | 2004/041100 A1 | 5/2004 |
| WO | 2004/075778 A2 | 9/2004 |
| WO | 2004/089245 A2 | 10/2004 |
| WO | 2004/098452 A2 | 11/2004 |
| WO | 2004/107997 A2 | 12/2004 |
| WO | 2005/000136 A1 | 1/2005 |
| WO | 2005/000137 A1 | 1/2005 |
| WO | 2005/013839 A2 | 2/2005 |
| WO | 2005/018466 A2 | 3/2005 |
| WO | 2005/020829 A1 | 3/2005 |
| WO | 2005/030068 A1 | 4/2005 |
| WO | 2005/041799 A1 | 5/2005 |
| WO | 2005/065374 A2 | 7/2005 |
| WO | 2005/065375 A2 | 7/2005 |
| WO | 2005/072632 A1 | 8/2005 |
| WO | 2005/082262 A2 | 9/2005 |
| WO | 2005/087121 A1 | 9/2005 |
| WO | 2005/099400 A2 | 10/2005 |
| WO | 2005/102195 A1 | 11/2005 |
| WO | 2005/104969 A1 | 11/2005 |
| WO | 2006/005198 A1 | 1/2006 |
| WO | 2006/012088 A1 | 2/2006 |
| WO | 2006/017616 A1 | 2/2006 |
| WO | 2006/020530 A2 | 2/2006 |
| WO | 2006/028537 A2 | 3/2006 |
| WO | 2006/042188 A2 | 4/2006 |
| WO | 2006/045094 A2 | 4/2006 |
| WO | 2006/047711 A2 | 5/2006 |
| WO | 2006/066685 A1 | 6/2006 |
| WO | 2006/079531 A1 | 8/2006 |
| WO | 2006/086537 A2 | 8/2006 |
| WO | 2006/096240 A1 | 9/2006 |
| WO | 2006/096351 A1 | 9/2006 |
| WO | 2006/104874 A2 | 10/2006 |
| WO | 2006/110463 A1 | 10/2006 |
| WO | 2006/116662 A1 | 11/2006 |
| WO | 2006/119241 A2 | 11/2006 |
| WO | 2006/119447 A1 | 11/2006 |
| WO | 2007/002409 A2 | 1/2007 |
| WO | 2007/038350 A2 | 4/2007 |
| WO | 2007/040750 A1 | 4/2007 |
| WO | 2007/040888 A2 | 4/2007 |
| WO | 2007/041702 A2 | 4/2007 |
| WO | 2007/044705 A2 | 4/2007 |
| WO | 2007/053566 A2 | 5/2007 |
| WO | 2007/060534 A2 | 5/2007 |
| WO | 2007075454 A1 | 7/2007 |
| WO | 2007/087628 A1 | 8/2007 |
| WO | 2007/090021 A1 | 8/2007 |
| WO | 2007/092056 A1 | 8/2007 |
| WO | 2007/092870 A2 | 8/2007 |
| WO | 2007/097905 A2 | 8/2007 |
| WO | 2007/118045 A1 | 10/2007 |
| WO | 2007/121271 A2 | 10/2007 |
| WO | 2007/123920 A2 | 11/2007 |
| WO | 2007/124222 A1 | 11/2007 |
| WO | 2007/124249 A1 | 11/2007 |
| WO | 2007/127595 A2 | 11/2007 |
| WO | 2007/127604 A2 | 11/2007 |
| WO | 2007/130835 A2 | 11/2007 |
| WO | 2007/130840 A1 | 11/2007 |
| WO | 2007/130941 A2 | 11/2007 |
| WO | 2007/138270 A2 | 12/2007 |
| WO | 2007/146032 A2 | 12/2007 |
| WO | 2008/005740 A1 | 1/2008 |
| WO | 2008/006098 A2 | 1/2008 |
| WO | 2008/036975 A2 | 3/2008 |
| WO | 2008/039777 A2 | 4/2008 |
| WO | 2008/042948 A2 | 4/2008 |
| WO | 2008/045210 A2 | 4/2008 |
| WO | 2008/048923 A2 | 4/2008 |
| WO | 2008/069420 A1 | 6/2008 |
| WO | 2008/070716 A2 | 6/2008 |
| WO | 2008/078163 A2 | 7/2008 |
| WO | 2008/082737 A2 | 7/2008 |
| WO | 2008/088731 A1 | 7/2008 |
| WO | 2008/088990 A2 | 7/2008 |
| WO | 2008/089075 A1 | 7/2008 |
| WO | 2008/100590 A1 | 8/2008 |
| WO | 2008/118295 A2 | 10/2008 |
| WO | 2008/119006 A1 | 10/2008 |
| WO | 2008/124772 A1 | 10/2008 |
| WO | 2008/134703 A2 | 11/2008 |
| WO | 2008/140756 A2 | 11/2008 |
| WO | 2008/157589 A1 | 12/2008 |
| WO | 2009/006225 A2 | 1/2009 |
| WO | 2009/011845 A1 | 1/2009 |
| WO | 2009/015100 A2 | 1/2009 |
| WO | 2009/029928 A1 | 3/2009 |
| WO | 2009/036541 A2 | 3/2009 |
| WO | 2009/055407 A1 | 4/2009 |
| WO | 2009/152302 A1 | 12/2009 |
| WO | 2009/155360 A2 | 12/2009 |
| WO | 2010/018316 A1 | 2/2010 |
| WO | 2010/018317 A1 | 2/2010 |
| WO | 2010/019704 A1 | 2/2010 |
| WO | 2010/019857 A2 | 2/2010 |
| WO | 2010/030916 A2 | 3/2010 |
| WO | 2010/045383 A2 | 4/2010 |
| WO | 2010/065648 A1 | 6/2010 |

OTHER PUBLICATIONS

\*\*[No Author Listed] Ltr to Robert Malone from Dept. of Health & Human Services, Jun. 20, 2002 regarding Forex Corporation OPTIMA(TM) Devices 510(k) Summary, 5 paqes.
\*\*[No Author Listed] OPTIMA™ Spinal system Surgical Technique Brochure, pp. 1-17, 2005.
\*\*[No Author Listed] U&I Corporation Thoracolumbar Spine Optima Spinal System from website <www.uandi.co.kr>, pp. 1-2, Nov. 10, 2005.
\*\*[No Author Listed] XIA(TM) Spinal System Brochure, Stryker®, Howmedica Osteonics, pp. 1-7, Stryker Corporation, Rutherford, NJ, Jul. 1999.
\*\*Ebara, et al., A New System for the Anterio Restoration and Fixation of Thoracic Spinal Deformities Using an Andoscopic Approach; Spine Apr. 1, 2000; pp. 876-883; vol. 25(7).
\*\*Glazer, et al., Biomechanical analysis of Multilevel Fixation Methods in the Lumbar Spine; Spine Jan. 15, 1997; pp. 171-182; vol. 22(2).
\*\*Jeanneret, Posterior Rod System of the Cervical Spine: A New Implant Allowing Optimal Screw Insertion, Eur. Spine J., 1996; pp. 350-356, 5(5): Springer-Verlag.
\*\*Kaneda, et al., New Anterior Instrumentation for the Management of Thoracolumbar and Lumbar Scoliosis; Spine May 15, 1996; pp. 1250-1281; vol. 21(10).
\*\*Porter, Lascoe Nelson, Machineshop Operations and Setups, American Technical Society, 1973, pp. 380, 386 and 388 including redacted version.
\*\*Shapiro, et al., Spinal Instrumentation With a Low Complication Rate; Surg. Neurol. Dec. 1997; pp. 566-574; vol. 48(6), Elsevier Science.
\*\*Viau, et al., Thoracic Pedicle Screw Instrumentation Using the

(56) References Cited

OTHER PUBLICATIONS

"Funnell Technique"; J. Spinal Discord. Tech. Dec. 2002; pp. 450-453; vol. 15(6).

**Walker, J.R., Machining Fundamentals: Fundamentals Basic to Industry, The Goodheart-Wilcox Co., Inc., 1981, pp. 2, 179-186, including redacted version.

[No Author Listed] Brochure of Spinal Concepts, an Abbott Laboratories Company, PathFinder, Minimally Invasive Pedicle Fixation System, Publication Date : Nov. 2003. , 4 pages.

[No Author Listed] Brochure of Spinal Concepts, InCompass, Thoracolumbar Fixation System, Publication Date : Oct. 2003., 4 pages.

[No Author Listed] Brochure of Spinal Concepts, PathFinder, Minimally Invasive Pedicle Fixation System, Publication Date: May 2003., 4 pages.

[No Author Listed] Brochure of Spinal Concepts, Surgical Technique, InCompass, Thoracolumbar Fixation System, Publication Date : Oct. 2003., 18 pages.

[No Author Listed] Claris Instrumentation, Brochure, Eurosurgical Ltd., pub. 1997. , 6 pages.

[No Author Listed] EBI Omega 21(TM), Versatile System Adapts to Virtually Any Anatomical Need, Brochure, EBI, L.P., pub. 1999. , 1 page.

[No Author Listed] SDRS (TM) Surgical Dynamics Rod System, Brochure, Surgical Dynamics, Inc., pub. 1998-99. , 11 pages.

[No Author Listed] Spiral Radius 90D (TM), Brochure of Tyco/Healthcare/Surgical Dynamics, Inc., Publication Date: Sep. 2001, pp. 1-8.

[No Author Listed] Surgical Technique, Expedium (TM) Spine System, Brochure of DePuy Spine, Inc., Published 2004, pp. 1-36.

[No Author Listed] The Rod Plate System, Brochure, Stryker Spine, pub. Oct. 1999. , 6 pages.

[No Author Listed] Versalok (R) Low Back Fixation System, Technical Monograph, Brochure, Wright Medical Technology, Inc., publ. 1997. , 6 pages.

[No Author Listed] VLS (TM) System Variable Locking Screw, Brochure, Interpore Cross International, 1999. , 4 pages.

Davis, R.J., MD, FACS, et al., Brochure of Zimmer Spine, Inc., Dynesys (R) LIS Less Invasive Surgery, The Dynamic Stabilization System, Publication Date: 2005 , 23 pages.

Khoo, L.T., MD, et al., Minimally Invasive Posterior Spinal Decompression and Fusion Procedures, Brochure of SpineLine, Current Concepts, Publication Date: Sep./Oct. 2003, pp. 9-18.

Simmons, E.H., MD, et al., Brochure of Sofamor Danek the Spine Specialist, TSRH, Pedicle Screw Spinal System, Publication Date : Jan. 23, 1995. , 27 pages.

* cited by examiner

FIG. 18A
FIG. 18B
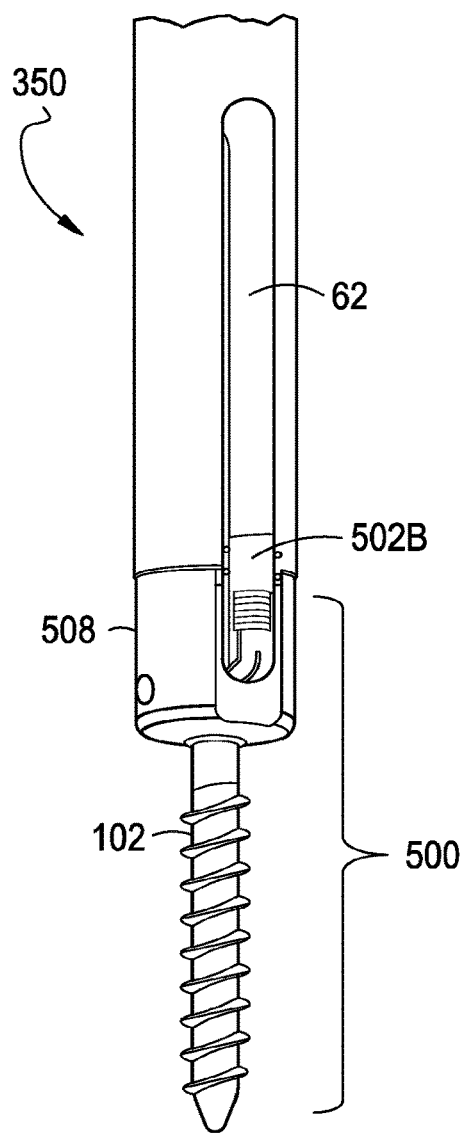
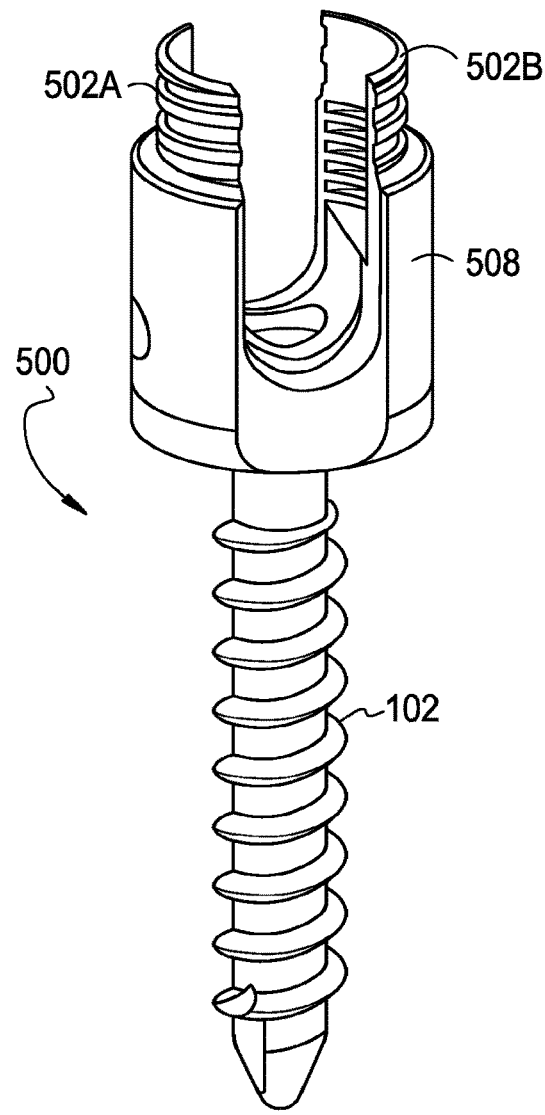

FIG. 23A
FIG. 23B
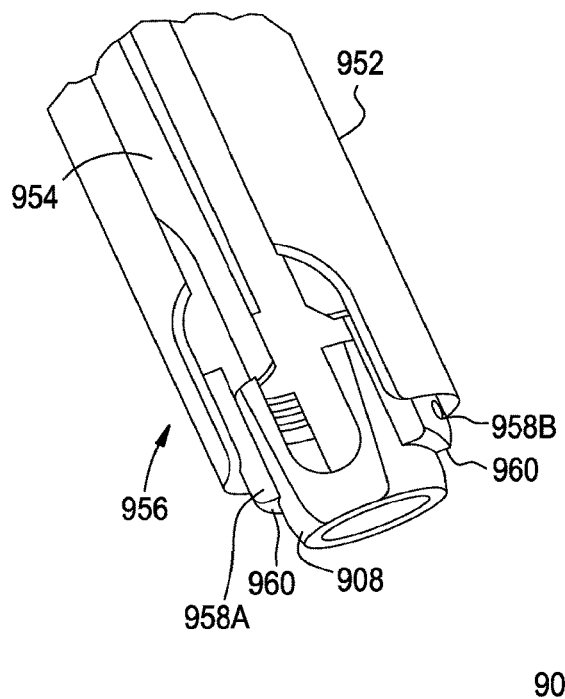
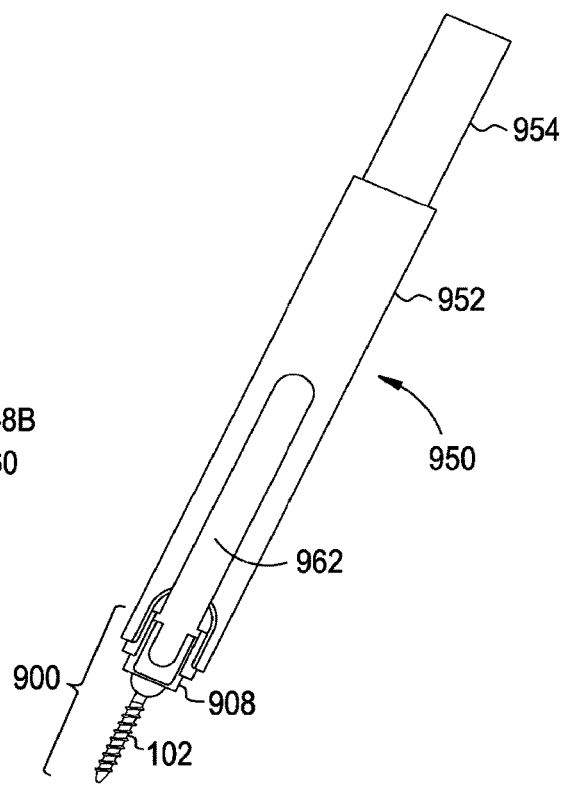

PERCUTANEOUS ACCESS DEVICES AND BONE ANCHOR ASSEMBLIES

CROSS REFERENCE TO RELATED APPLICATIONS

This application is a continuation of U.S. application Ser. No. 13/938,222 filed on Jul. 9, 2013, which is a continuation of U.S. application Ser. No. 12/945,676 filed on Nov. 12, 2010 (now U.S. Pat. No. 8,518,082), which is a continuation of U.S. application Ser. No. 11/692,531 filed on Mar. 28, 2007 (now U.S. Pat. No. 7,854,751), which is a continuation of U.S. application Ser. No. 11/672,539 filed on Feb. 8, 2007 (now abandoned), which is a continuation of U.S. application Ser. No. 10/738,286 filed on Dec. 16, 2003 (now U.S. Pat. No. 7,179,261), each of which is hereby incorporated herein by reference.

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation elements can have a predetermined contour that has been designed according to the properties of the target implantation site, and once installed, the fixation element holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped recess formed in the head. A set-screw, plug, or similar type of closure mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other closure mechanism to securely interconnect each screw and the fixation rod.

Recently, the trend in spinal surgery has been moving toward providing minimally invasive devices and methods for implanting bone anchors and spinal fixation devices.

SUMMARY

Disclosed herein are percutaneous access devices that facilitate the delivery and implanting of bone anchors into bone, in particular, one or more vertebral bodies of the spine. In particular, the disclosed percutaneous access devices permit the delivery and implanting of one or more bone anchors in a minimally invasive manner thereby limiting trauma to surrounding tissue. Moreover, the percutaneous access devices disclosed herein can provide a percutaneous pathway between a skin incision and the bone anchor that may be used to deliver components of the bone anchor, such as the fastening mechanism, the fixation element, and/or instruments to the bone anchor. Also, disclosed herein are bone anchors that facilitate the connection of instruments, such as a percutaneous access device, to the bone anchor.

In accordance with one exemplary embodiment, a percutaneous access device includes an inner tube and an outer tube disposed about at least a portion of the inner tube. The outer tube, in the exemplary embodiment, is sized to span from at least a skin incision in a patient to a predetermined site proximate the spine of the patient. The distal end of the outer tube may be adapted to releasably engage a bone anchor. The inner tube, in the exemplary embodiment, may be adjustable relative to the outer tube along the longitudinal axis of the outer tube between a first position and a second position in which the distal end of the inner tube contacts the bone anchor.

In accordance with another exemplary embodiment, a bone anchor assembly includes a bone anchor having a proximal head and a distal bone engaging portion and a receiving member coupled to the bone anchor. The receiving member, in the exemplary embodiment, may have a proximal end, a distal end and a recess for receiving a spinal fixation element, such as a rod or a plate. The proximal end of the receiving member, in the exemplary embodiment, may have at least one arcuate groove formed on an exterior surface thereof to facilitate connection of an instrument, such as a percutaneous access device, to the receiving member.

BRIEF DESCRIPTION OF THE DRAWINGS

These and other features and advantages of the percutaneous access devices and bone anchor assemblies disclosed herein will be more fully understood by reference to the following detailed description in conjunction with the attached drawings in which like reference numerals refer to like elements through the different views. The drawings illustrate principles of the percutaneous access devices and bone anchor assemblies disclosed herein and, although not to scale, show relative dimensions.

FIGS. 18A and 18B are perspective views of an alternative embodiment of a percutaneous access device and a bone anchor assembly, illustrating a plurality of externally threaded removable tabs for releasable engagement with an instrument such as a percutaneous access device;

FIGS. 23A-23B are perspective views of an alternative embodiment of a percutaneous access device and a bone anchor assembly, illustrating flexible tabs provided on the distal end of the percutaneous access device for releasable engagement with the bone anchor assembly.

DETAILED DESCRIPTION

Figure 1:
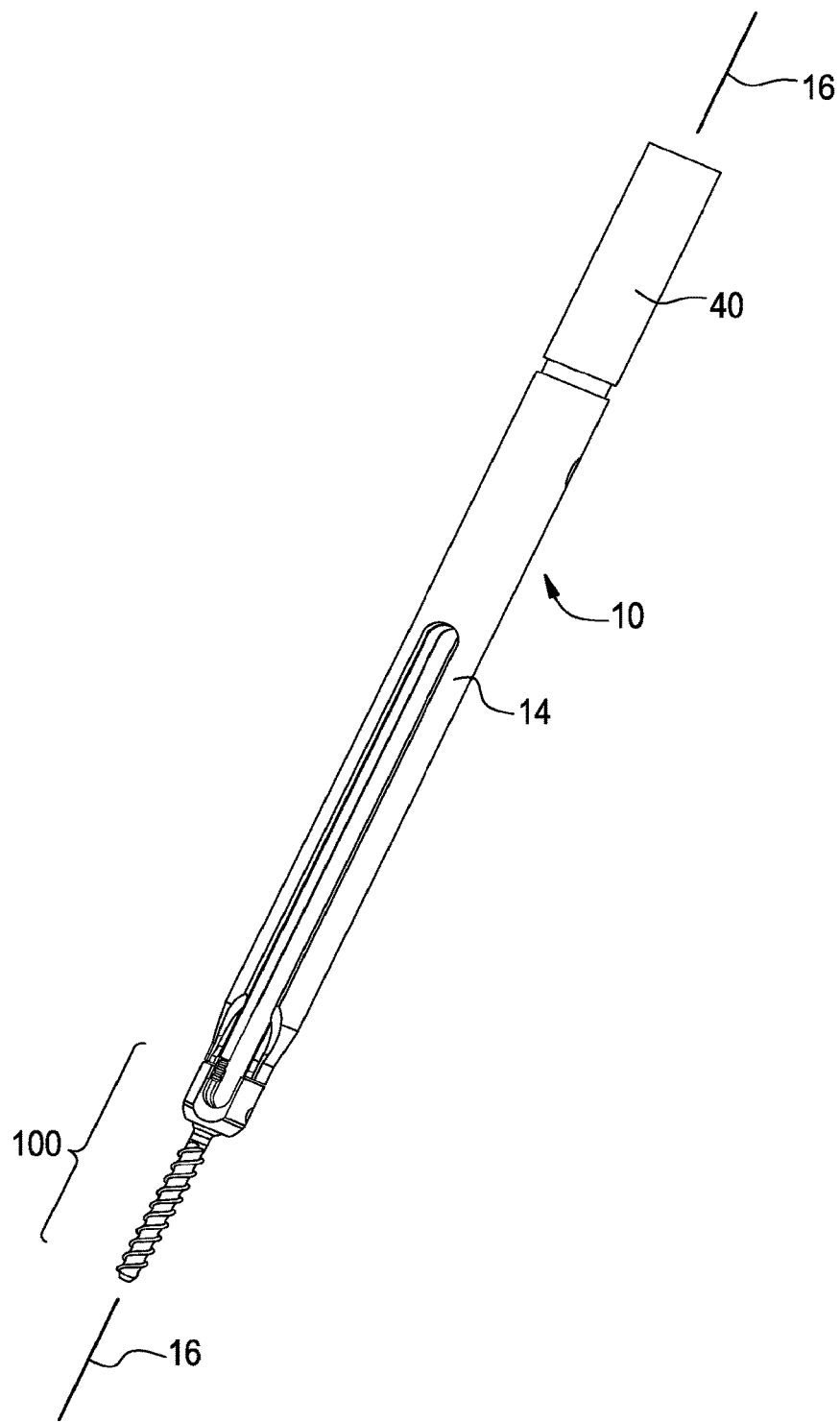
FIG. 1 is a perspective view of an exemplary embodiment of a percutaneous access device.
Figure 2:
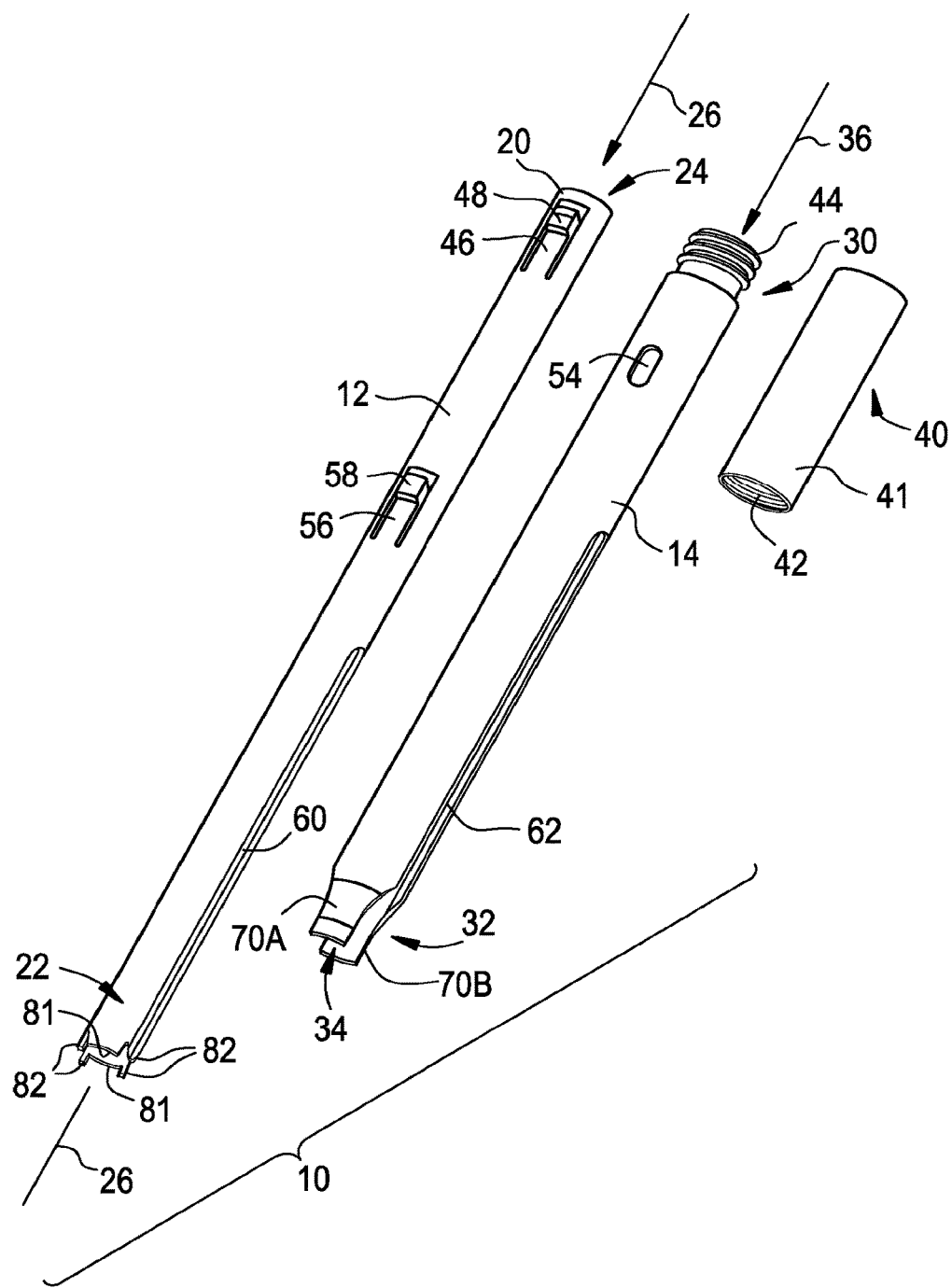
FIG. 2 is a perspective view of the components of the percutaneous access device of FIG. 1.

Certain exemplary embodiments will now be described to provide an overall understanding of the principles of the structure, function, manufacture, and use of the percutaneous access devices and bone anchor assemblies disclosed herein. One or more examples of these embodiments are illustrated in the accompanying drawings. Those of ordinary skill in the art will understand that the percutaneous access devices and bone anchor assemblies specifically described herein and illustrated in the accompanying drawings are non-limiting exemplary embodiments and that the scope of the present invention is defined solely be the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The term "distal" as used herein with respect to any component or structure will generally refer to a position or orientation that is proximate, relatively, to the bone surface to which a bone anchor is to be applied. Conversely, the term "proximal" as used herein with respect to any component or structure will generally refer to a position or orientation that is distant, relatively, to the bone surface to which a bone anchor is to be applied.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a percutaneous access device 10. The exemplary percutaneous access device 10 can facilitate the delivery and implanting of a bone anchor, such as the exemplary bone anchor assembly 100 illustrated and described below, into bone, in particular, one or more vertebral bodies of the spine. In particular, the exemplary percutaneous access device 10 can facilitate the delivery and implanting of a bone anchor in a minimally invasive manner and can provide a percutaneous pathway between a skin incision in the patent and the bone anchor that may be used to deliver components of the bone anchor, such as the closure mechanism, one or more fixation elements, and/or instruments to the bone anchor. The percutaneous access device 10 is preferably adapted to be introduced through a minimally invasive percutaneous incision, which is a relatively small incision that typically has a length less than the diameter or width of the device being inserted therethrough. Although the exemplary percutaneous access device 10 described below is designed primarily for use in spinal applications, one skilled in the art will appreciate that the exemplary percutaneous access device 10, as well as the other exemplary embodiments described below, may be used to facilitate the implantation of any type of bone anchor to any type of bone.

The exemplary percutaneous access device 10 includes an inner tube 12 and an outer tube 14 disposed about at least a portion of the inner tube 12. In the illustrated exemplary embodiment, the outer tube 14 is coaxially disposed about the inner tube 12 such that the inner tube 12 and the outer tube 14 share a common longitudinal axis 16. One skilled in the art will appreciate, however, that the outer tube 14 and inner tube 12 need not be coaxially aligned. The inner tube 12 and the outer tube 14, in the exemplary embodiment, are generally cylindrical in shape, having an approximately circular cross-section. One skilled in the art will appreciate, however, the inner tube 12 and the outer tube 14 may have other cross-sectional shapes, including, for example, elliptical or rectilinear. In the exemplary embodiment, the inner tube 12 and outer tube 14 have analogous cross-sections, however, one skilled in the art will appreciate the inner tube 12 and the outer tube 14 can have different cross-sectional shapes. The axial length of the inner tube 12 and outer tube 12 may vary depending on, for example, the patient anatomy, the procedures employed, and/or, that area of the spine in which the device 10 is employed. The inner tube 12 and the outer tube 14 may be linear, as in the exemplary embodiment, or may curved or angled along one or more sections or the entire length thereof. The inner tube 12 and the outer tube 14 may be constructed from any suitable biocompatible material, including, for example, a metal, such as stainless steel, or a polymer, from any conventional method of manufacturing medical devices.

Although the illustrated exemplary embodiment includes an inner tube and an outer tube, one skilled in the art will appreciate that any number of tubes, e.g., one or more tubes, may be employed depending on, for example, the type of bone anchor employed and the manner by which the device is releasably engaged to the bone anchor. For example, exemplary embodiments of a percutaneous access device having a single outer tube are described below.

Figure 3:
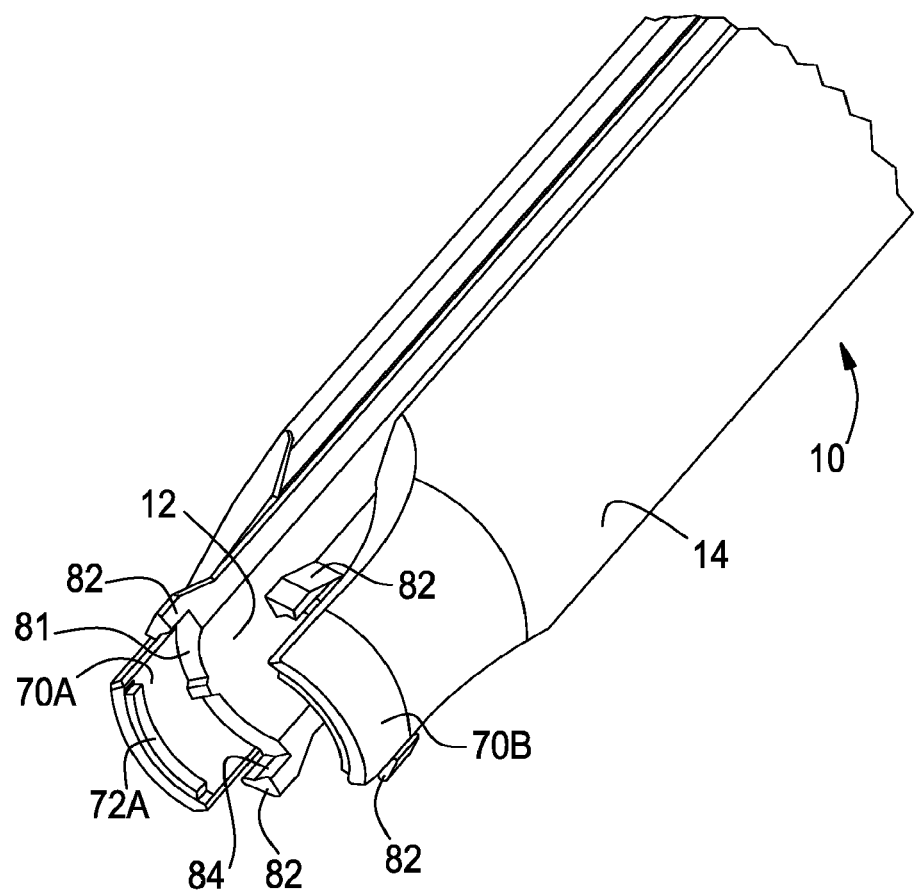
FIG. 3 is a perspective view of the distal end of the percutaneous access device of FIG. 1.
Figure 4:
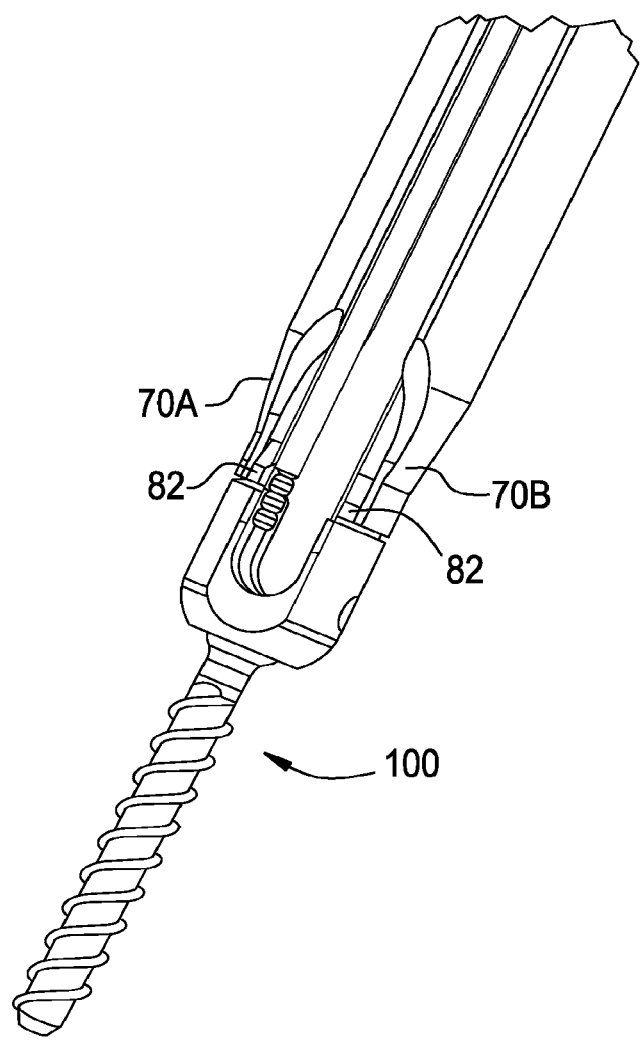
FIG. 4 is a perspective view of the distal end of the percutaneous access device of FIG. 1 coupled to an exemplary embodiment of a bone anchor assembly.
Figure 7:
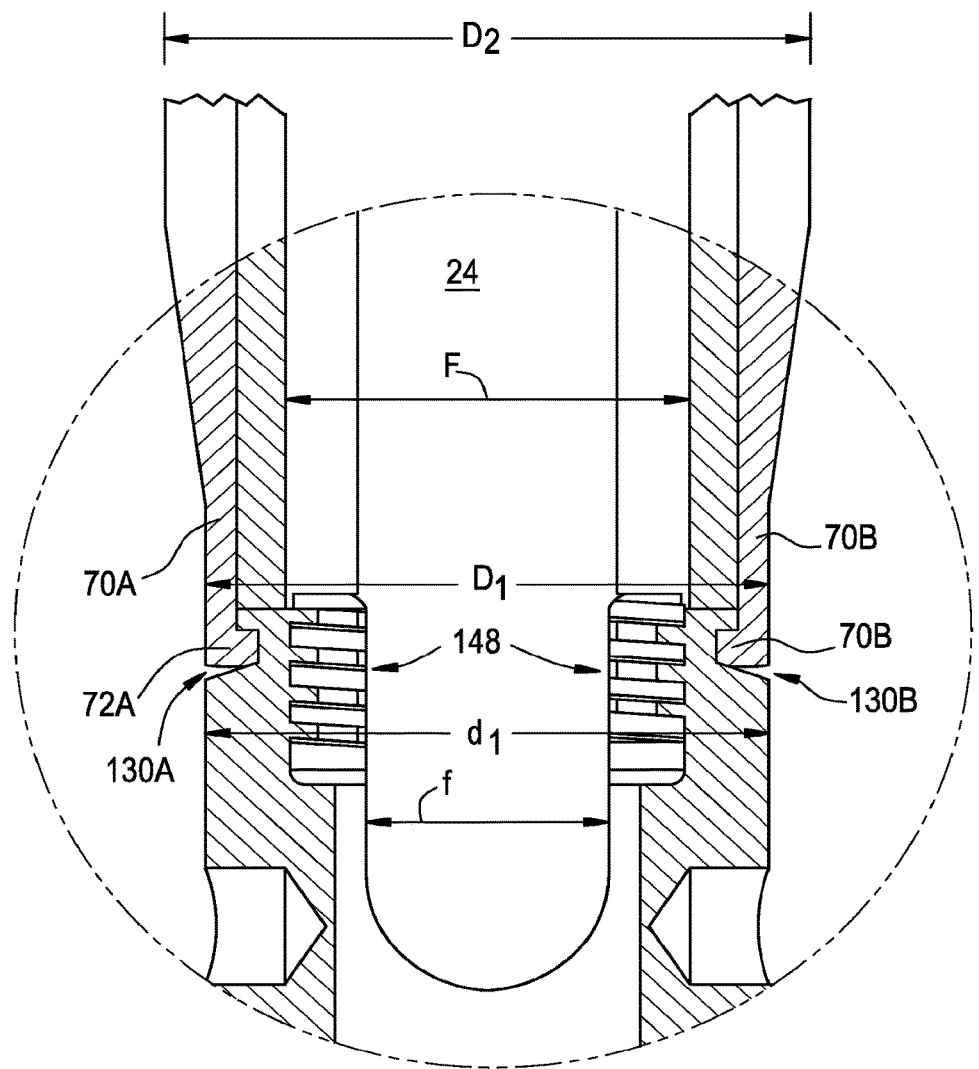
FIG. 7 is a side elevational view in cross-section of the distal end of the percutaneous access device of FIG. 1 coupled to the receiving member of the bone anchor assembly of FIG. 4.

Continuing to refer to FIGS. 1-5, the inner tube or sleeve 12 includes a proximal end 20, a distal end 22, and a lumen 24 extending between the proximal end 20 and the distal end 22. The lumen 24 extends the length of the inner tube 12 and defines a longitudinal axis 26 of the inner tube 12. The outer tube or sleeve 14 includes a proximal end 30, a distal end 32, and a lumen 34 extending between the proximal end 30 and the distal end 32. The lumen 34 may extend the length of the outer tube 14 and defines a longitudinal axis 36 of the outer tube 14. The inner tube 12 in positionable within the lumen 36 of the outer tube 14. In the exemplary percutaneous access device 10, the inner tube 12 is longitudinally adjustable with respect to the outer tube 14. For example, the inner tube 12 may adjustable from a first, proximal position, in which the distal end 22 of the inner tube 12 is positioned proximal to the distal end 32 of the outer tube 14 as illustrated in FIG. 3, and a second, distal position, in which the distal end 22 of the inner tube 12 is positioned proximate to the distal end 32 of the outer tube 14. In the exemplary embodiment, the distal end 22 of the inner tube 12 preferably contacts at least a portion of the bone anchor assembly when the inner tube 12 is in the second position, as illustrated in FIGS. 4 and 7 and as discussed in more detail below.

The exemplary percutaneous access device 10 may include an adjustment mechanism 40 that allows an operator to adjust the relative longitudinal position of the inner tube 12 and the outer tube 14. In the illustrated embodiment, for example, the adjustment mechanism 40 is a hollow, tubular shaped cap 41 having internal threads 42 that engage external threads 44 provided on the proximal end 30 of the outer tube 14. The threads 42, 44 allow the cap 41 to be longitudinal adjusted relative to the outer tube 14. In the exemplary embodiment, the inner tube 12 is connected to the cap 41 and, thus, can move with cap 41 as the cap 41 is advanced or withdrawn relative to the outer tube 14. For example, the proximal end 30 of the inner tube 12 of the exemplary embodiment may include one or more resilient tabs 46, one or more of which may have a projection 48 that seats within an annular grove provided on the interior surface of the cap 41 to thereby connect the proximal end 30 of the inner tube 12 to the cap 41. In the illustrated embodiment, two resilient tabs 46 are provided on opposite sides of the outer tube 14. The projection 48, in the exemplary embodiment, is sized to rotate with in the groove provided in the cap 41, thus allowing the cap 41 to rotate relative to the inner tube 12. The resilient tabs 46 are radially flexible to facilitate connection to and removal from the cap 41. One skilled in the art will appreciate that other configurations for connecting the inner tube 12 to the cap 41 are possible and are within the scope of the present disclosure.

The inner tube 12 may be inhibited from rotating with respect to the outer tube 14, limiting the relative motion of the inner tube 12 and the outer tube 14 to along the longitudinal axis 16 of the percutaneous access device. For example, one or more resilient tabs 56 may be provided on the inner tube 12 approximately midway between the proximal end 20 and the distal end 22 of the inner tube 12, although other positions are possible. In the illustrated embodiment, two resilient tabs 56 are provided on opposite sides of the outer tube 14. One or more of the resilient tabs 56 may include a projection 58 that is sized and shaped to seat within a longitudinal slot 54 provided in the outer sleeve 14. The resilient tab 56 can be radially flexible to facilitate insertion into and removal from the slot 54. The projection 58 can slide within the slot 54 and, thereby can limit the relative motion between the inner tube 12 and the outer tube 14 to along the longitudinal axis 16 of the percutaneous access device 10. One skilled in the art will appreciate that other configurations for connecting the inner tube 12 to the outer tube 14 are possible and are within the scope of the present disclosure.

The inner tube 12 may have one or more sidewall openings or slots 60 formed therein. In the illustrated exemplary embodiment, the inner tube 12 includes two opposed slots 60 that extend longitudinally from the distal end 22 of the inner tube 12. Like the inner tube 12, the outer tube 14 may have one or more sidewall openings or slots 62 formed therein. In the illustrated exemplary embodiment, the outer tube 14 includes two opposed slots 62 that extend longitudinally from the distal end 32 of the inner tube 12. The slots 60 and 62 can be used to facilitate positioning of a spinal fixation device, such as a rod or a plate, relative to one or more bone anchors. Methods and devices for spinal fixation element placement are disclosed in commonly owned U.S. patent application Ser. No. 10/737,537, filed on Dec. 16, 2003, entitled Method and Devices for Spinal Fixation Element Placement (now U.S. Pat. No. 7,666,188) and commonly owned U.S. patent application Ser. No. 10/738,130, filed on Dec. 16, 2003, entitled Method and Devices for Minimally Invasive Spinal Fixation Element Placement (now U.S. Pat. No. 7,527,638), both of which are incorporated herein in by reference. To facilitate positioning of a spinal fixation element, the slots 60 and the slots 62 are preferably aligned with one another along at least a portion of the longitudinal axis of the percutaneous access device 10. The width and length of the slot 60 and slot 62 may be varied depending on the particular methods, instruments, and fixation elements being employed. In one exemplary embodiment, for example, the length of the slots 60 and 62 is selected to span at least from the skin incision to the distal end of the inner tube 12 and the outer tube 14, respectively. In such embodiments, the slots 60 and 62 may be accessible from outside of the patient. In another exemplary embodiment, the length of the slots 60 and 62 is selected to span from the distal end of the inner tube 12 and the outer tube 14, respectively, to a point distal to the skin incision. In such embodiments, the slots 60 and 62 may be accessible only from the lumens of the inner and outer tubes.

In embodiments in which multiple slots are employed, the slots 60, 62 need not be similarly sized (width and/or length). For example, the one or more slots 60 may be sized differently than the one or more slots 62, the one or more of the slots 60 on the inner tube may be sized differently than other slots 60, and/or one or more of the slots 62 on the outer tube may be sized differently than other slots 62. Although the exemplary embodiment includes two opposing slots on the inner tube 12 and the outer tube 14, respectively, one skilled in the art will appreciate that any number of slots may be provided, e.g., no slots, one, two, three, etc. slots, may be provided depending on the method, instruments, and/or fixation element employed.

One skilled in the art will appreciate that the slots 60 and 62 are optional and that in certain embodiments slots may not be provided.

Referring to FIGS. 1-5 and 7, the percutaneous access device 10 is preferably releasably engageable to a bone anchor. In the exemplary embodiment, the outer tube 14 may be releasably engaged to a bone anchor, such as bone anchor assembly 100. For example, the outer tube 14 may be engaged to a bone anchor in a manner that allows the percutaneous access device 10 to be connected to the bone anchor 100 during use, e.g., during implantation and/or delivery and/or fastening of a spinal fixation element to the bone anchor, and allows the percutaneous access device to be disconnected from the bone anchor 100 at the conclusion of the procedure. Preferably, the percutaneous access device 10 can be disconnected remotely. For example, the exemplary embodiment, the percutaneous access device 10 can be disconnected from the bone anchor by manipulation of the proximal end of the percutaneous access device 10, as discussed in more detail below.

The distal end 32 of the outer tube 14 includes a pair of opposed longitudinally extending tabs 70A and 70B that may releaseable engage a bone anchor. In the exemplary embodiment, the tabs 70A and 70B are defined by the sidewalls of the outer tube 14 and are separated by slots 62A and 62B. In certain exemplary embodiments, the tabs 70A and 70B may be flexible and resilient in the radial direction to facilitate connection to a bone anchor. For example, the tabs 70A and 70B may be flexed apart in the radial direction from a first, relaxed position to facilitate advancement of the tabs longitudinally over a portion of the bone anchor. Once positioned about a portion of the bone anchor, the tabs 70A and 70B may provide a radially compressive force on the bone anchor as the tabs 70A and 70B attempt to return to the first, relaxed position. In other exemplary embodiments, including the exemplary percutaneous access device 10, the tabs 70A and 70B need not be flexible and resilient.

Figure 8:
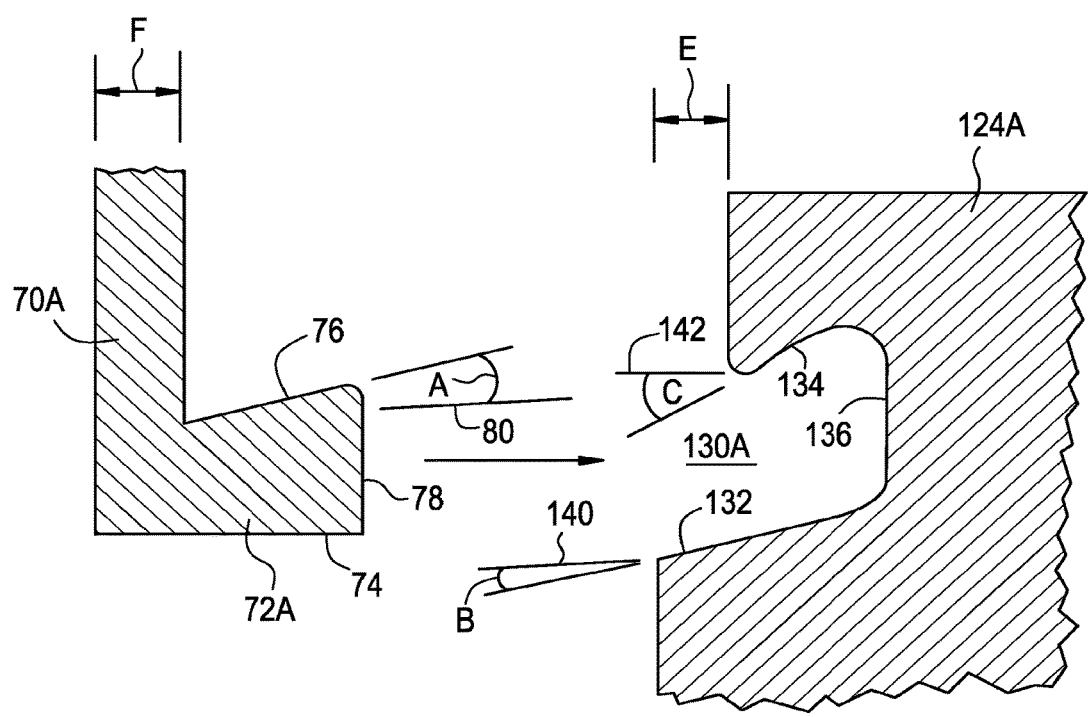
FIG. 8 is a side elevational view in cross-section of the distal end of the outer tube of the percutaneous access device of FIG. 1 and the receiving member of the bone anchor assembly of FIG. 4.
Figure 9:
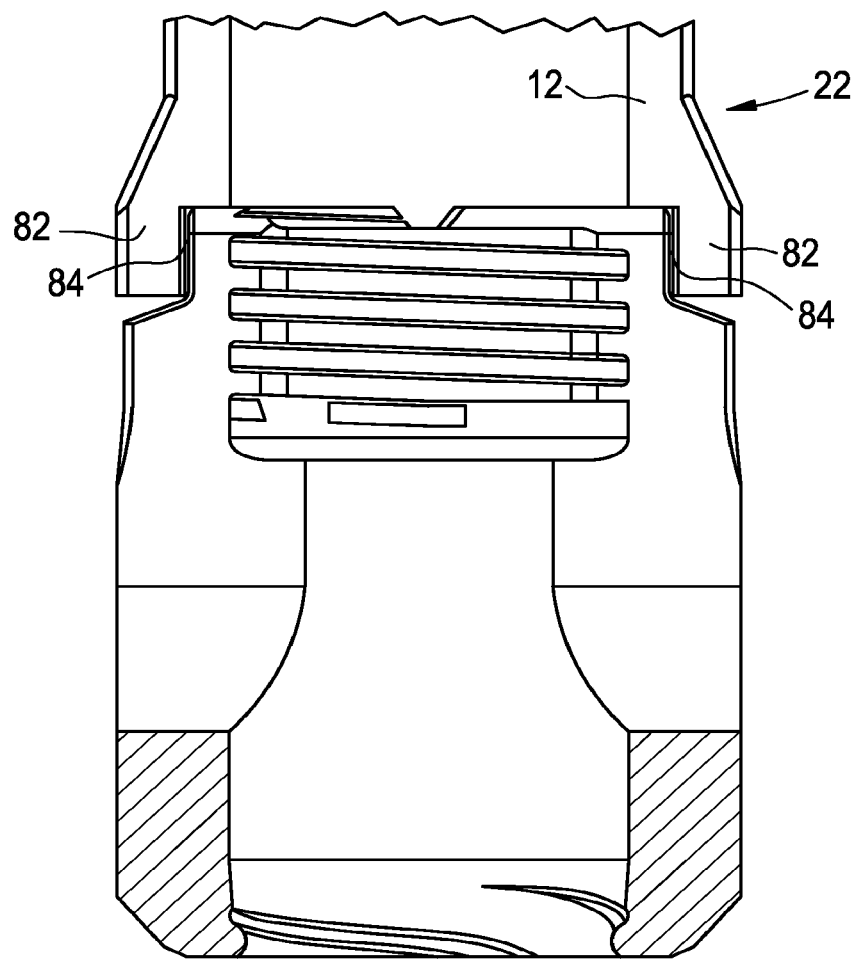
FIGS. 9 and 10 are side elevational views in cross section of the distal end of the inner tube of the percutaneous access device of FIG. 1 and the receiving member of the bone anchor assembly of FIG. 4.
Figure 10:
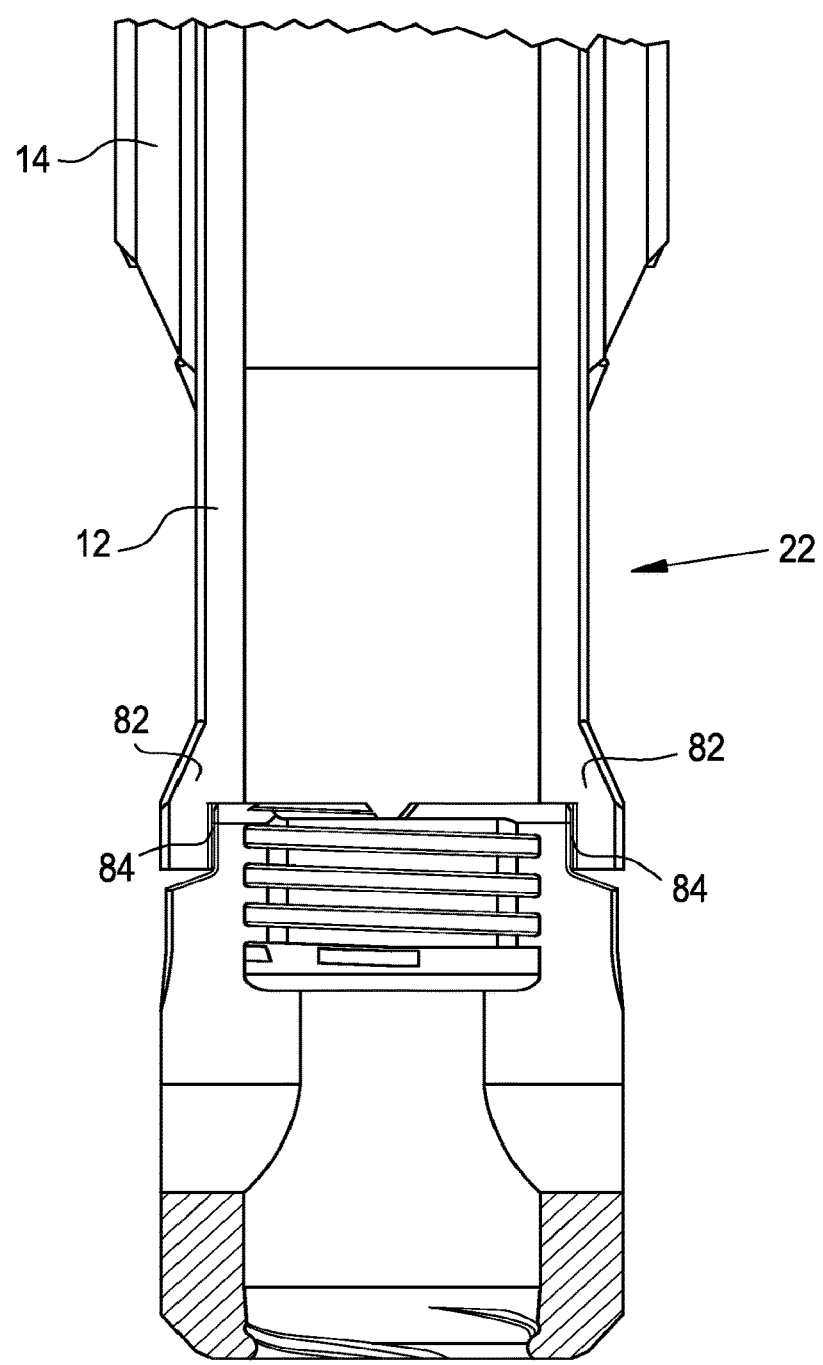

In the illustrated exemplary embodiment, each tab 70A and 70B may include one or more radially inward facing projection 72 that is sized and shaped to seat within an opening provided in a portion of the bone anchor. The size, shape and number of projections can be varied depending on, for example, the opening(s) provided on the bone anchor and type of connection desired. In the illustrated exemplary embodiment, for example, each projection 72A, 72B is generally arcuate in shape and has a cross section that is complementary to an arcuate groove 130 provided in the spinal fixation element receiving member 108 of the exemplary bone anchor assembly 100 described below. In particular, the projection 72A has a distal surface 74, a proximal surface 76, and a generally radially facing connecting surface 78 that spans between the distal surface 74 and the proximal surface 76, as shown in FIG. 8. In the illustrated embodiment, the distal surface 74 is generally oriented perpendicular to the longitudinal axis of the outer tube 14 and the connecting surface 78 is generally oriented parallel to the longitudinal axis of the outer tube 14 and perpendicular to the distal surface 74. One or both of the proximal surface 76 and the distal surface 74 may be oriented at an angle other than perpendicular to the longitudinal axis of the outer tube 14. For example, the proximal surface 76 may be oriented at an angle A to an orthogonal line 80, which is oriented perpendicular to the longitudinal axis of the outer tube 14. In the exemplary embodiment, the angle A may be approximately 5° to approximately 30° and is preferably approximately 20°. The distal surface 74 and the proximal surface 76 may be oriented at the same angle or, as in the exemplary embodiment, may be oriented at different angles.

Referring to FIGS. 2, 3, 4, 7, 9 and 10, the distal end 22 of the inner tube 12 may include a contact surface 81 that contacts at least a portion of a bone anchor when the inner tube 12 is in the second position. In the illustrated exemplary embodiment, for example, the distal end 22 of the inner tube 12 may have two opposing generally arcuate contact surfaces 81. The contact surfaces 81, in the exemplary embodiment, are oriented approximately perpendicular to the longitudinal axis of the inner tube 12. In the illustrated exemplary embodiment, the contact surfaces 81 are configured to contact a generally arcuate contact surface provided on the proximal end of the receiving member of the exemplary bone anchor assembly 100. Preferably, the contact surface 81 is complementary in size, shape, and orientation to the contact surface on the bone anchor. One skilled in the art will appreciate that the configuration of the contact surface 81, e.g., number, size, shape, and orientation of the contact surface 81, may be varied to, for example, suit the bone anchor being employed.

The distal end 22 of the inner tube 12 and/or the distal end 32 of the outer tube 14 may be configured to inhibit rotation of the bone anchor assembly relative to the percutaneous access device 10. For example, the distal end 22 of the inner tube may include one or more finger-like extensions 82 that extend approximately axially from the distal end 22 of the inner tuber 12 and engage a bone anchor to inhibit rotation of the bone relative to the percutaneous access device. For example, one or more of the extensions 82 may seat within a groove, recess, slot, or similar structure provided in the bone anchor. Alternatively, one of more of the extensions 82 may include a contact surface 84 for contacting an axially extending surface of the bone anchor, as in the case of the exemplary embodiment and as discussed in detail below.

Figure 5:
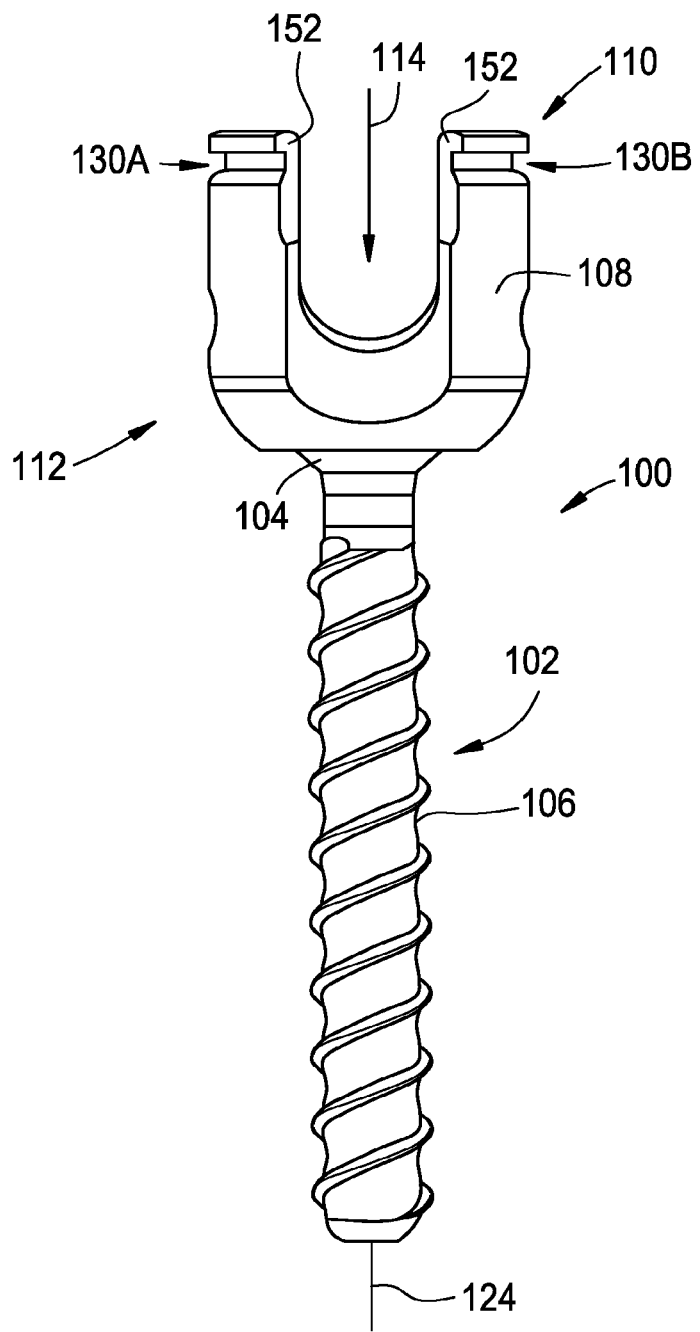
FIG. 5 is a side elevational view of the bone anchor assembly of FIG. 4.
Figure 6:
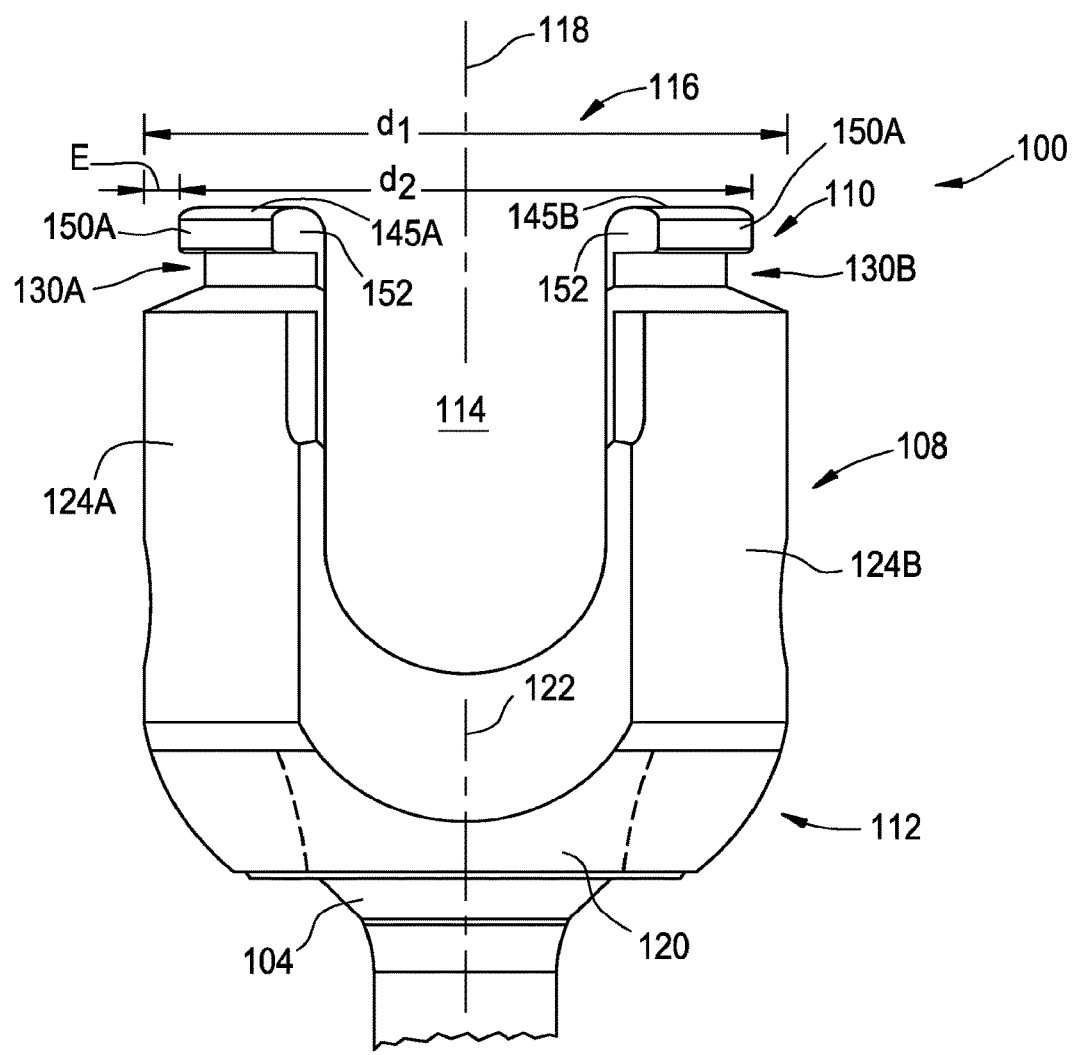
FIG. 6 is a side elevational view of the receiving member of the bone anchor assembly of FIG. 4.

FIGS. 5-6 illustrate an exemplary embodiment of a bone anchor assembly 100 that is particularly suited for use with the exemplary percutaneous access device 10 described. One skilled in the art will appreciate, however, that the percutaneous access devices disclosed herein are not limited to use with the exemplary bone anchor assembly 100 but instead may be configured for use with any type of bone anchor, e.g., bone screw or hook; mono-axial or polyaxial. Exemplary bone anchor assembly 100 includes a bone screw 102, such as a pedicle screw, having a proximal head 104 and a distal bone engaging portion 106, which in the illustrated exemplary embodiment is an externally threaded screw shank. The exemplary bone screw assembly 100 also includes a receiving member 108 that is configured to receive and couple a spinal fixation element, such as a spinal rod or spinal plate, to the bone anchor assembly 100.

The receiving member 108 may be coupled to the bone anchor 102 in any well-known conventional manner. For example, the bone anchor assembly may be poly-axial, as in the present exemplary embodiment in which the bone anchor 102 may be adjustable to multiple angles relative to the receiving member 108, or the bone anchor assembly may be mono-axial, e.g., the bone anchor 102 is fixed relative to the receiving member 108. An exemplary poly-axial bone screw is described U.S. Pat. No. 5,672,176, incorporated herein by reference. In mono-axial embodiments, the bone anchor 102 and the receiving member may be coaxial or may be oriented at angle with respect to one another. In polyaxial embodiments, the bone anchor may biased to a particular angle or range of angles to provide a favored angle the bone anchor. Exemplary favored-angle bone screws are described in U.S. Patent Application Publication No. 2003/0055426 and U.S. Patent Application Publication No. 2002/0058942, both of which are incorporated herein by reference.

The receiving member 108 of the illustrated exemplary embodiment includes a proximal end 110, a distal end 112, and a recess or slot 114 for receiving a spinal fixation element such as a spinal rod. The proximal end 110 of the receiving member 108 has a first bore 116 defining a first bore axis 118. The recess 114 communicates with the first bore 116 such that a spinal fixation element may be positioned through the first bore 116 into the recess 114. The distal end 112 has a second bore 120 opposite the second bore 116 and defining a second bore axis 122. The second bore axis 122 is designed to receive the head 104 of the bone anchor 102 to couple the bone anchor 102 to the receiving member 108. In the illustrated exemplary embodiment, the head 104 is seated within the second bore 116. As the exemplary illustrated embodiment of the bone anchor assembly is poly-axial, the bone anchor 102 is free to rotate relative to the receiving member 108 such that the longitudinal axis 124 of the bone anchor 102 is positionable at an angle relative to the second bore axis 120. The second bore 116 may be conically shaped to facilitate adjustment of the bone anchor 102 relative to the receiving member 108. In favored-angled embodiments, the second bore axis 122 may be positioned at an angle (other than 0°) to the first bore axis 118. In the illustrated embodiment, the first bore axis 118 and second bore axis 122 are coaxial. In the exemplary embodiment, the receiving member 108 has a generally U-shaped cross-section defined by two legs 124A and 124B separated by recess 114. Each leg 124A, 124B is free at the proximal end 110 of the receiving member 108.

The receiving member 108 may be configured to receive a closure mechanism that locks a spinal fixation element within the recess 114. The closure mechanism may be a cap that is advanceable through the first bore 116 of the receiving member 108 and seats against the spinal fixation element. For example, the cap may have external threads that engage internal threads 148 provided in the receiving member 108, e.g., on the legs 124A,B, as in the exemplary embodiment. Any type of conventional closure mechanism may be employed, including, for example, non-threaded caps, multi-component closure mechanisms, and/or external caps.

The receiving member 108 of the exemplary bone anchor assembly 100 is configured to be releasably connected to an instrument such as the exemplary percutaneous access device 10 described above. For example, the receiving member 108 may include at least one groove 130 that is configured to receive a portion of an instrument to releasably connect the instrument to the bone anchor assembly. The size, shape, position, and number of grooves can be varied depending on, for example, the instrument employed and the type of connection desired. In certain embodiments, for example, at least one arcuate groove 130 may be provided on an exterior surface of the proximal end 110 of the receiving member 108. In other exemplary embodiments, at least one arcuate groove may be provided on an interior surface of the proximal end 110 of the receiving member 108. In the illustrated exemplary embodiment, each leg 124A and 124B may be provided with an arcuate groove 130A, 130B, respectively, at the free, proximal end of the leg 124A, 124B. The grooves 130A, 130B may extend about a portion or all of the circumference of the proximal end of each leg 124A, 124B. Each groove 130A, 130B may have size and shape that is complementary in size and shape to a projection provided on the instrument. For example, in the illustrated exemplary embodiment, the each groove 130A, 130B may be arcuate and may have a cross-section complementary to the cross-section of a projection 72A,72B provided on the tabs 70A,70B of the outer sleeve 14. In particular, groove 130 may have a distal surface 132, a proximal surface 134 and an interconnecting surface 136 that spans between the distal surface 132 and the proximal surface 134, as illustrated in FIG. 8. The distal surface 132 and/or the proximal surface 134 may be oriented to facilitate insertion of a projection into the grove 130 and/or to inhibit undesirable separation of the projection from the groove 130. In the illustrated exemplary embodiment, for example, the distal surface 132 may be generally oriented at an angle B to an orthogonal line 140, which is oriented perpendicular to the longitudinal axis of the receiving member 108, to facilitate insertion of the projection into the groove. In the exemplary embodiment, the angle B may be approximately 0° to approximately 45° and preferably approximately 30° to 40°. In the illustrated exemplary embodiment, the proximal surface 134 may be oriented at an angle other than perpendicular to longitudinal axis of the receiving member 108 to inhibit separation of the projection from the groove 130, particularly in radial direction. For example, the proximal surface 134 may be oriented at an angle C to an orthogonal line 142, which is perpendicular to the longitudinal axis of the receiving member 108. In the exemplary embodiment, the angle C may be approximately 5° to approximately 30° and is preferably approximately 20°. The distal surface 132 and the proximal surface 76 may be oriented at the same angle or, as in the exemplary embodiment, may be oriented at different angles. The grooves 130A and 130B, as well as any additional grooves, may have similar cross-sectional geometries, as in the case of the illustrated exemplary embodiment, or may have distinct geometries.

Referring to FIGS. 7 and 8, the proximal surface 76 of each projection 72 may be oriented at an angle A that is approximately equal to the angle C of the proximal surface 134 of the corresponding groove. In one preferred embodiment, for example, angle A and angle C are each approximately 20°. One skilled in the art will appreciate that angle A and angle C need not be approximately equal but instead, may be separate, distinct angles.

The proximal end 110 of the receiving member 108 may include one or more contact surfaces that may be contacted by an instrument such as the percutaneous access device 10. In the illustrated exemplary embodiment, for example, the proximal end of each leg 124A, 124B may include one or more generally arcuate, proximally facing contact surfaces 145.

The outer diameter of the percutaneous access device may be selected to be approximately equal to the outer diameter of the bone anchor to facilitate insertion of the bone anchor into the body through a percutaneous pathway of minimal size. For example, in the illustrated exemplary embodiment, the outer diameter of the outer tube 14, indicated by line $D_1$ in FIG. 7, at at least the distal end 32 of the outer tube 14, is approximately equal to, or less than, the outer diameter of the receiving member 108, indicated by line $d_1$ in FIGS. 6 and 7. For example, the diameter of the outer tube 14 may taper from a proximal diameter $D_2$ to a distal diameter $D_1$ at the distal end 32 of the outer tube 14. Alternatively, the outer diameter of the outer tube 14 may be approximately equal to, or less than, the outer diameter of the receiving member 108 along the entire length of the outer tube 14. To accommodate the outer tube 14, the proximal end 110 of the receiving member 108 may have a diameter $d_2$ that is less than the diameter $d_1$ of a distal section of the receiving member 108, as illustrated in FIG. 6. For example, the diameter $d_2$ proximal to the grooves 130A,B may be less than the diameter $d_1$ of the receiving member 108 to provide a reduced diameter portion 150 at the proximal end 130 of the receiving member. The distance between the exterior surface of reduced diameter portion 150 and the exterior surface of the receiving member 108, indicated by line E in FIGS. 6 and 8, is preferably greater than or approximately equal to the radial thickness of a tab 70A, 70B, as indicated by line F in FIG. 8.

To facilitate delivery of devices to the bone anchor assembly through the percutaneous access device 10, the inner diameter of the lumen 24 of the inner tube 12, indicated by line F in FIG. 7, at at least the distal end of the inner tube 12, may be greater than or approximately equal to the inner diameter of at least a portion of the receiving member, indicated by line f in FIG. 7.

Figure 11A:
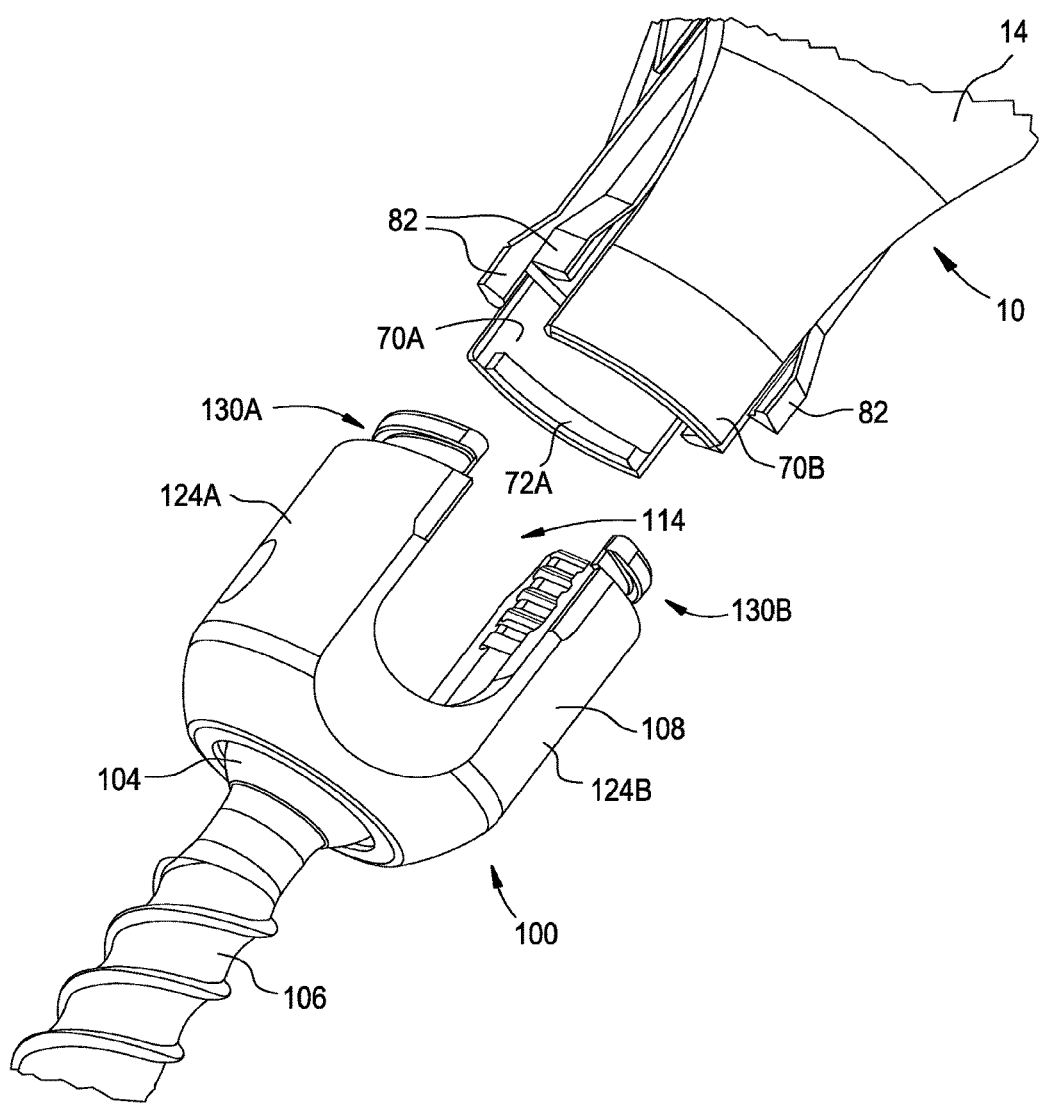
FIGS. 11A-11D are perspective views of the distal end of the percutaneous access device of FIG. 1 and the receiving member of the bone anchor assembly of FIG. 4, illustrating exemplary steps for releasably coupling the distal end of the percutaneous access device to the receiving member of the bone anchor assembly.
Figure 11B:
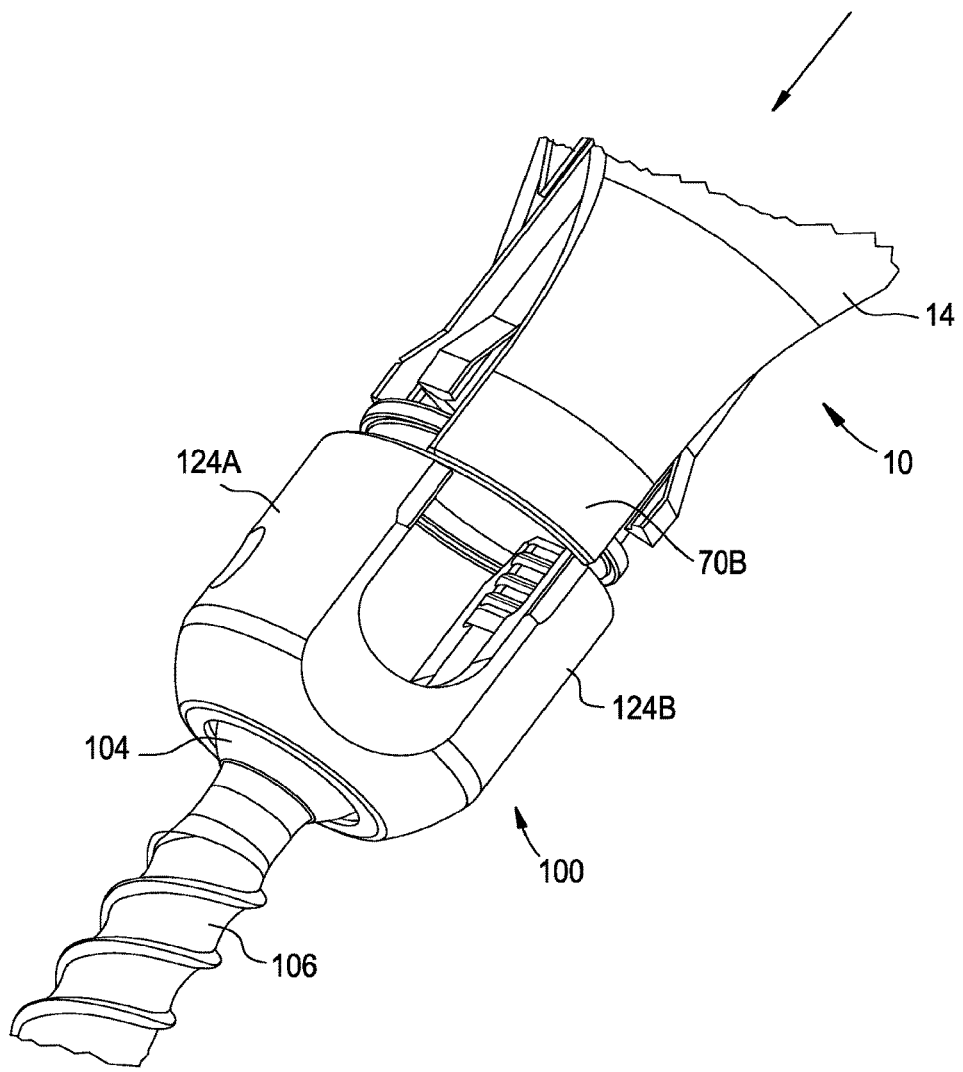
Figure 11C:
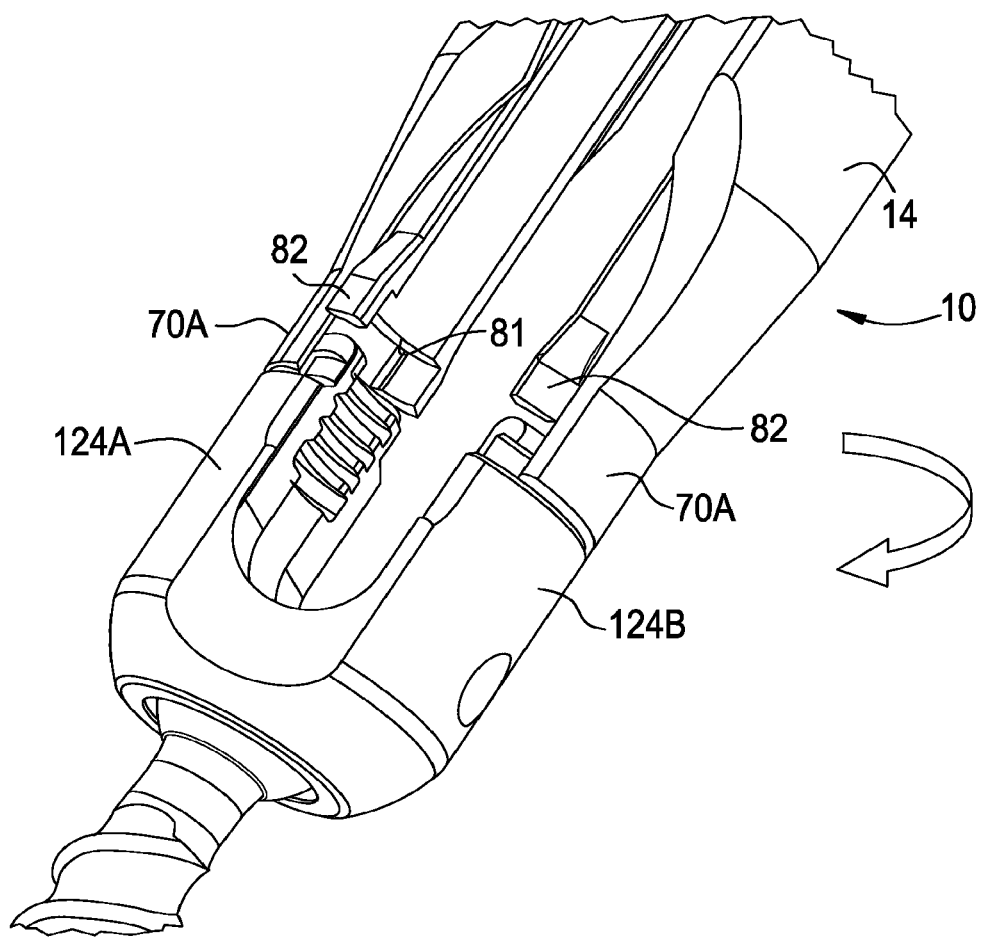

Exemplary operation of the percutaneous access device 10 with the exemplary bone anchor assembly will be described with reference to FIGS. 11A-11D. To releasably connect the percutaneous access device 10, the distal end 32 of the outer tube 14 is oriented such that tabs 70A and 70B are aligned with recess 114, as illustrated in FIG. 11A. The percutaneous access device 10 is advanced distally until each tab 70A, 70B is positioned between the legs 124A and 124B, as illustrated in FIG. 11B. The percutaneous access device 10 may be rotated about its longitudinal axis 16 to rotate projections 72A, 72B into grooves 103B, 130A, respectively, as illustrated in FIG. 11C. The inner tube 12 may be advanced distally along the longitudinal axis 16 of the percutaneous access device 10 from the first, proximal position, illustrated in FIGS. 11A-C, to the second, distal position, illustrated in FIG. 11D, in which the contact surfaces 81 of the inner tube 12 contact the contact surfaces 145A, 145B provided on the proximal end of the receiving member of the exemplary bone anchor assembly 100, to thereby releasably connect the percutaneous access device 10 to the bone anchor assembly 100. The contact surface 84 of one or more of the extensions 82 may engage the axial extending contact surfaces 152 (FIGS. 5 and 6) to inhibit rotation between the percutaneous access device and the bone anchor assembly.

The percutaneous access device 10 may be connected to the exemplary bone anchor assembly 100, or another bone anchor assembly, before implantation of the bone anchor assembly or after the bone anchor assembly is implanted into the patient's body.

Figure 11D:
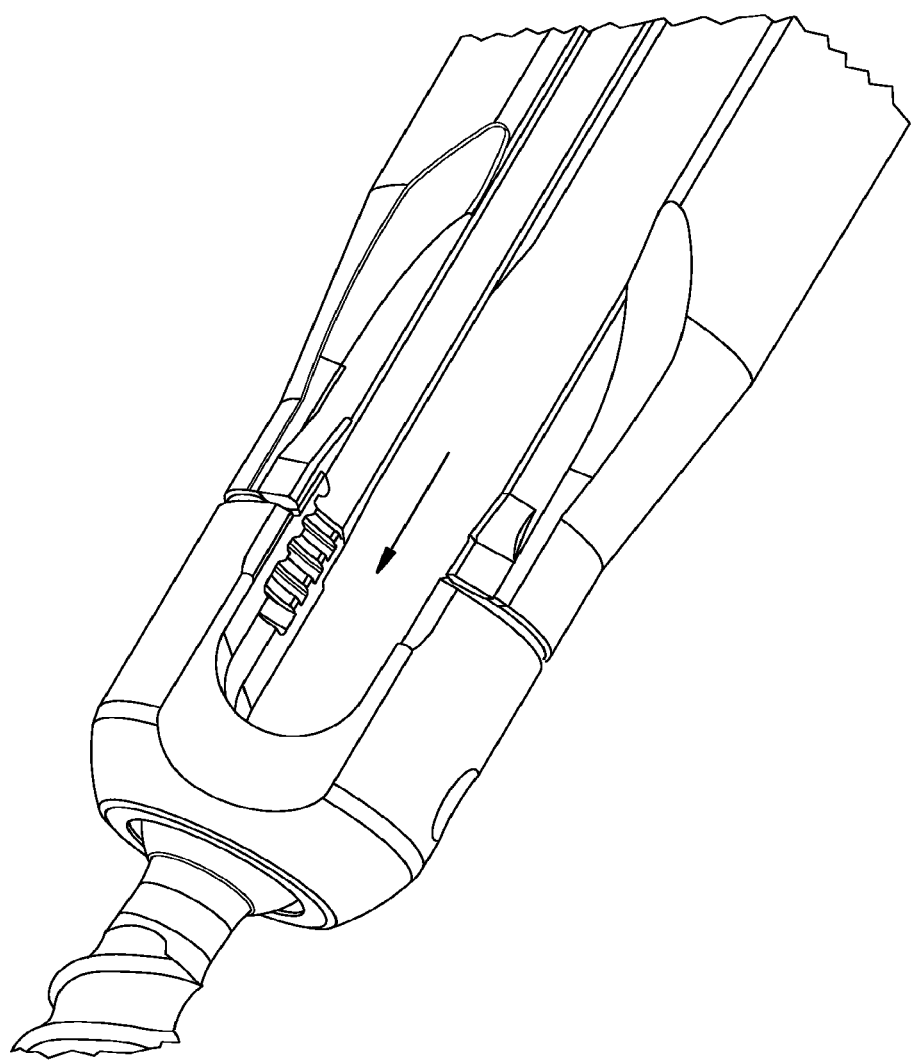
Figure 12:
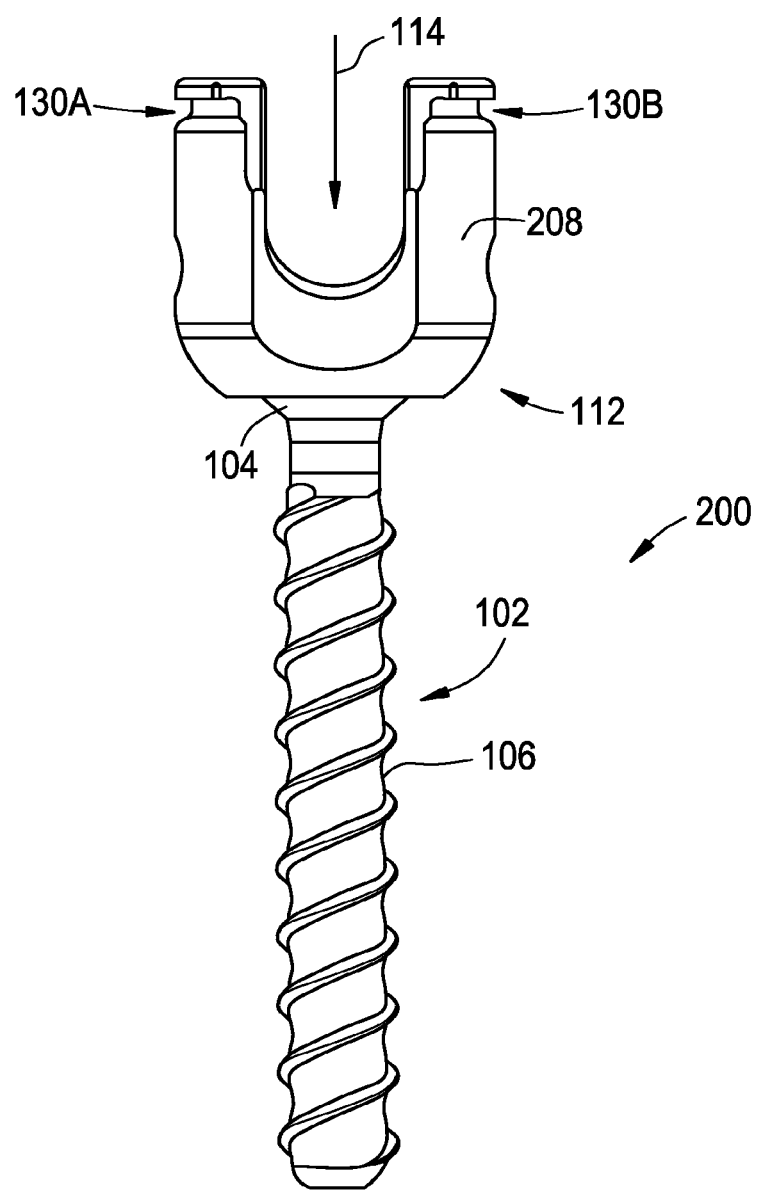
FIG. 12 is a side elevational view an another exemplary embodiment of a bone anchor assembly.
Figure 13:
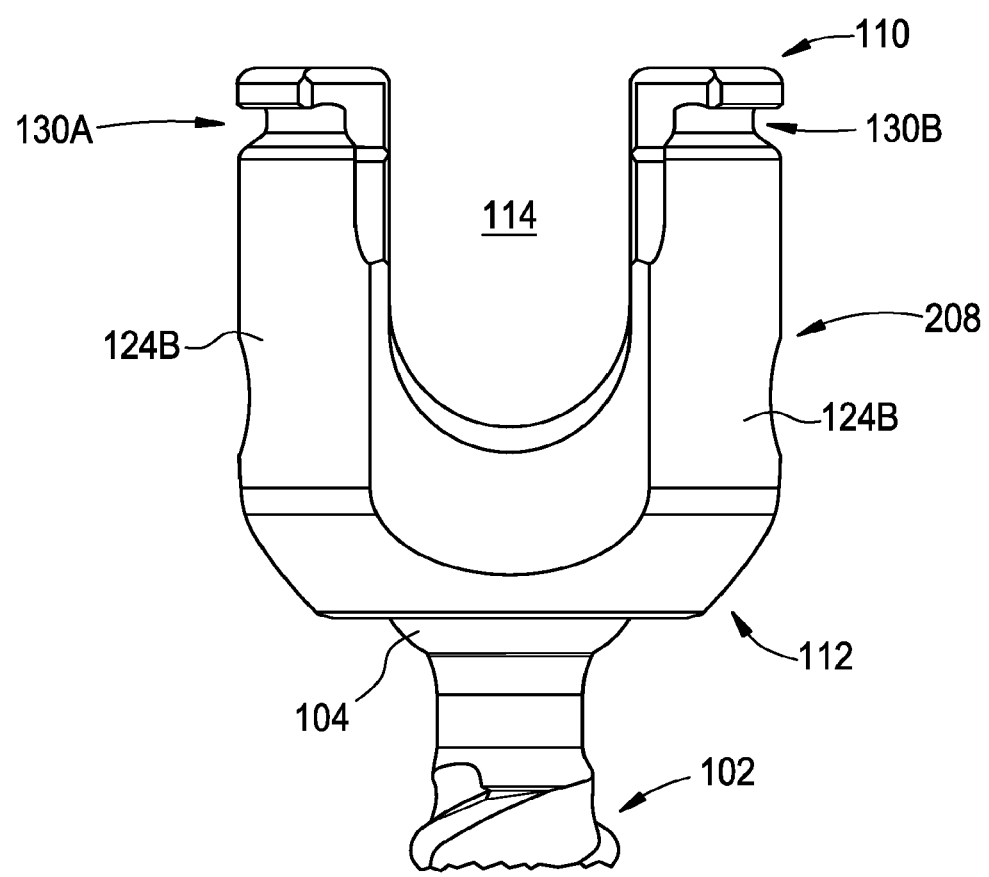
FIG. 13 is a side elevational view of the receiving member of the bone anchor assembly of FIG. 12.

Once the percutaneous access device 10 is releasably connected to the bone anchor assembly 100 as illustrated in FIGS. 1 and 11D, the percutaneous access device 10 may provide a percutaneous pathway between the skin incision and the bone anchor 100 that facilitates delivery of instruments, spinal fixation elements, and/or components of the bone anchor assembly, such as the closure mechanism, to the bone anchor assembly 100. In the illustrated exemplary embodiment, for example, the lumen 24 provides a pathway to the first bore 116 of the receiving member 108 of the bone anchor assembly 100, that may allow a closure mechanism, such as a threaded cap, to be delivered to the receiving member 108 of the bone anchor assembly and/or may allow a screw driver or the like to be advanced into engagement with the head 104 of the bone anchor 102. Moreover, in the illustrated exemplary embodiment, the slots 60 of the inner tube and the slots 62 of the outer tube 14 may be aligned with the recess 114 provided in the receiving member 108. Alignment of the slots 60 and 62 with the recess 114 facilitates the delivery of a spinal fixation element to the bone anchor assembly. Exemplary methods and devices for delivering a spinal fixation element to a bone anchor assembly are described in commonly owned, co-pending U.S. patent application Ser. No. 10/738,130, filed concurrently herewith, entitled Methods and Devices for Minimally Invasive Spinal Fixation Element Placement and commonly owned, co-pending U.S. patent application Ser. No. 10/737,537, filed concurrently herewith, entitled Methods and Devices for Spinal Fixation Element Placement, each of which is incorporated herein in by reference.

The percutaneous access device 10 may be released from the bone anchor by rotating the percutaneous access device 10 about its longitudinal axis 16 and retracting the device 10 distally.

Figure 14:
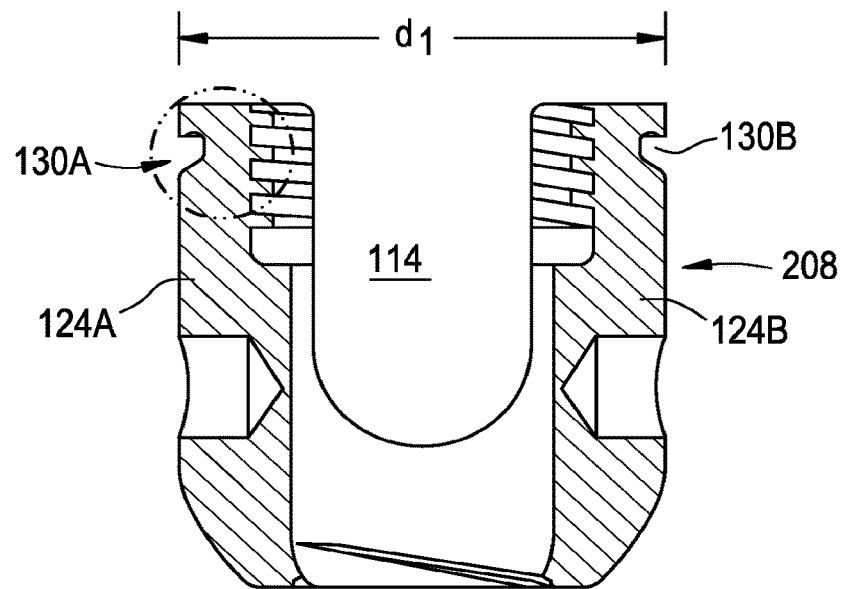
FIG. 14 is a side elevational view in cross section of the receiving member of the bone anchor assembly of FIG. 12.
Figure 15:
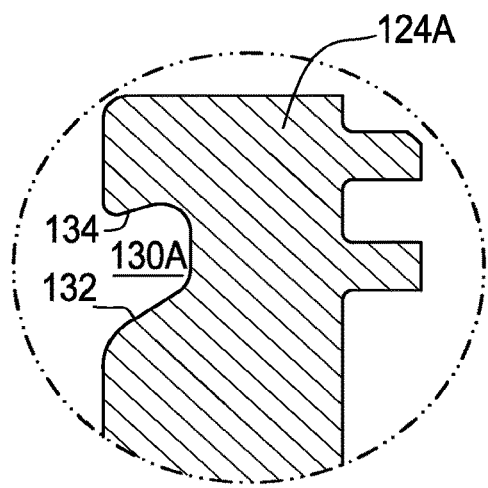
FIG. 15 is a side elevational view in cross section of an arcuate groove of the receiving member of the bone anchor assembly of FIG. 12.
Figure 16:
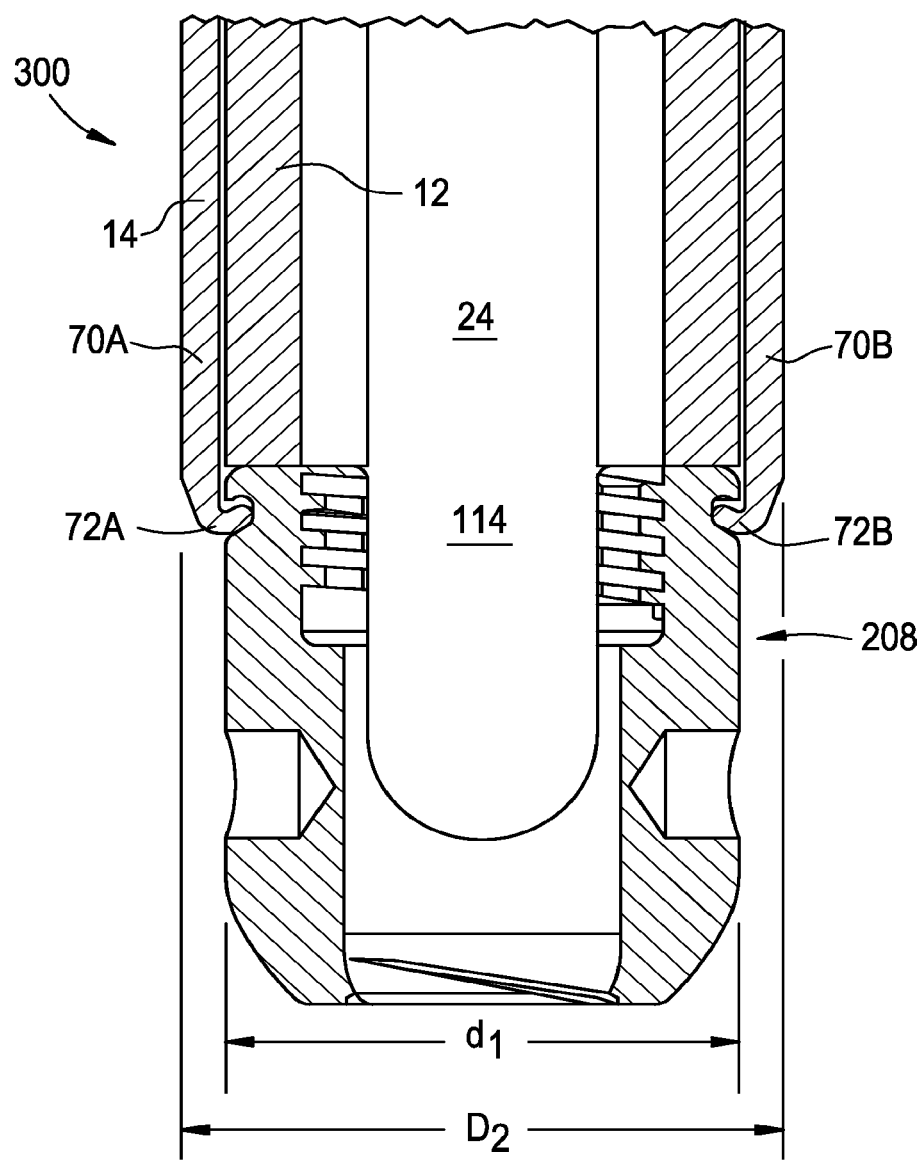
FIG. 16 is a side elevational view in cross-section of the distal end of the another exemplary embodiment of a percutaneous access device coupled to the receiving member of the bone anchor assembly of FIG. 12.

FIGS. 12-16 illustrate an alternative exemplary embodiment of a bone anchor assembly 200 and an exemplary percutaneous access device 300 that may be configured to releasably engage the bone anchor assembly 200. The exemplary bone anchor assembly 200 is analogous in construction to the exemplary bone anchor assembly 10 described above, except that the receiving member 208 of the bone anchor assembly 200 has a generally constant outer diameter $d_1$, as illustrated in FIGS. 14 and 16, at the proximal end 110 thereof, and, thus, lacks the reduced diameter portion 150 of bone anchor assembly 100. As a result, the outer diameter of the distal end 32 of the outer tube 14 of the exemplary percutaneous access device 300, indicated by line $D_2$ in FIG. 16, may be approximately equal to or, as in the illustrated embodiment, may be greater than the diameter $d_1$ of the proximal end 110 of the receiving member 208. The outer diameter of the outer tube 14 may be constant, as in the illustrated exemplary embodiment, or may vary along the length of the outer tube 14.

Figure 17A:
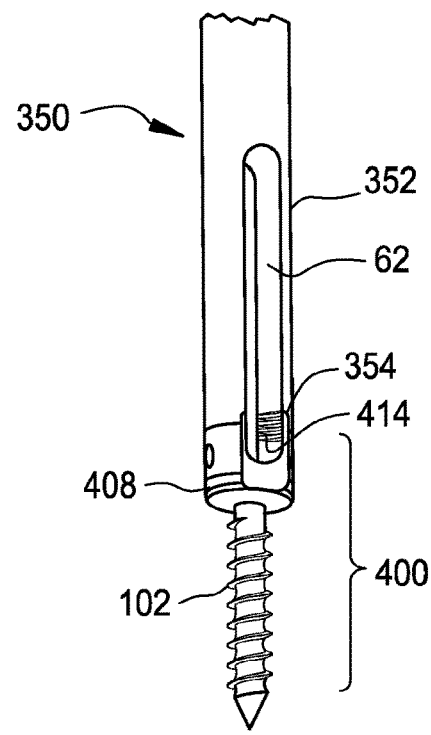
FIGS. 17A and 17B are perspective views of an alternative embodiment of a percutaneous access device and a bone anchor assembly, illustrating a threaded connecting between the percutaneous access device and the bone anchor assembly.
Figure 17B:
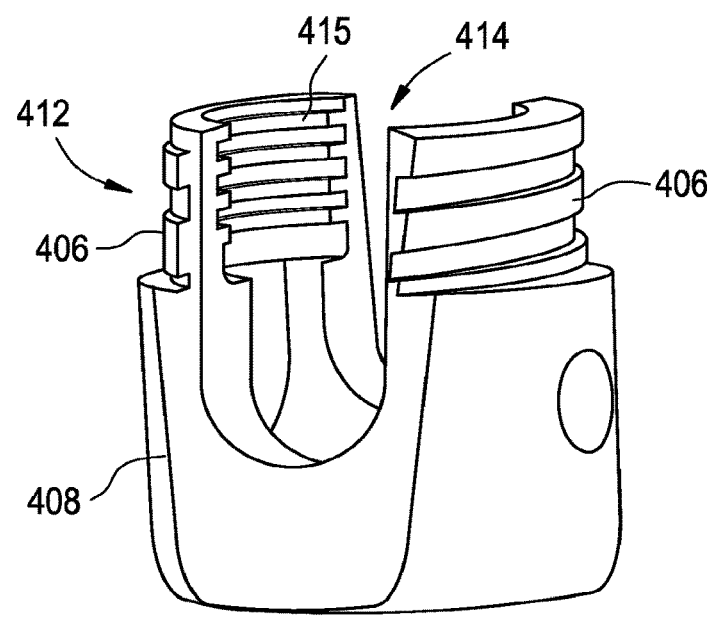
Figure 19A:
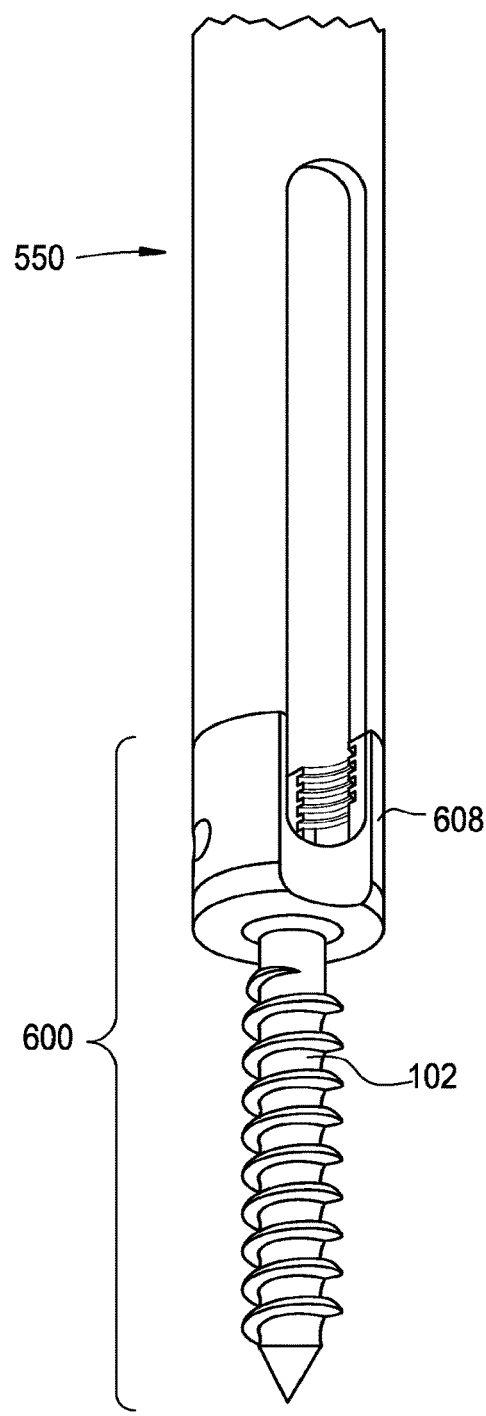
FIGS. 19A-19D are perspective views of an alternative embodiment of a percutaneous access device and a bone anchor assembly, illustrating the percutaneous access device and the bone anchor assembly interconnected by one or more internal wires.
Figure 19B:
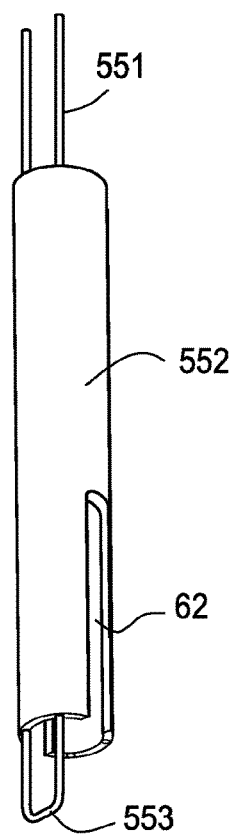
Figure 19C:
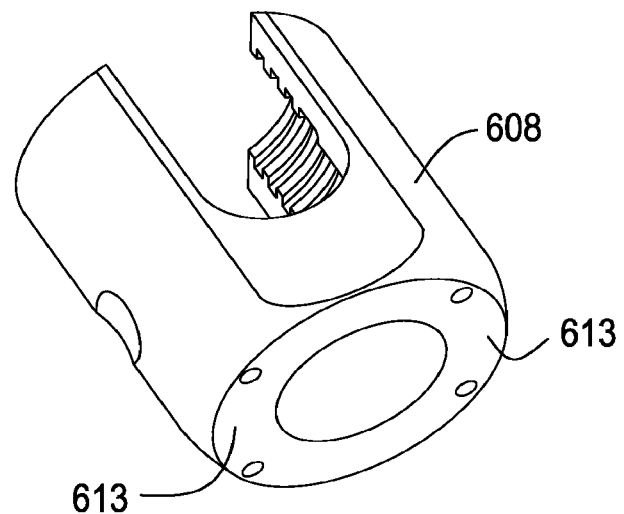
Figure 19D:
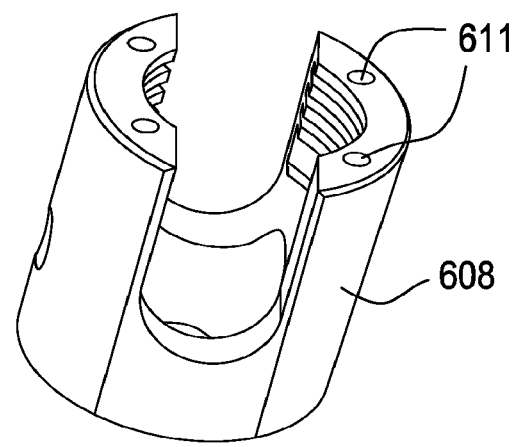
Figure 20A:
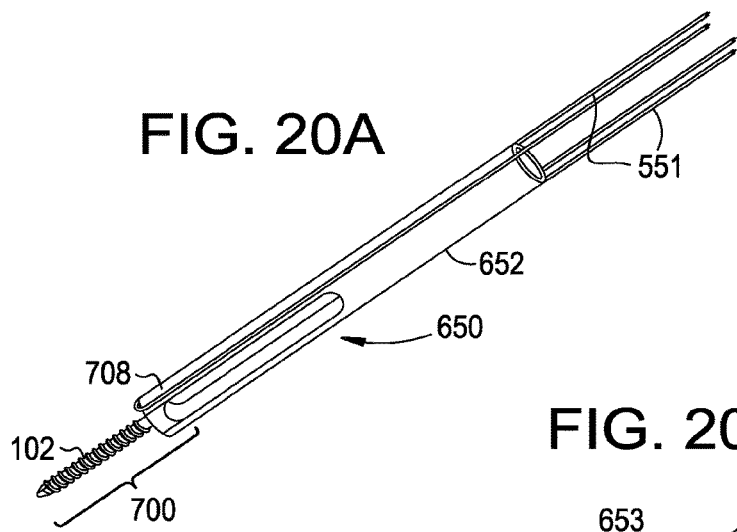
FIGS. 20A-20D are perspective views of an alternative embodiment of a percutaneous access device and a bone anchor assembly, illustrating the percutaneous access device and the bone anchor assembly interconnected by one or more external wires.
Figure 20B:
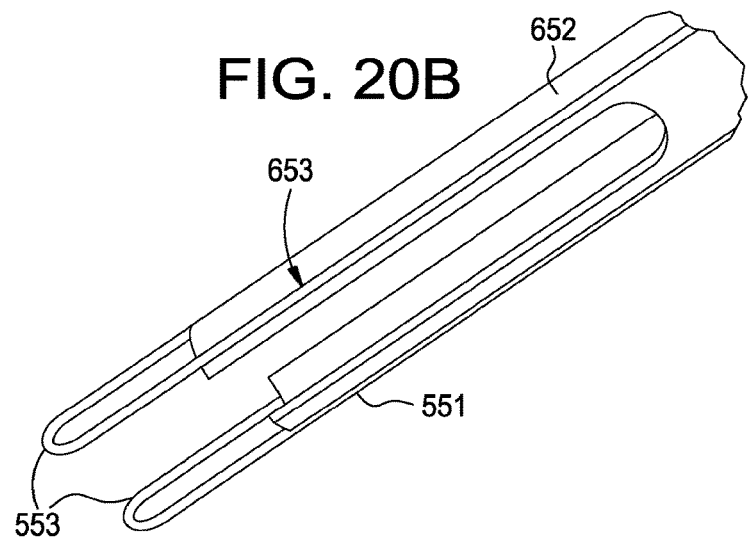
Figure 20C:
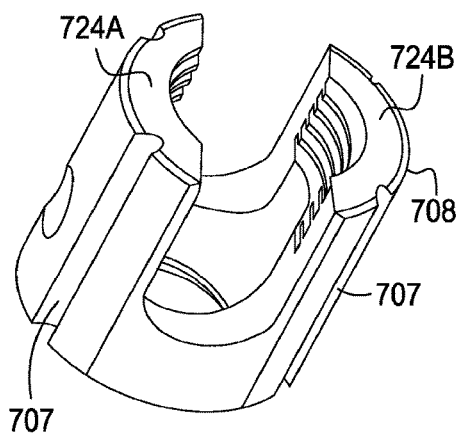
Figure 20D:
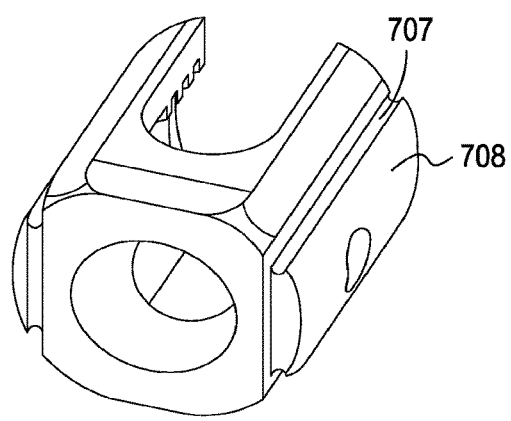

FIGS. 17A and 17B illustrate an alternative embodiment of a percutaneous access device 350 and a bone anchor assembly 400, in which the percutaneous access device and the bone anchor assembly are interconnected by threads. For example, the percutaneous access device 350 may have an outer tube 352 having a distal end 354 provided within internal threads that releasably engage external threads 406 provided on the proximal end 412 of the receiving member 408 of the bone anchor assembly 400. Preferably, the external threads 406 are clocked to facilitate alignment of the grooves 62, if any, provided on the outer tube 14 with the recess 414 provided in the receiving member 408. In the illustrated exemplary embodiment, the percutaneous access device 350 includes a single tube, outer tube 352; an inner tube may be provided but is not necessary.

FIGS. 18A and 18B illustrate an alternative embodiment a bone anchor assembly 500, in which the receiving member 508 includes one or more removable, externally threaded tabs 502 that provide a threaded connecting between the percutaneous access device 350 and the bone anchor assembly 500. In the illustrated exemplary embodiment, a pair of proximally extending tabs 502A and 502B extend from the legs 524A and 524B, respectively. Each tab 502, in the illustrated exemplary embodiment, is generally arcuate in shape and includes external threads for engagement with internal threads provided on the percutaneous access device. The tabs 502 may include internal threads 415 to facilitate advancement of a closure mechanism to the bone anchor assembly. Tabs 502 may be sheared off the bone anchor assembly 500 by over tightening of the percutaneous access device 350 or, alternatively, may be removed from the bone anchor assembly 500 after withdrawal of the percutaneous access device 350 by a suitable instrument.

FIGS. 19A-19D illustrate an alternative embodiment of a percutaneous access device 550 and a bone anchor assembly 600, in which the percutaneous access device 500 and the bone anchor assembly 600 are releasably interconnected by one or more internal wires 551. In the illustrated exemplary embodiment, for example, a pair of wires 551, extend axially through opposing side walls of the outer tube 552. Each wire extends through parallel axial holes provided in the side walls of the outer tube 552. Each wire 551 may form a loop 553 that can engage the receiving member 608 of the bone anchor assembly. The wires may be formed of any suitable biocompatible material including, for example a metal, such as a stainless, or a polymer. The receiving member 608, in the exemplary embodiment, includes two pairs of axially extending holes 611 for receiving wires 551. Each pair of holes 611 may terminate in a groove 613 oriented perpendicular to the holes 611. The number of wires and holes provided in the outer tube and the receiving member may be varied depending on the application. Each wire 551 may be tensioned to couple the percutaneous access device 550 to the bone anchor assembly. The wires 551 may be tensioned by, for example, retracting the wires 551 distally. Releasing the tension on the wires 551 by, for example, cutting the wires 551 or advancing the wires 551 proximally, can release the percutaneous access device 550 from the bone anchor assembly 600. In the illustrated exemplary embodiment, the percutaneous access device 550 includes a single tube, outer tube 552; an inner tube may be provided but is not necessary.

FIGS. 20A-20D illustrates an alternative embodiment of a percutaneous access device 650 and a bone anchor assembly 700 in which the percutaneous access device 650 and the bone anchor assembly 700 are releasably interconnected by one or more externally positioned wires 551. The illustrated exemplary embodiment, wires 551 extend axially along the exterior surface of the outer tube 652 of the percutaneous access device 650 and extend axially along the exterior surface of the receiving member 708 of the bone anchor assembly 700. The outer tube 652 may include one or more axially oriented grooves 653 in which the wires 551 may be seated. Likewise, the receiving member 708 may include one or more grooves 707 in which the wires 651 may be seated. The number of wires and/or grooves may be varied depending upon the particular application. In the illustrated embodiment, for example, a pair of parallel grooves 653 are provided in opposing sidewalls of the outer tube 652 and a pair of parallel of grooves 707 are provided in the opposing legs 724A, 724B of the receiving member 708. Each wire 551 may be tensioned to couple the percutaneous access device 650 to the bone anchor assembly 700. The wires 551 may be tensioned by, for example, retracting the wires 551 distally. Releasing the tension on the wires 551 by, for example, cutting the wires 551 or advancing the wires 551 proximally, can release the percutaneous access device 650 from the bone anchor assembly 700. In the illustrated exemplary embodiment, the percutaneous access device 650 includes a single tube, outer tube 652; an inner tube may be provided but is not necessary.

Figure 21:
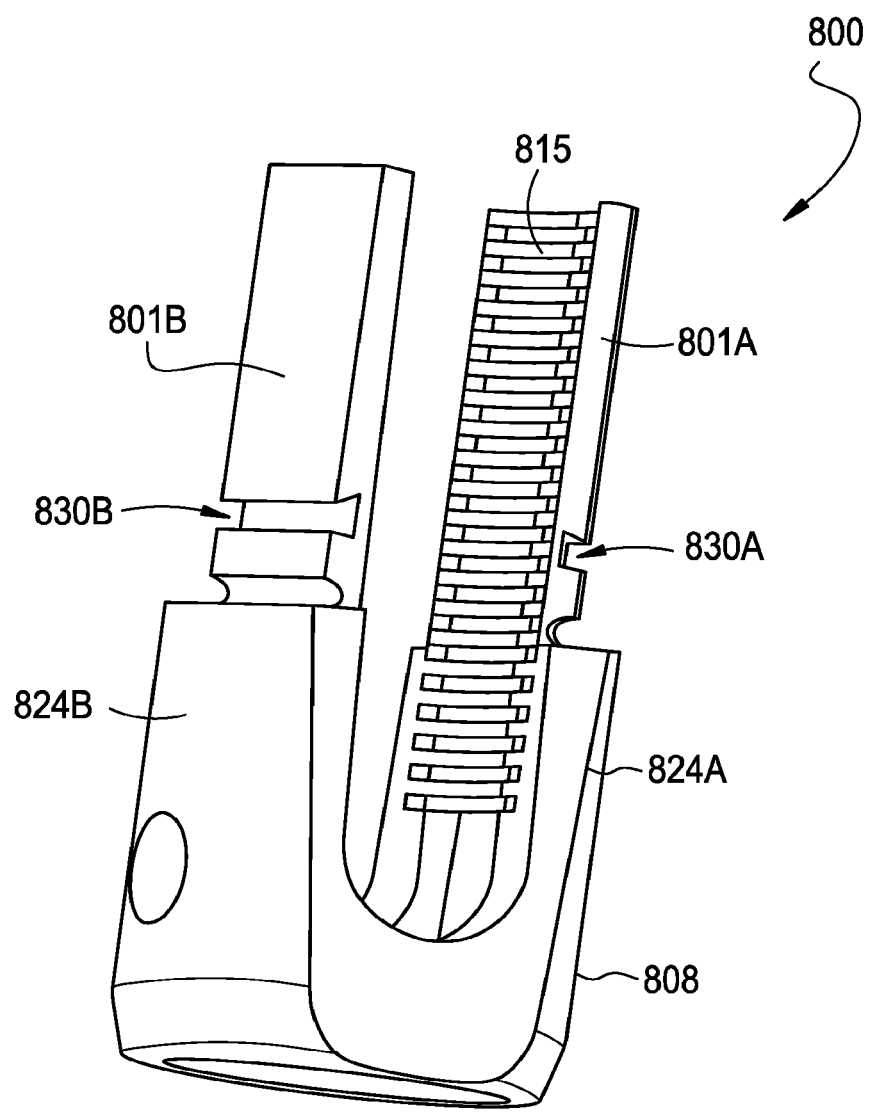
FIG. 21 is a perspective view of an alternative embodiment of a bone anchor assembly having a plurality of removable tabs for releasable engagement with an instrument such as a percutaneous access device.

FIG. 21 illustrates an alternative embodiment of a bone anchor assembly 800 having one or more removable tabs 801 for releasable engagement with an instrument such as an embodiment of a percutaneous access device described above. In the illustrated exemplary embodiment, a pair of opposing tabs 801A, 801B extend proximally from the proximal end of the receiving member 808 of the bone anchor assembly 800. Each tab 801A, 801B, in the illustrated exemplary embodiment, is generally arcuate in shape and are positioned proximal to and extend from a respective leg 824A, 824B of the receiving member 808. The size, shape, and number of tabs 801 may be varied without departing from the scope of the present invention. The tabs 801 may include a mechanism for facilitating releasable engagement by an instrument. For example, the tabs may be provided with external threads, as in the case of the embodiment illustrated in FIGS. 17A, 17B described above, or may include one or more grooves. In the illustrated exemplary embodiment, each tab 801A, 801B includes one or more arcuate grooves 830A, 830B that may be analogous in construction to the grooves 130A, 130B described above. The tabs 801 may include internal threads 815 to facilitate advancement of a closure mechanism to the bone anchor assembly. Tabs 801 may be sheared off the bone anchor assembly 800 by the percutaneous access device or instrument or, alternatively, may be removed from the bone anchor assembly 800 after withdrawal of the percutaneous access device or instrument using a suitable instrument.

Figure 22A:
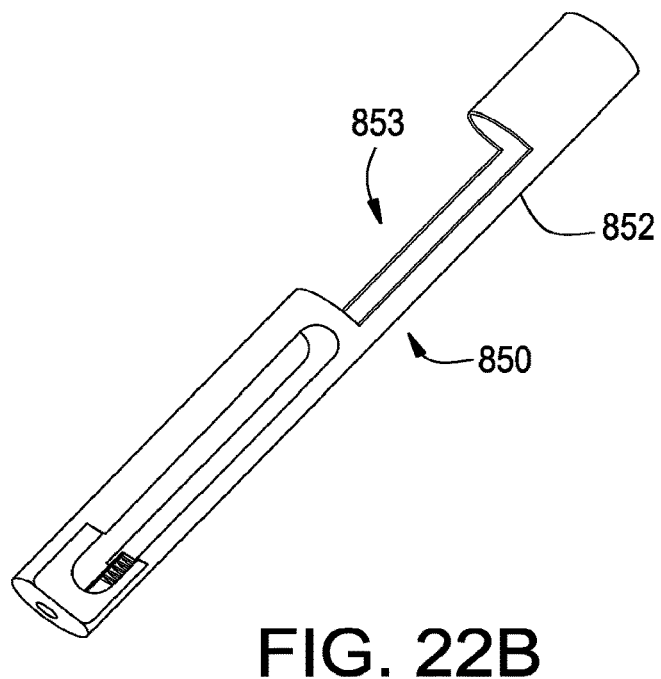
FIGS. 22A-22B are perspective views of an exemplary embodiment of a percutaneous access device, illustrating axial cut-outs provided in the outer tube of the percutaneous access device.
Figure 22B:
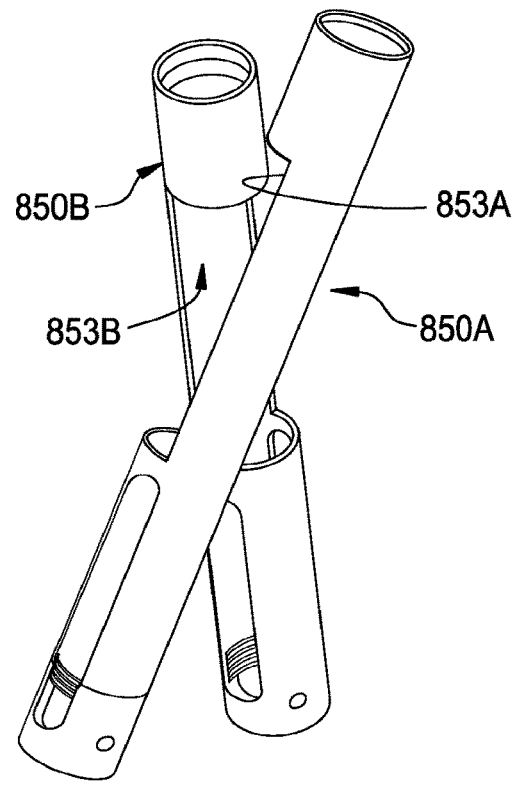

FIGS. 22A-22B illustrates an exemplary embodiment of a percutaneous access device 850 having one or more axially extending cut-outs 853 provided in the outer tube 852 of the percutaneous access device. As illustrated in FIG. 22B, an axially extending cut-out 853 may facilitate the use of multiple percutaneous access devices by minimizing interference between the devices. For example, in certain spinal applications, bone anchors placed on adjacent vertebrae may be closely spaced and/or angled in a manner that may cause interference between instruments, such as a percutaneous access device disclosed herein, used simultaneously with the adjacent bone anchors. By providing axial cut-outs 853, two or more percutaneous access devices 850A, 850B may be employed on adjacent bone anchors, or closely positioned anchors, by aligning the cut-outs 853A, 853B. The length and depth of a cut-out 852 may be varied depending on the application. One or more cut-outs may be provided on any of the exemplary embodiments of the percutaneous access device described herein or with other instruments used with bone anchors, e.g., drills, drivers, cannulas, approximators, and the like. In embodiments including an inner tube or additional tubes, the additional tubes may also be provided with cut-outs 853.

FIGS. 23A-23B illustrates an alternative embodiment of a percutaneous access device 950 and a bone anchor assembly 900 in which the distal end 956 of the inner tube 954 of the percutaneous access device 950 includes one or more flexible bone anchor engaging tabs 958 for releasable engagement with the receiving member 908 of bone anchor assembly 900. In the exemplary embodiment, a pair of opposing tabs 958A, 958B extend distally from the distal end 956 of the inner tube 954. Each tab 958, in the illustrated exemplary embodiment, is connected at a proximal end to the inner tube 954 and has a free distal end 960. One or both of the tabs 958 can flex from a first position, in which the tab 958 is oriented approximately axially, e.g., parallel to the longitudinal axis of the inner tube 954, to a second position, in which the tab 958 is generally oriented at angle to the longitudinal axis of the inner tube 954. In the exemplary embodiment, for example, each tab 958A, 958B may flexed radially outward, e.g., away from each other, from a first position, in which the tabs 958A, 958B are approximately parallel, to a second, flexed positioned, in which the tabs 958A, 958B are oriented at an angle to one another. The tabs 958 may be biased to the first position. For example, the tabs 958A, 958B may be biased to the first, parallel position, such that the tabs 958A, 958B may provide a radially compressive force on the receiving member 908 to releasably engage the receiving member 908. One or more of the tabs 958 may be provided with a projection or the like for engaging a hole, groove, etc, that may be provided in the exterior surface of the receiving member 908. Although the exemplary embodiment includes two tabs 958A, 958B, any number (one or more) tabs 958 may be provided.

The percutaneous access device 950 may include an outer tube 952 that may be advanced about the tabs 958 when the tabs 958 releasably engage the receiving member 908. For example, in the illustrated exemplary embodiment, the outer tube 952 may be advanced distally about the tabs 958A, 958B when the tabs are in the second, flexed position, to inhibit separation of the tabs 958A, 958B and/or provide a radially compressive force on the tabs.

While the percutaneous access systems and bone anchor assemblies of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

A bone anchor is preferably cannulated to allow a k-wire to extend through the anchor and the access device to guide the devices toward the implant site.

A variety of closure mechanisms and tools for delivering closure mechanisms are known in the art and they can be used with the present invention. By way of non-limiting example, a driver tool can be disposed through an access device for applying a closure mechanism, such as a set screw, to a receiver head of a spinal anchor.

The invention claimed is:

1. A method for implanting a rod implant along a spine of a patient back, the method comprising:
   coupling an elongated guide tool to a head of a bone anchor,
   wherein the elongated guide tool comprises an anchor coupling region comprising a first leg spaced apart from a second leg, the first leg comprising an attachment structure projecting radially inward,
   wherein the head comprises:
      an outer surface facing radially outward relative to a longitudinal center axis of the head; and
      a slot extending along at least a portion of the outer surface in a direction perpendicular to the longitudinal center axis of the head, and
   wherein the coupling comprises causing the first and second legs to be splayed apart as the head is received between the first and second legs followed by the attachment structure being received in the slot; and
   employing the elongated guide tool to deliver the rod implant into a channel of the head when an anchoring member of the bone anchor is anchored in a vertebra of the spine, the anchoring member extending distally from the head, the elongated guide tool extending proximally from the head and through a minimally invasive incision in the patient back;
   wherein the coupling further comprises proximally axially urging the elongated guide tool relative to the head.

2. The method of claim 1, wherein the coupling further comprises driving the first and second legs distally relative to the head, the head passing proximally between the first and second legs along a longitudinal axis of the elongated guide tool.

3. The method of claim 1, wherein the proximally axially urging facilitates the attachment structure being received in the slot in a manner that discourages splaying of the first and second legs.

4. The method of claim 1, wherein the bone anchor comprises a bone screw.

5. The method of claim 4, wherein the bone screw comprises a polyaxial bone screw.

6. The method of claim 1, wherein the anchoring member is longitudinally cannulated.

7. The method of claim 1, wherein the slot comprises a recessed overhanging configuration at a proximal boundary of the slot, and the attachment structure comprises a proximally pointing free extent that is received by the recessed overhanging configuration.

8. The method of claim 1, further comprising delivering a threaded closure top into the channel via a route extending along a longitudinal axis of the elongated guide tool, and threading the threaded closure top into the channel to secure the rod implant within the channel.

9. The method of claim 8, wherein the route extending along the longitudinal axis of the elongated guide tool extends along an interior of the elongated guide tool.

10. The method of claim 9, wherein a closure installation tool extends along the route in threading the threaded closure top into the channel.

11. The method of claim 1, further comprising rotating the elongated guide tool relative to the head to disconnect the elongated guide tool from the head once the rod implant is implanted.

12. The method of claim 1, wherein the slot intersects the channel.

13. The method of claim 1, wherein the rod implant minimally invasively enters the patient by causing a first end of the rod implant to lead the rod implant into the elongated guide tool.

14. A method for implanting a rod implant along a spine of a patient back, the method comprising:
   coupling a tool to a head of a bone anchor,
   wherein the tool comprises an anchor coupling region comprising an attachment structure projecting radially inward, wherein the head comprises:
      an outer surface facing radially outward relative to a longitudinal center axis of the head;
      a slot extending along at least a portion of the outer surface in a direction perpendicular to the longitudinal center axis of the head;
      a threaded inner surface facing radially inward towards the longitudinal center axis of the head; and
      a channel extending distally along the longitudinal center axis of the head from a proximal end of the head, and wherein the coupling comprises causing the attachment structure to be received in the slot;
   delivering the rod implant into the channel of the head when an anchoring member of the bone anchor is anchored in a vertebra of the spine, the anchoring member extending distally from the head; and
   with the tool coupled to the head via the attachment structure being received in the slot, threading a threaded closure top into threaded engagement with the threaded inner surface;
   wherein the slot intersects the channel.

15. The method of claim 14, wherein the anchor coupling region further comprises a first leg spaced apart from a second leg, the attachment structure projecting radially inward from the first leg.

16. The method of claim 15, wherein the coupling further comprises driving the first and second legs distally relative to the head, the head passing proximally between the first and second legs along a longitudinal axis of the tool.

17. The method of claim 14, wherein the bone anchor comprises a bone screw.

18. The method of claim 17, wherein the bone screw comprises a polyaxial bone screw.

19. The method of claim 14, wherein the anchoring member is longitudinally cannulated.

20. The method of claim 14, wherein the slot comprises a recessed overhanging configuration at a proximal boundary of the slot, and the attachment structure comprises a proximally pointing free extent that is received by the recessed overhanging configuration.

21. The method of claim 14, further comprising delivering the threaded closure top into the channel via a route extending along a longitudinal axis of the tool, and the threading of the threaded closure top into threaded engagement with the threaded inner surface securing the rod implant within the channel.

22. The method of claim 21, wherein the route extending along the longitudinal axis of the tool extends along an interior of the tool.

23. The method of claim 22, wherein a closure installation tool extends along the route in threading the threaded closure top into the channel.

24. The method of claim 14, wherein delivering the rod implant into the channel of the head comprises employing the tool to deliver the rod implant into the channel with: the anchoring member of the bone anchor anchored in the vertebra of the spine, the anchoring member extending distally from the head; and the tool coupled to the head via the attachment structure being received in the slot, the tool extending proximally from the head and through a minimally invasive incision in the patient back.

25. The method of claim 24, wherein the rod implant minimally invasively enters the patient by causing a first end of the rod implant to lead the rod implant into the tool.

26. A method for implanting a rod implant along a spine of a patient back, the method comprising:
coupling an elongated guide tool to a head of a bone anchor,
wherein the elongated guide tool comprises an anchor coupling region comprising a first leg spaced apart from a second leg, the first leg comprising an attachment structure projecting radially inward,
wherein the head comprises:
an outer surface facing radially outward relative to a longitudinal center axis of the head; and
a slot extending along at least a portion of the outer surface in a direction perpendicular to the longitudinal center axis of the head, and
wherein the coupling comprises causing the first and second legs to be splayed apart as the head is received between the first and second legs followed by the attachment structure being received in the slot; and
employing the elongated guide tool to deliver the rod implant into a channel of the head when an anchoring member of the bone anchor is anchored in a vertebra of the spine, the anchoring member extending distally from the head, the elongated guide tool extending proximally from the head and through a minimally invasive incision in the patient back;
wherein the slot intersects the channel.

27. The method of claim 26, wherein the coupling further comprises driving the first and second legs distally relative to the head, the head passing proximally between the first and second legs along a longitudinal axis of the elongated guide tool.

28. The method of claim 26, wherein the bone anchor comprises a bone screw.

29. The method of claim 28, wherein the bone screw comprises a polyaxial bone screw.

30. The method of claim 26, wherein the anchoring member is longitudinally cannulated.

31. The method of claim 26, wherein the slot comprises a recessed overhanging configuration at a proximal boundary of the slot, and the attachment structure comprises a proximally pointing free extent that is received by the recessed overhanging configuration.

32. The method of claim 26, further comprising delivering a threaded closure top into the channel via a route extending along a longitudinal axis of the elongated guide tool, and threading the threaded closure top into the channel to secure the rod implant within the channel.

33. The method of claim 32, wherein the route extending along the longitudinal axis of the elongated guide tool extends along an interior of the elongated guide tool.

34. The method of claim 33, wherein a closure installation tool extends along the route in threading the threaded closure top into the channel.

35. The method of claim 26, further comprising rotating the elongated guide tool relative to the head to disconnect the elongated guide tool from the head once the rod implant is implanted.

36. The method of claim 26, wherein the rod implant minimally invasively enters the patient by causing a first end of the rod implant to lead the rod implant into the elongated guide tool.

* * * * *